(12) United States Patent
Hakoshima et al.

(10) Patent No.: US 10,832,401 B2
(45) Date of Patent: Nov. 10, 2020

(54) DIAGNOSIS ASSISTING APPARATUS AND METHOD FOR ASSISTING DIAGNOSIS

(71) Applicant: JVC KENWOOD Corporation, Yokohama (JP)

(72) Inventors: Shuji Hakoshima, Yokohama (JP); Katsuyuki Shudo, Yokohama (JP); Masaru Ninomiya, Yokohama (JP); Makoto Kito, Yokohama (JP)

(73) Assignee: JVC KENWOOD Corporation, Yokohama (JP)

( * ) Notice: Subject to any disclaimer, the term of this patent is extended or adjusted under 35 U.S.C. 154(b) by 5 days.

(21) Appl. No.: 15/867,125

(22) Filed: Jan. 10, 2018

(65) Prior Publication Data

US 2018/0130206 A1    May 10, 2018

Related U.S. Application Data

(63) Continuation of application No. 14/670,013, filed on Mar. 26, 2015, now Pat. No. 9,898,816, which is a
(Continued)

(30) Foreign Application Priority Data

Sep. 28, 2012  (JP) .................................. 2012-218834
Sep. 28, 2012  (JP) .................................. 2012-218848
(Continued)

(51) Int. Cl.
*H04N 7/18*       (2006.01)
*G06T 7/00*       (2017.01)
(Continued)

(52) U.S. Cl.
CPC ............ *G06T 7/0012* (2013.01); *A61B 3/113* (2013.01); *A61B 17/0644* (2013.01); *H04N 7/18* (2013.01);
(Continued)

(58) Field of Classification Search
CPC ............. F04C 2270/0421; A61B 3/113; A61B 17/0644; G06K 9/00604; G06T 2207/30041; G06T 7/0012; H04N 7/18
See application file for complete search history.

(56) References Cited

U.S. PATENT DOCUMENTS

2008/0080846 A1    4/2008  Grip
2011/0234832 A1*   9/2011  Ezoe .................. H04N 5/23206
                                                      348/222.1
(Continued)

FOREIGN PATENT DOCUMENTS

JP    2005-185431 A    7/2005
JP    2005-198743 A    7/2005
(Continued)

OTHER PUBLICATIONS

Pierce, "Preference for Geomateric Patterns Early in Life as a Risk Factor for Autisim," Arch Gen Psychiatry, Jan. 2011, vol. 68 No. 1, pp. 101-109 [Cited in Parent].
(Continued)

*Primary Examiner* — Peet Dhillon
(74) *Attorney, Agent, or Firm* — Amin, Turocy & Watson, LLP

(57) ABSTRACT

A diagnosis assisting apparatus includes a display, an imaging unit configured to image a subject, a line of sight detecting unit configured to detect a line of sight direction of the subject from a picked-up image imaged by the imaging unit, a point of view detecting unit configured to detect a point of view of the subject in a display region of the display based on the line of sight direction, and an output controller configured to display a diagnostic image including a natural image and a geometrical image, and the point of view detecting unit detects the point of view of the subject in a case where the diagnostic image is displayed.

2 Claims, 57 Drawing Sheets

Related U.S. Application Data continuation of application No. PCT/JP2013/076158, filed on Sep. 26, 2013.

(30) Foreign Application Priority Data

| Sep. 28, 2012 | (JP) | 2012-218849 |
|---|---|---|
| Sep. 28, 2012 | (JP) | 2012-218850 |
| Sep. 28, 2012 | (JP) | 2012-218851 |
| Sep. 28, 2012 | (JP) | 2012-218852 |
| Sep. 28, 2012 | (JP) | 2012-218875 |
| Sep. 28, 2012 | (JP) | 2012-218876 |
| Sep. 28, 2012 | (JP) | 2012-218877 |

(51) Int. Cl.
  *A61B 3/113* (2006.01)
  *A61B 17/064* (2006.01)
  *G06K 9/00* (2006.01)

(52) U.S. Cl.
  CPC .. *F04C 2270/0421* (2013.01); *G06K 9/00604* (2013.01); *G06T 2207/30041* (2013.01)

(56) References Cited

U.S. PATENT DOCUMENTS

| 2011/0242486 A1* | 10/2011 | Ebisawa | G16H 50/30 |
| | | | 351/206 |
| 2012/0293486 A1* | 11/2012 | Adachi | G06T 7/248 |
| | | | 345/418 |
| 2013/0108175 A1* | 5/2013 | Ptucha | G06T 11/60 |
| | | | 382/199 |
| 2014/0213930 A1 | 7/2014 | Mori et al. | |
| 2015/0050628 A1* | 2/2015 | Mori | A61B 5/167 |
| | | | 434/236 |

FOREIGN PATENT DOCUMENTS

| JP | 2008-125619 A | 6/2008 |
| JP | 2011-206542 A | 10/2011 |
| JP | 2011-217764 A | 11/2011 |
| JP | 2012-080910 A | 4/2012 |
| WO | 2012/020760 A1 | 2/2012 |

OTHER PUBLICATIONS

International Search Report in PCT Application No. PCT/JP2013/076158, dated Oct. 22, 2013 [Cited in Parent].

Office Action in Japanese Patent Application No. 2012-218834, dated Jan. 5, 2016 [Cited in Parent].

Office Action in Japanese Patent Application No. 2012-218849, dated Jan. 5, 2016 [Cited in Parent].

Extended European Search Report in counterpart European Application No. 13841259.8, dated Sep. 6, 2016 [Cited in Parent].

McPartland (Patterns of Visual Attention to Faces and Objects in Autism Spectrum Disorder; Retrieved: Jun. 8, 2017; Pub: Feb. 2011; pp. 1-19; URL: https://www.ncbi.nlm.nih.gov/pmc/articles/PMC3074360/) [Cited in Parent].

\* cited by examiner

FIRST QUADRANT
UPPER SIDE

DIAGNOSIS ASSISTING APPARATUS AND METHOD FOR ASSISTING DIAGNOSIS

CROSS-REFERENCE TO RELATED APPLICATION(S)

This application is a continuation of U.S. patent application Ser. No. 14/670,013, filed Mar. 26, 2015, which is a Continuation of International Application No. PCT/JP2013/076158, filed on Sep. 26, 2013, which claims the benefit of priority from Japanese Patent Applications No. 2012-218834, No. 2012-218848, No. 2012-218849, No. 2012-218850, No. 2012-218851, No. 2012-218852, No. 2012-218875, No. 2012-218876, No. 2012-218877, filed on Sep. 28, 2012; the entire contents of which are incorporated herein by reference.

BACKGROUND OF THE INVENTION

1. Field of the Invention

The present invention relates to a diagnosis assisting apparatus and a method for assisting diagnosis.

2. Description of the Related Art

In recent years, people having developmental disorder has been said to be increased. It has been found that the symptom of the developmental disorder is reduced by finding the symptom early and starting rehabilitation and this increases the effect to adapt to the society. In Japan, it is desired to find the developmental disorder in an early stage by an interview at the time of medical checkup for half-past-one-year-old children. However, the effect is not enough because there is a problem such as shortage of psychiatrists and to take a long time for the interview. There is a need for an objective and efficient diagnosis assisting apparatus of the developmental disorder.

To find the developmental disorder in an early stage, for example, the diagnosis at the time of the medical checkup for half-past-one-year-old children is ideal. Also, it is necessary to consider the use at the time of the medical checkup. A behavior that the child does not look at eyes of a person facing the child (turn his/her eyes away) can be considered as characteristics of the developmental disorder child. There is a method for detecting the point of regard by photographing a face of a human by using a camera and calculating a corneal reflex and a pupil position. A method for assisting the diagnosis of the developmental disorder by applying the above method has been proposed.

In Japanese Laid-open Patent Publication No. 2005-185431, a method has been provided in which an eye region and a mouth region surely including a mouth of a subject to be observed are specified and the number of the frames is calculated. However, a detection method with higher accuracy has been required. The number of the frames includes the number of frames of the moving image in which the point of regard coordinate is detected in the eye region, the number of the frames of the moving image in which the point of regard coordinate is detected in the mouth region, the number of the frames of the moving image in which the point of regard coordinate is detected in a region other than the eye region, and the number of all the frames to be calculated.

Therefore, there is a need for a diagnosis assisting apparatus and a method for assisting the diagnosis which can improve diagnosis accuracy.

SUMMARY OF THE INVENTION

It is an object of the present invention to at least partially solve the problems in the conventional technology.

There is provided a diagnosis assisting apparatus that includes a display, an imaging unit configured to image a subject, a line of sight detecting unit configured to detect a line of sight direction of the subject from a picked-up image imaged by the imaging unit, a point of view detecting unit configured to detect a point of view of the subject in a display region of the display based on the line of sight direction, and an output controller configured to display a diagnostic image including a natural image and a geometrical image on the display and the point of view detecting unit detects the point of view of the subject in a case where the diagnostic image is displayed.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of a diagnosis assisting apparatus and a method for assisting the diagnosis according to the present invention will be described in detail below with reference to the drawings. The present invention is not limited to the embodiments.

First Embodiment

Figure 1:
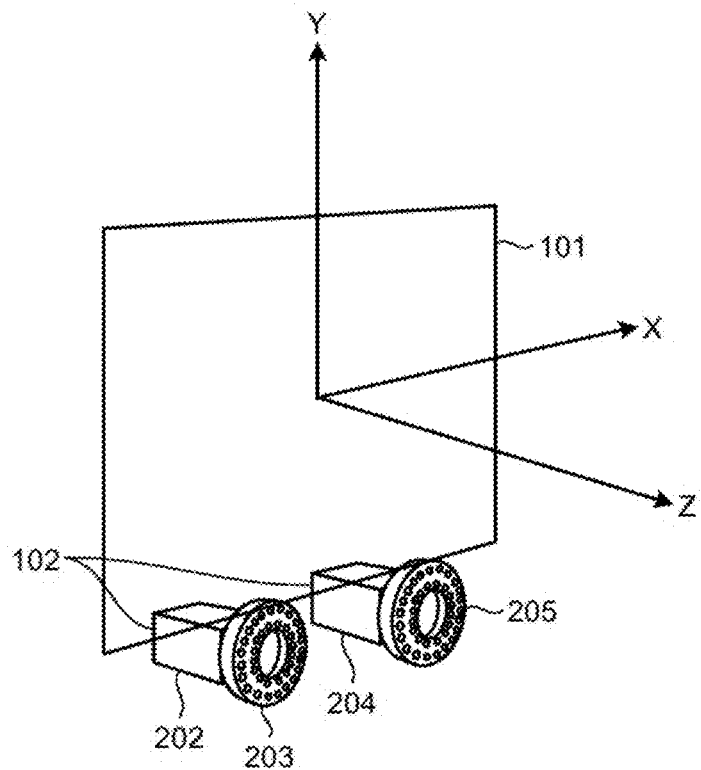
FIG. 1 is a diagram of an exemplary arrangement of a display, a stereo camera, and a light source used in a first embodiment.

FIG. 1 is a diagram of an exemplary arrangement of a display, a stereo camera, and a light source used in a first embodiment. As illustrated in FIG. 1, a pair of stereo cameras 102 is arranged under a display screen 101 in the first embodiment. The stereo cameras 102 are imaging units capable of stereoscopic photographing by using infrared rays and include a right camera 202 and a left camera 204.

Infrared light emitting diode (LED) light sources 203 and 205 are respectively arranged just in front of lens of the right camera 202 and the left camera 204 in the circumferential direction. The infrared LED light sources 203 and 205 include a LED of an inner circumference and a LED of an outer circumference. The LEDs have different light-emitting wavelengths from each other. The infrared LED light sources 203 and 205 detect pupils of a subject. For example, a method described in Japanese Laid-open Patent Publication No. 2008-125619 can be applied as a detection method of the pupils.

When a line of sight is detected, a position is specified by expressing a space with coordinate values. In the present embodiment, it is assumed that a central position of the display screen 101 be an origin. It is assumed that a vertical direction be indicated by a Y-coordinate (upside is +), a horizontal direction be indicated by an X-coordinate (right side is +), and a depth be indicated by a Z-coordinate (front side is +).

Figure 2:
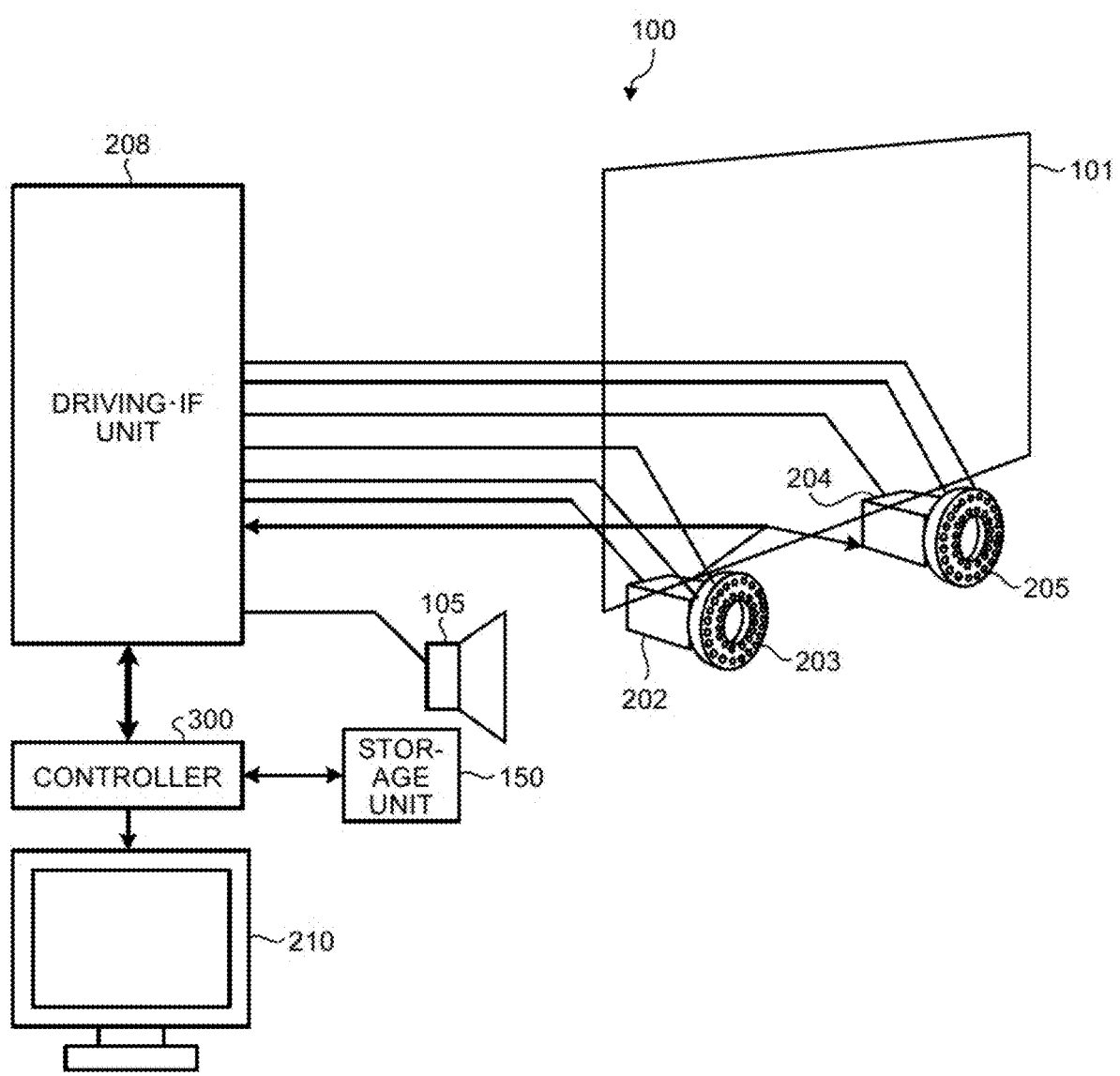
FIG. 2 is a diagram of an outline of a function of a diagnosis assisting apparatus according to the first embodiment.

FIG. 2 is a diagram of an outline of a function of a diagnosis assisting apparatus 100. In FIG. 2, a part of the structure illustrated in FIG. 1 and a structure used to drive the structure illustrated in FIG. 1 are illustrated. As illustrated in FIG. 2, the diagnosis assisting apparatus 100 includes the right camera 202, the left camera 204, the infrared LED light sources 203 and 205, a speaker 105, a driving•IF unit 208, a controller 300, a storage unit 150, and a display 210. The display screen 101 is illustrated to easily understand a positional relationship between the display screen 101 and the right camera 202 and the left camera 204 in FIG. 2. However, the display screen 101 is a screen displayed on the display 210.

The speaker 105 functions as a voice output unit for outputting voice and the like which attract the attention of the subject at the time of the calibration.

The driving•IF unit 208 drives each part included in the stereo camera 102. Also, the driving•IF unit 208 becomes an interface of each part included in the stereo camera 102 and the controller 300.

The storage unit 150 stores various information such as a control program, a measurement result, and a result of the diagnosis assistance. The storage unit 150 stores, for example, an image to be displayed on the display 210. The display 210 displays various information such as an object image for the diagnosis.

Figure 3:
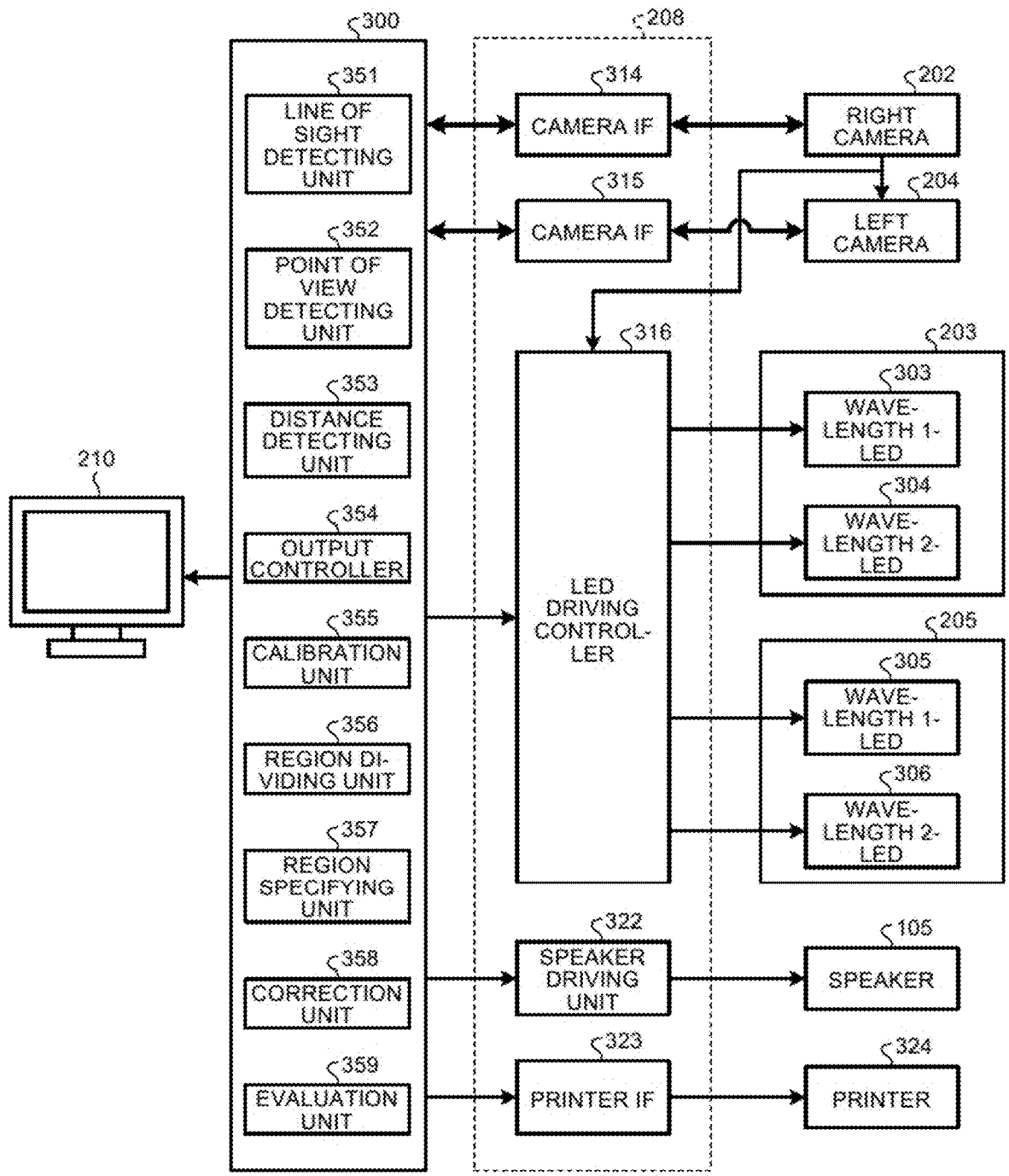
FIG. 3 is a block diagram of an exemplary detailed function of each part illustrated in FIG. 2.

FIG. 3 is a block diagram of an exemplary detailed function of each part illustrated in FIG. 2. As illustrated in FIG. 3, the controller 300 is connected to the display 210 and the driving•IF unit 208. The driving•IF unit 208 includes camera IFs 314 and 315, a LED driving controller 316, a speaker driving unit 322, and a printer IF 323.

The driving•IF unit 208 is connected to the right camera 202 and the left camera 204 respectively via the camera IFs 314 and 315. The driving•IF unit 208 drives these cameras so that a subject is imaged.

A frame synchronizing signal is output from the right camera 202. The frame synchronizing signal is input to the left camera 204 and the LED driving controller 316. Accordingly, the right and left infrared rays light sources with the wavelength 1 (wavelength 1-LED 303 and wavelength 1-LED 305) are made to emit light at different timings from each other in a first frame, and correspondingly, images taken by the left and right cameras (right camera 202 and left camera 204) are obtained. Then, the right and left infrared rays light sources with the wavelength 2 (wavelength 2-LED 304 and wavelength 2-LED 306) are made to emit light at different timings from each other in a second frame, and correspondingly, images taken by the right and left cameras are obtained.

The infrared LED light source 203 includes a wavelength 1-LED 303 and a wavelength 2-LED 304. The infrared LED light source 205 includes a wavelength 1-LED 305 and a wavelength 2-LED 306.

The wavelength 1-LEDs 303 and 305 irradiate infrared rays with the wavelength 1. The wavelength 2-LEDs 304 and 306 irradiate infrared rays with the wavelength 2.

Both the wavelengths 1 and 2 are respectively, for example, wavelengths shorter than 900 nm and equal to or longer than 900 nm. This is because when reflected light reflected by the pupil is imaged by irradiating the pupils with the infrared rays having the wavelength less than 900 nm, a brighter pupil image can be obtained compared with a case where the reflected light reflected by the pupils is imaged by irradiating the pupils with the infrared rays having the wavelength equal to or more than 900 nm.

The speaker driving unit 322 drives the speaker 105. The printer IF 323 is an interface to connect to a printer 324 as a printing unit. The printer 324 may be included in the diagnosis assisting apparatus 100.

The controller 300 controls the entire diagnosis assisting apparatus 100. The controller 300 includes a line of sight detecting unit 351, a point of view detecting unit 352, a distance detecting unit 353, an output controller 354, a calibration unit 355, a region dividing unit 356, a region specifying unit 357, a correction unit 358, and an evaluation unit 359.

The line of sight detecting unit 351 detects a line of sight (line of sight direction) of the subject from a picked-up image imaged by the imaging unit (stereo camera 102). Processing to detect the line of sight includes processing to detect eye positions of the subject (position detecting unit). The point of view detecting unit 352 detects a point of view of the subject by using the detected line of sight direction. The point of view detecting unit 352 detects the point of view (point of regard), for example, in the object image displayed on the display screen 101. The point of view is a point where the subject regards. All the methods which have been conventionally used can be applied as a method for detecting the line of sight by the line of sight detecting unit 351 and a method for detecting the point of view by the point of view detecting unit 352. A case will be described below as an example where the line of sight direction and the point of regard of the subject are detected by using the stereo camera as described in Japanese Laid-open Patent Publication No. 2005-198743.

In this case, first, the line of sight detecting unit 351 detects the line of sight direction of the subject from the image taken by the stereo camera 102. The line of sight detecting unit 351 detects the line of sight direction of the subject, for example, by using methods described in Japanese Laid-open Patent Publication No. 2005-185431 and Japanese Laid-open Patent Publication No. 2008-125619. Specifically, the line of sight detecting unit 351 obtains a difference between an image taken by irradiating the infrared rays with the wavelength 1 and an image taken by irradiating the infrared rays with the wavelength 2. Then, the line of sight detecting unit 351 generates an image in which a pupil image becomes clear. The line of sight detecting unit 351 calculates the positions of the pupils (eye positions) of the subject according to a stereovision method by using two images generated from the respective images taken by the right and left cameras (right camera 202 and left camera 204) as describe above. Also, the line of sight detecting unit 351 calculates a position of corneal reflex of the subject by using the images taken by the right and left cameras. The line of sight detecting unit 351 calculates a line of sight vector for expressing the line of sight direction of the subject from the pupil position and the corneal reflex position of the subject.

The detection method of the eye position and the line of sight of the subject is not limited to this. For example, the eye position and the line of sight of the subject may be detected by analyzing the image taken by using visible light, instead of the infrared rays.

The point of view detecting unit 352 detects an intersection point between a line of sight vector and a XY plane, for example, expressed by the coordinate system illustrated in FIG. 1 as the point of regard of the subject. When the lines of sight directions of both eyes can be obtained, the point of regard may be measured by obtaining an intersection point between the lines of sight of the right eye and the left eye of the subject.

The distance detecting unit 353 detects a distance between the imaging unit (stereo camera 102) and the eye position of the subject. In the present embodiment, the distance detecting unit 353 detects a distance dz in the depth direction (Z coordinate direction) between the stereo camera 102 and the eyes of the subject as the distance between the imaging unit (stereo camera 102) and the eye positions of the subject.

Figure 4:
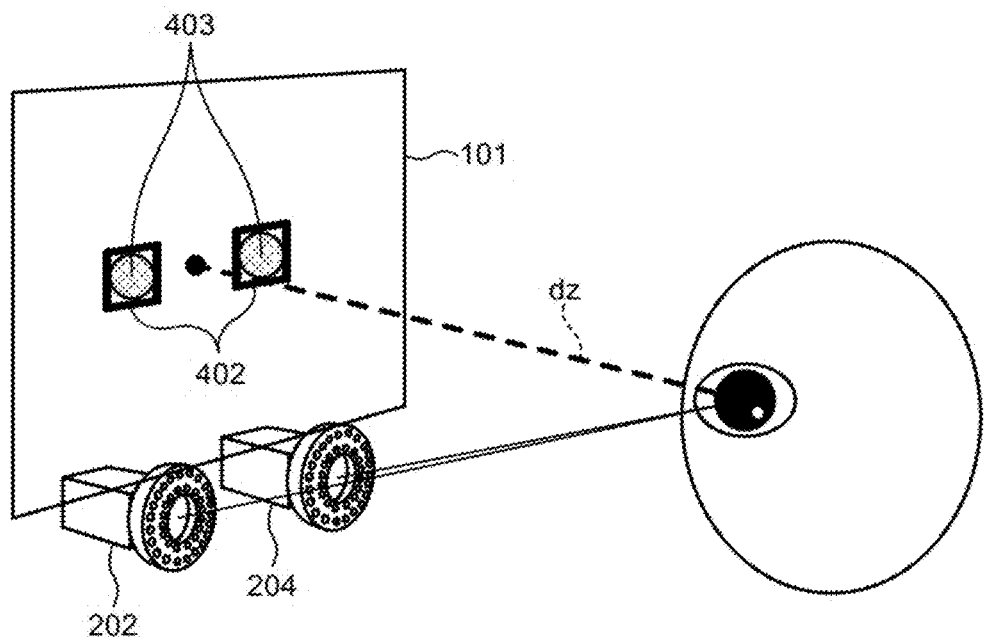
FIG. 4 is a diagram of exemplary detection of eyes and a distance in a case where two cameras are used.

FIG. 4 is a diagram of an exemplary detection of the eyes and the distance in a case where the two cameras (right camera 202 and left camera 204) are used. Regarding the two cameras, camera parameters are previously obtained by applying a camera calibration theory according to a stereo calibration method. As the stereo calibration method, all the methods, which have been conventionally used, such as a method using the Tsai's camera calibration theory can be applied. A three-dimensional coordinate of the eyes in the world coordinate system can be obtained by using the eye position detected from the image taken by the right camera 202, the eye position detected from the image taken by the left camera 204, and the camera parameter. Accordingly, the distance between the eyes and the stereo camera 102 and a pupil coordinate can be estimated. The pupil coordinate is a coordinate value which expresses the positions of the eyes (pupil) of the subject on the XY plane. The pupil coordinate can be, for example, a coordinate value in which the eye position expressed by the world coordinate system is projected on the XY plane. The pupil coordinates of the right and left eyes are usually obtained.

A marker 402 and eye position images 403 are displayed on the display screen 101. The eye position image 403 is an image indicating the eye position of the subject. The marker 402 is an image corresponding to the size of the eye position image 403 of the subject in a predetermined reference distance. A rectangular marker is illustrated in FIG. 4. However, the shape of the marker 402 is not limited to a rectangle. For example, a marker having a polygonal shape, a circular shape, or an elliptical shape other than the rectangle shape may be used.

When the coordinate system (world coordinate system) illustrated in FIG. 1 is used, the central position of the display screen 101 is the origin. Therefore, the Z coordinate value of the detected eye position corresponds to the distance dz between the stereo camera 102 and the eyes of the subject in the depth direction. The distance between the stereo camera 102 and the subject may be calculated from the actual position of the stereo camera 102 and the eye position of the subject calculated by the line of sight detecting unit 351. For example, the point of view detecting unit 352 may detect a distance between the eyes of the subject and one of the positions of the right camera 202 and the left camera 204 or an intermediate position between the positions of the right camera 202 and the left camera 204.

The description returns to FIG. 3. The output controller 354 controls output of various information relative to the display 210, the speaker 105, the printer 324, and the like. The output controller 354 controls the output relative to the display 210. For example, the output is an image used to calibrate a parameter to detect the line of sight direction (first image), an image used to detect the point of regard for correction to correct the position of the point of regard (second image), an image used for the diagnosis (diagnostic image (third image)), and an evaluation result by the evaluation unit 359.

As described below, the output controller 354 may control the image to be used to calibrate, the image to be used to detect the point of regard for correction, and the diagnostic image so as to display these images on the display 210 in this order. Accordingly, each processing necessary for the diagnosis can be smoothly performed, and the diagnosis accuracy can be improved.

Also, the output controller 354 displays an image to adjust the position of the subject (position adjusting image) on the display 210. For example, the output controller 354 displays at least one of the eye position image of the subject, the reference image indicating a range of a reference region, and an imaging range image indicating a range of an imaging region as the position adjusting image on the display screen 101. The output controller 354 changes display modes of the above three images according to the positional relationship between a set region and the eye position of the subject. The output controller 354 displays the images on the display screen 101, for example, by changing the sizes of the eye position images 403 according to the distance. The display mode is not limited to the size. For example, the display mode may be a color, a color tone of the image, the brightness of the image, and letters, symbols, or graphics included in the image.

The reference region is a region included in the imaging region. For example, the reference region is previously determined as a region indicating a range of an appropriate eye position of the subject. For example, a region with a predetermined size within the imaging region including the center of the imaging region can be the reference region. The set region is an appropriate region to detect the eye position of the subject. For example, the reference region and the imaging region may be the set region.

The reference image is an image displayed on the display screen 101 as the image indicating a range corresponding to the reference region. The reference image is displayed, for example, in the center part of the display screen 101. The output controller 354 displays the reference image on the display screen 101, for example, while changing the color of the reference image according to the positional relationship. The display mode is not limited to the color, and the brightness and the like may be changed.

The output controller 354 may display the moving image in the reference image. For example, an image in which a character shaped like a human and an animal moves can be used as the moving image. By using this, the subject is made to pay attention to the display screen 101, and the position of the subject can be appropriately adjusted.

Also, the output controller 354 displays a mark of a target point of regard position (target point) used to correct the point of regard position on the display screen 101. Here, the target point is a position where the subject regards.

Figure 5:
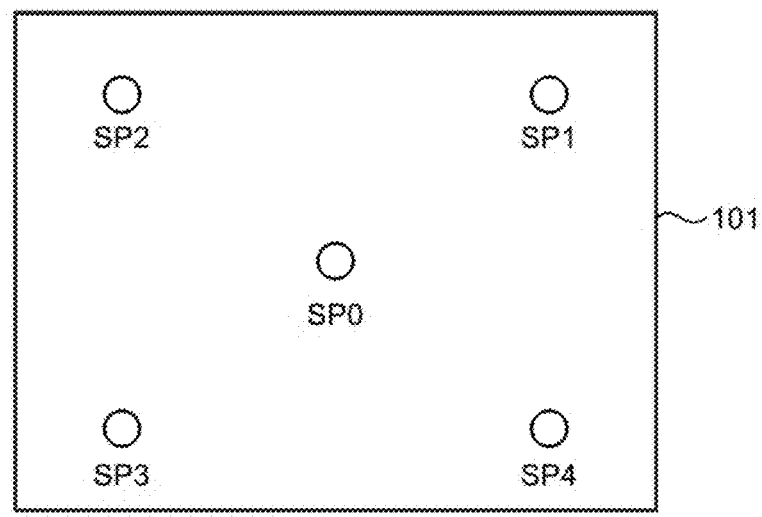
FIG. 5 is a diagram of an exemplary mark of a target point.

FIG. 5 is a diagram of an exemplary mark of the target point. As illustrated in FIG. 5, an image of a circle having a predetermined radius may be used as the mark. Also, a frame having a predetermined shape and an image displayed in the frame (still image and moving image) may be used as the mark. In the present embodiment, the output controller 354 displays five marks (SP0 to SP4) on the display 210. The five marks respectively indicate five different target points in the display region. The shapes and the number of the marks are not limited to them.

In the present embodiment, it is assumed that vertex positions of a quadrangle having four sides parallel to each side of the rectangular screen (display region) be the target points SP1 to SP4. Also, it is assumed that the target point SP0 be located approximately at the center of the screen. That is, SP0 is a center mark indicating an inner position of the marks SP1 to SP4 in the display region. In the present embodiment, it is assumed that SP0 correspond to the origin of the XYZ coordinate system, that is, the central position of the screen of the display 210. It is assumed that a kind and a display position of the image of the mark of the target point be previously set in the storage unit 150 and the like.

It is preferable that the mark of the target point be an image having different brightness and saturation from that of the other region on the display 210. The mark may be an image other than a circular image. Also, as another example, the mark of the target point may be indicated by irradiating the arrangement position of the target point with the light. That is, the mark may be the light as an alternative to the image. In this way, it is preferable that the mark be a mode with which the subject can recognize the position to be regard. The display mode is not limited to the embodiment.

The description returns to FIG. 3. The calibration unit 355 calibrates a calculation parameter used to detect the line of sight direction (calibration for detecting the line of sight). The optical axes of the eyes and the line of sight direction are generally different from one another. Therefore, it is necessary to correct the optical axis and the line of sight direction so as to correspond to one another. In calibration processing for detecting the line of sight, the subject is made to regard a predetermined position (for example, an image used for the calibration for detecting the line of sight) which has been known in the predetermined coordinate system.

Then, the center of the pupil (pupil position) and the corneal reflex position at that time are measured. The calibration unit 355 corrects the calculation parameter to detect the line of sight so that the line of sight direction is directed to a predetermined position. The line of sight direction is obtained from the measured pupil position and corneal reflex position.

The region dividing unit 356 divides the screen of the display 210 into a plurality of partial regions based on the point of regard detected relative to the mark of the target point displayed for the correction (point of regard for correction).

The region specifying unit 357 specifies the partial region in the display region to which the point of regard detected relative to the diagnostic image (point of regard for analysis) belongs.

The correction unit 358 corrects the position of the point of regard for analysis based on the partial region to which the point of regard for analysis belongs.

Here, processing of the region dividing unit 356, the region specifying unit 357, and the correction unit 358 will be described in detail with reference to FIGS. 6 to 9.

Figure 6:
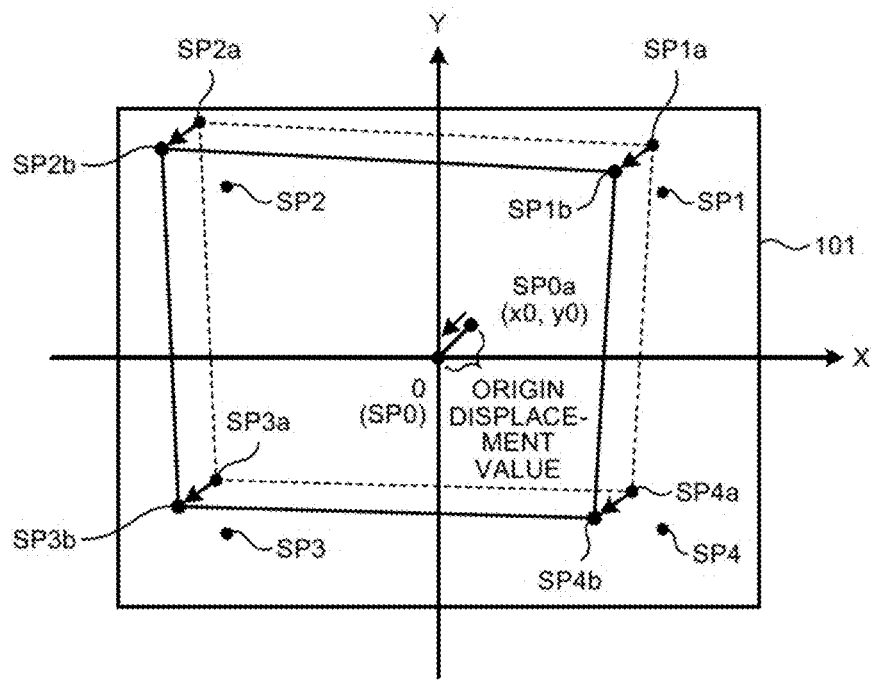
FIG. 6 is a diagram of SP0$a$ to SP4$a$.

The points SP0a to SP4a illustrated in FIG. 6 are the points of regard for correction of the subject. The subject regards the marks SP0 to SP4 of the target points so that the points of regard for correction are obtained.

First, the region dividing unit 356 conforms the point SP0a to the origin of the XY coordinate system. Specifically, the region dividing unit 356 calculates an origin displacement value from the origin to SP0a in the XY coordinate system. Here, the origin coincides with the position of SP0. The region dividing unit 356 obtains coordinates of SP1b to SP4b which are respectively moved from SP1a to SP4a by the origin displacement value. For example, when the coordinate of SP0a is (x0, y0), the origin displacement value becomes (−x0, −y0). Therefore, the region dividing unit 356 obtains the coordinates of SP1b to SP4b by respectively adding (−x0, −y0) to SP1a to SP4a.

Figure 7:
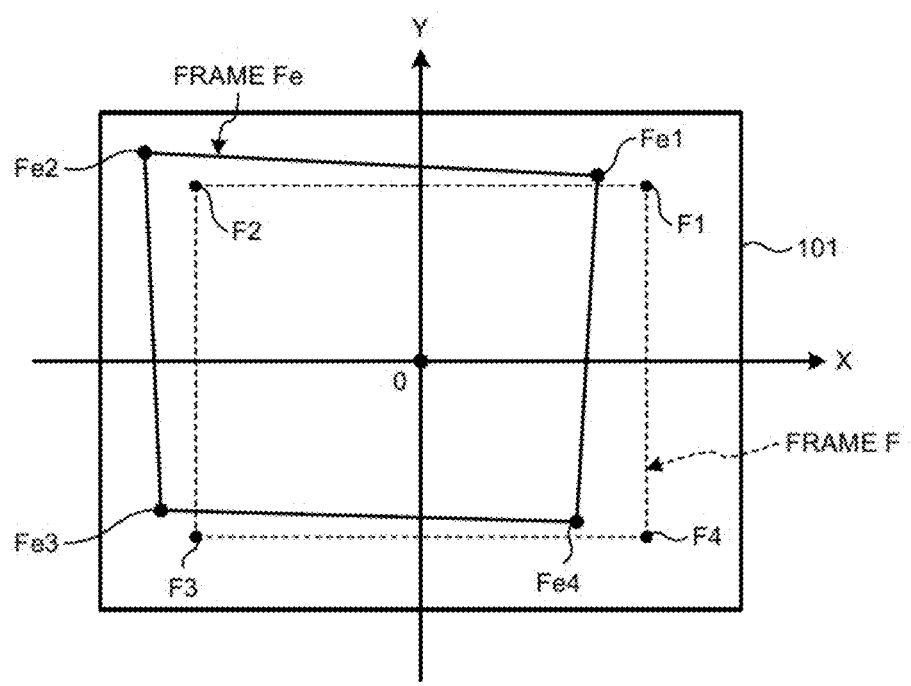
FIG. 7 is a diagram of frames F and Fe.

FIG. 7 is a diagram of a frame F and a frame Fe after the point SP0a in FIG. 6 has been moved to the origin of the XY coordinate system. The frame F is a frame determined by target points F1 to F4. The points F1 to F4 respectively correspond to the points SP1 to SP4. The frame Fe is a frame determined by points Fe1 to Fe4 corresponding to the points of regard for correction detected corresponding to the target points. The points Fe1 to Fe4 respectively correspond to the points SP1b to SP4b. That is, the frame F is a reference frame corresponding to the XY coordinate system on the display screen, and the frame Fe is an error frame including an error specific to each subject. The frames F and Fe are different concepts from the frames to be imaged by the right and left cameras (right camera 202 and left camera 204).

The point of regard for analysis calculated by the point of view detecting unit 352 is a point on the frame Fe. In addition, a degree of the error is different according to the line of sight direction, that is, the mark position due to an aspherical shape of an eyeball of the subject. In the diagnosis assisting apparatus 100 according to the present embodiment, the point of regard for analysis is corrected by dividing a target region into eight partial regions and converting the coordinate value on the frame Fe of the point of regard for analysis into the coordinate value on the frame F in each partial region.

Figure 8:
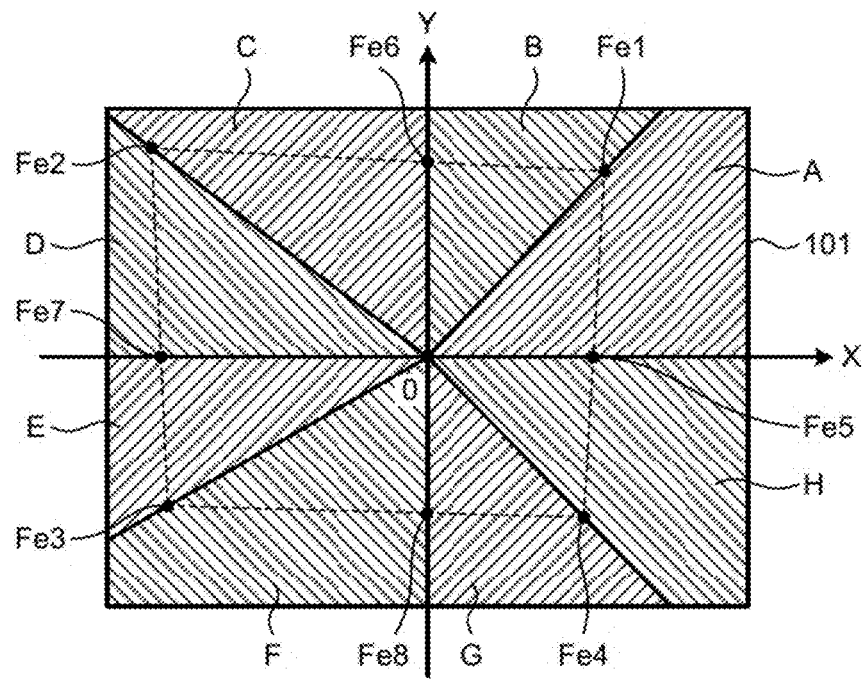
FIG. 8 is a diagram of a partial region of the frame Fe.

The region dividing unit 356 divides the target region into eight partial regions based on the positions of the points Fe1 to Fe4. FIG. 8 is a diagram of the eight partial regions. Each partial region is a region determined by the origin O, the points Fe1 to Fe4, the X-axis, and the Y-axis. Here, the points Fe1 to Fe4 respectively correspond to SP1b to SP4b. The points SP1b to SP4b are respectively determined based on SP1a to SP4a. That is, the region dividing unit 356 divides the target region into the eight partial regions based on the positions of SP1a to SP4a.

Here, an intersection point between a line passing through the points Fe1 and Fe4 and the X-axis is a point Fe5. An intersection point between a line passing through the points Fe1 and Fe2 and the Y-axis is a point Fe6. An intersection point between a line passing through the points Fe2 and Fe3 and the X-axis is a point Fe7. An intersection point between a line passing through the points Fe3 and Fe4 and the Y-axis is a point Fe8.

The region dividing unit 356 divides the target region into the eight partial regions illustrated in FIG. 8, i.e., a first quadrant lower region A, a first quadrant upper region B, a second quadrant upper region C, a second quadrant lower region D, a third quadrant upper region E, a third quadrant lower region F, a fourth quadrant lower region G, and a fourth quadrant upper region H. Also, the region specifying unit 357 specifies the partial region of the eight partial regions to which the point of regard for analysis detected by the point of view detecting unit 352 belongs based on the coordinate of the point of regard for analysis and the positions of the eight partial regions divided by the region dividing unit 356.

Here, the first quadrant lower region A has a line passing through the origin O and the point Fe1 and a line passing through the origin O and the point Fe5 (X-axis) as boundary positions. The first quadrant upper region B has a line passing through the origin O and the point Fe1 and a line passing through the origin O and the point Fe6 (Y-axis) as the boundary positions.

The second quadrant upper region C has a line passing through the origin O and the point Fe2 and a line passing through the origin O and the point Fe6 (Y-axis) as the boundary positions. The second quadrant lower region D has a line passing through the origin O and the point Fe2 and a line passing through the origin O and the point Fe7 (X-axis) as the boundary positions.

The third quadrant upper region E has a line passing through the origin O and the point Fe3 and a line passing through the origin O and the point Fe7 (X-axis) as the boundary positions. The third quadrant lower region F has a line passing through the origin O and the point Fe3 and a line passing through the origin O and the point Fe8 (Y-axis) as the boundary positions.

The fourth quadrant lower region G has a line passing through the origin O and the point Fe4 and a line passing through the origin O and the point Fe8 (Y-axis) as the boundary positions. The fourth quadrant upper region H has a line passing through the origin O and the point Fe4 and a line passing through the origin O and the point Fe5 (X-axis) as the boundary positions.

Figure 9:
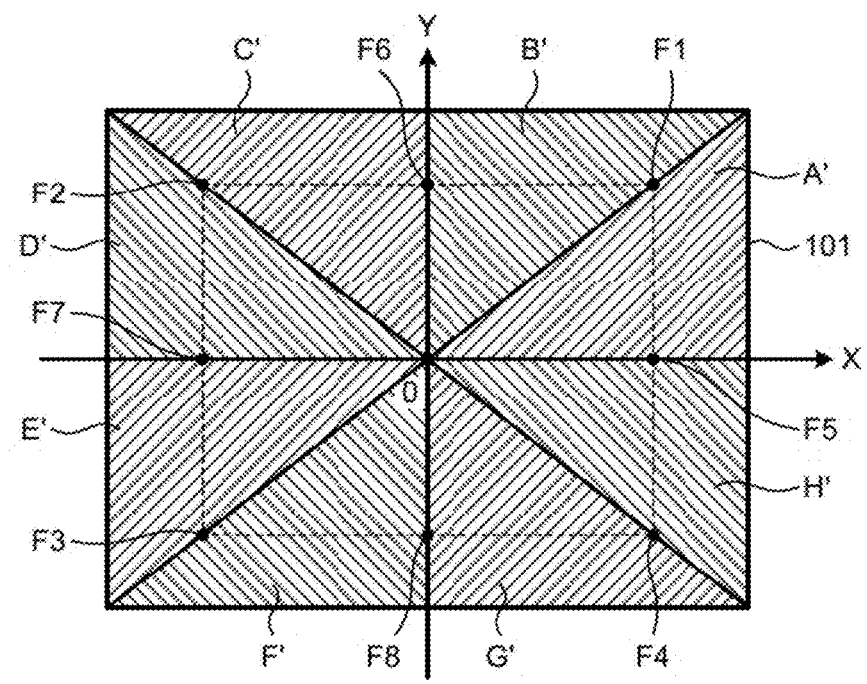
FIG. 9 is a diagram of a partial region of the frame F.

FIG. 9 is a diagram of partial regions (A' to H') of the frame F respectively corresponding to the first quadrant lower region A, the first quadrant upper region B, the second quadrant upper region C, the second quadrant lower region D, the third quadrant upper region E, the third quadrant lower region F, the fourth quadrant lower region G, and the fourth quadrant upper region H.

The first quadrant lower region A', the first quadrant upper region B', the second quadrant upper region C', the second quadrant lower region D', the third quadrant upper region E', the third quadrant lower region F', the fourth quadrant lower region G', and the fourth quadrant upper region H' respectively correspond to the first quadrant lower region A, the first quadrant upper region B, the second quadrant upper region C, the second quadrant lower region D, the third quadrant upper region E, the third quadrant lower region F, the fourth quadrant lower region G, and the fourth quadrant upper region H.

The region specifying unit 357 specifies the partial region on the frame Fe to which the point of regard for analysis belongs as described above. In addition, the region specifying unit 357 specifies the partial region on the frame F which corresponds to the specified partial region on the frame Fe. For example, when the first quadrant lower region A on the frame Fe is specified, the first quadrant lower region A' on the frame F is specified as the corresponding partial region. That is, the region specifying unit 357 specifies the partial region on the frame Fe and the partial region on the frame F corresponding to the region on the frame Fe. The region specifying unit 357 corresponds to first and second partial region specifying units.

The partial regions on the frame F will be described with reference to FIG. 9. An intersection point between a line passing through the points F1 and F4 and the X-axis is a point F5. An intersection point between a line passing through the points F1 and F2 and the Y-axis is a point F6. An intersection point between a line passing through the points F2 and F3 and the X-axis is a point F7. An intersection point between a line passing through the points F3 and F4 and the Y-axis is a point F8.

The first quadrant lower region A' has a line passing through the origin O and the point F1 and a line passing through the origin O and the point F5 (X-axis) as the boundary positions. The first quadrant upper region B' has a line passing through the origin O and the point F1 and a line passing through the origin O and the point F6 (Y-axis) as the boundary positions.

The second quadrant upper region C' has a line passing through the origin O and the point F2 and a line passing through the origin O and the point F6 (Y-axis) as the boundary positions. The second quadrant lower region D' has a line passing through the origin O and the point F2 and a line passing through the origin O and the point F7 (X-axis) as the boundary positions.

The third quadrant upper region E' has a line passing through the origin O and the point F3 and a line passing through the origin O and the point F7 (X-axis) as the boundary positions. The third quadrant lower region F' has a line passing through the origin O and the point F3 and a line passing through the origin O and the point F8 (Y-axis) as the boundary positions.

The fourth quadrant lower region G' has a line passing through the origin O and the point F4 and a line passing through the origin O and the point F8 (Y-axis) as the boundary positions. The fourth quadrant upper region H' has a line passing through the origin O and the point F4 and a line passing through the origin O and the point F5 (X-axis) as the boundary positions.

The correction unit 358 corrects the position of the point of regard based on a correlation between the partial region on the frame Fe and the corresponding partial region on the frame F, that is, the displacement value from the frame Fe to the frame F.

Figure 10:
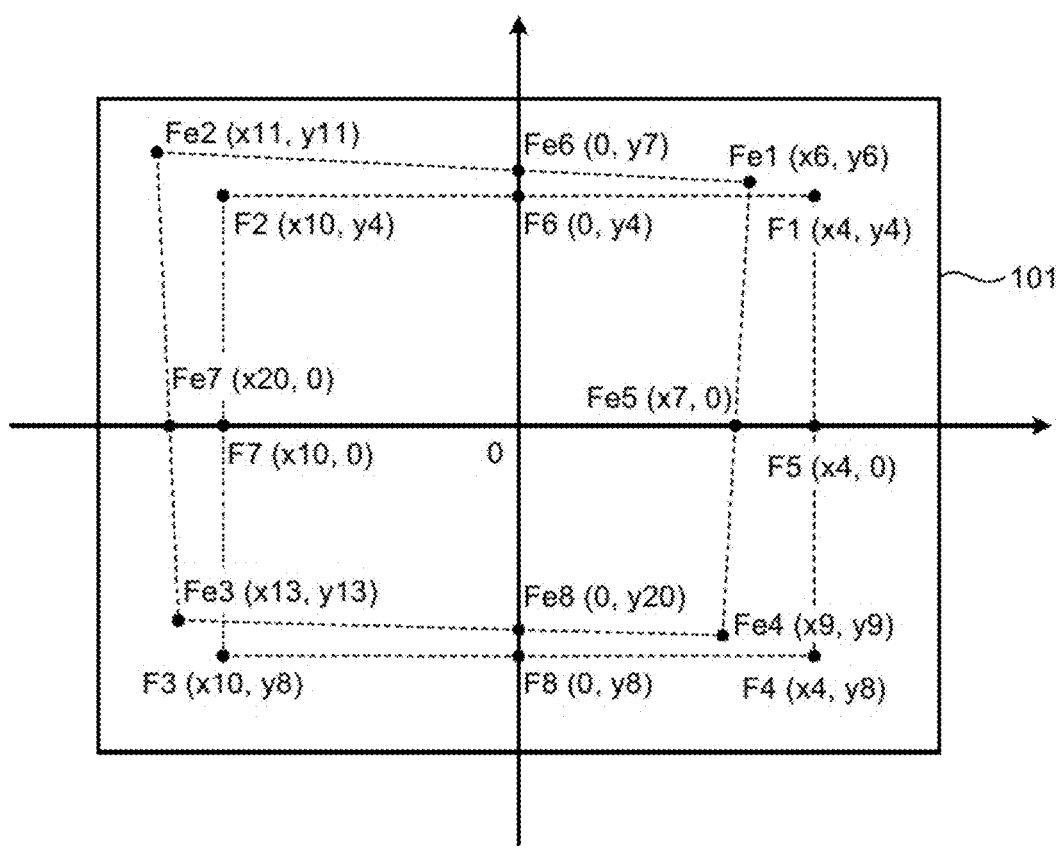
FIG. 10 is a diagram of coordinates of each point.

Processing by the correction unit 358 will be described in detail below with reference to FIGS. 10 to 14. FIG. 10 is a diagram of coordinates of the respective points. As illustrated in FIG. 10, a coordinate of the point F1 is (x4, y4), and a coordinate of the point F2 is (x10, y4). A coordinate of the point F3 is (x10, y8), and a coordinate of the point F4 is (x4, y8). A coordinate of the point F5 is (x4, 0), and a coordinate of the point F6 is (0, y4). A coordinate of the point F7 is (x10, 0), and a coordinate of the point F8 is (0, y8). Also, a coordinate of the point Fe1 is (x6, y6), and a coordinate of the point Fe2 is (x11, y11). A coordinate of the point Fe3 is (x13, y13), and a coordinate of the point Fe4 is (x9, y9). A coordinate of the point Fe5 is (x7, 0), and a coordinate of the point Fe6 is (0, y7). A coordinate of the point Fe7 is (x20, 0), and a coordinate of the point Fe8 is (0, y20).

Figure 11:
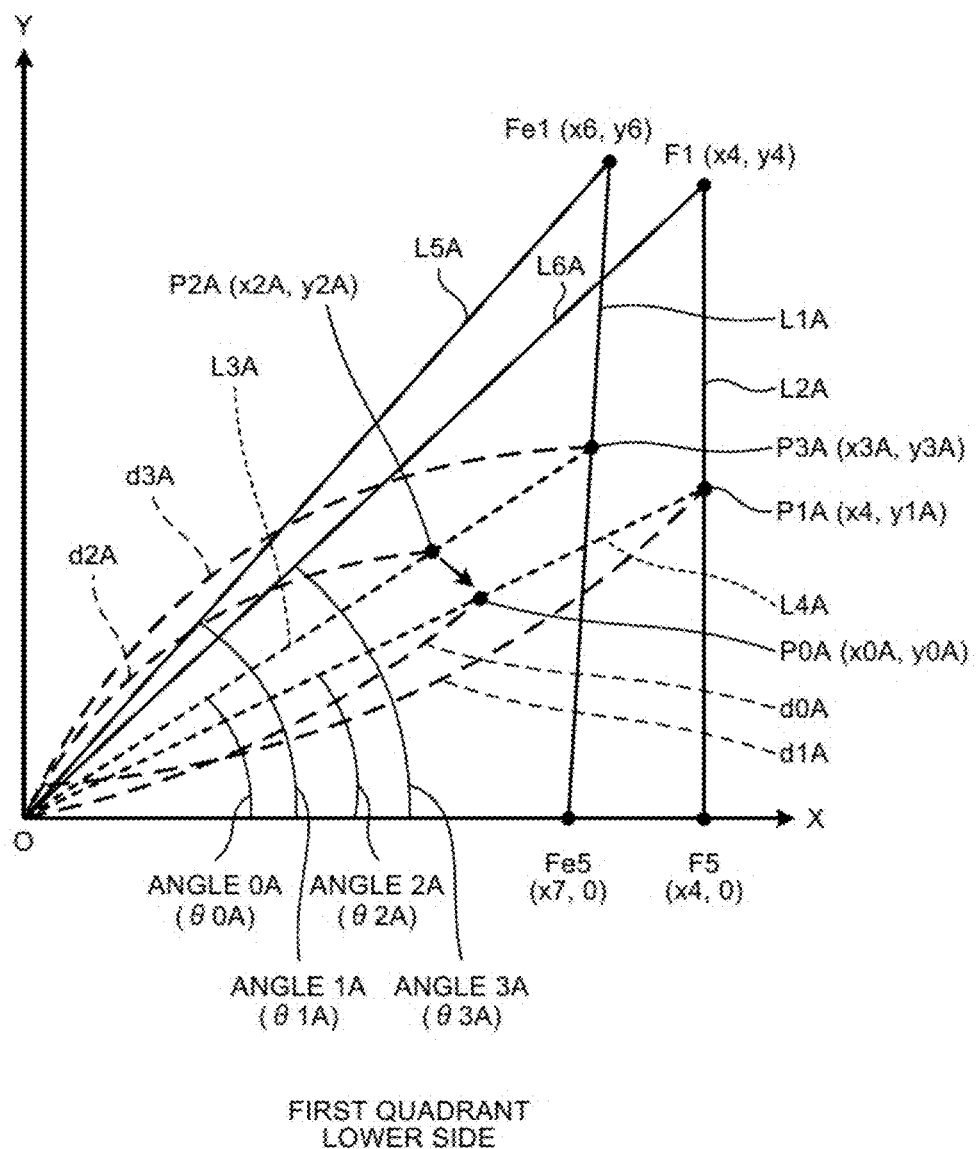
FIG. 11 is a diagram of a first quadrant lower region A.

In addition, as illustrated in FIG. 11, it is assumed that the point of regard for analysis detected in the first quadrant lower region A be a point P2A and a coordinate of the point P2A be (x2A, y2A). Also, it is assumed that the point of regard for analysis after the correction of the point P2A be a point P0A and a coordinate of the point P0A be (x0A, y0A).

In addition, it is assumed that a line passing through the points Fe1 and Fe5 be L1A and a line passing through the points F1 to F5 be L2A. It is assumed that a line passing through the point P2A and the origin O be L3A and a line passing through the point P0A and the origin be L4A. It is also assumed that a line passing through the point Fe1 and the origin be L5A and a line passing through the point F1 and the origin be L6A.

Also, it is assumed that an intersection point between the lines L2A and L4A be a point P1A and a coordinate of the point P1A be (x4, y1A). Also, it is assumed that an intersection point between the lines L1A and L3A be a point P3A and a coordinate of the point P3A be (x3A, y3A).

Also, it is assumed that a distance between the origin and the point P0A be d0A and a distance between the origin and the point P1A be d1A. It is assumed that a distance between the origin and the point P2A be d2A and a distance between the origin and the point P3A be d3A.

Also, it is assumed that an angle of an angle 0A formed by the line L3A and the X-axis be θ0A and an angle of an angle 1A formed by the line L5A and the X-axis be θ1A. It is assumed that an angle of an angle 2A formed by the line L4A and the X-axis be θ2A and an angle of an angle 3A formed by the line L6A and the X-axis be θ3A.

Under the above condition, the correction unit 358 obtains the angle θ2A of the angle 2A while assuming that a ratio of the angle θ0A of the angle 0A relative to the angle θ1A of the angle 1A is equal to a ratio of the angle θ2A of the angle 2A relative to the angle θ3A of the angle 3A. In addition, the correction unit 358 calculates the corrected position of the point of regard for correction by obtaining the distance d0A while assuming that a ratio of the distance d2A relative to the distance d3A is equal to a ratio of the distance d0A relative to the distance d1A.

First, the correction unit 358 calculates the angles θ0A, θ1A, and θ3A according to equations 1 to 3.

$$\theta 0A = \tan^{-1} \frac{y2A}{x2A} \quad (1)$$

$$\theta 1A = \tan^{-1} \frac{y6}{x6} \quad (2)$$

$$\theta 3A = \tan^{-1} \frac{y4}{x4} \quad (3)$$

Equation 4 is satisfied, because a ratio of the angle θ0A of the angle 0A relative to the angle θ1A of the angle 1A is equal to a ratio of the angle θ2A of the angle 2A relative to the angle θ3A of the angle 3A. The correction unit 358 calculates the angle θ2A by substituting the angles θ0A, θ1A, and θ3A calculated according to equations 1 to 3 in equation 4.

$$\theta 2A = \frac{\theta 0A}{\theta 1A} \cdot \theta 3A \quad (4)$$

The correction unit 358 also calculates the coordinate (x3A, y3A) of the point P3A by assuming that the point P3A is the intersection point between the lines L1A and L3A. Here, the line L1A is indicated by equation 5.

$$x = \frac{x6-x9}{y6-y9} y + x6 - y6 \frac{x6-x9}{y6-y9} \quad (5)$$

Equation 5 can be indicated as equation 6.

$$x = a1y + b1 \quad (6)$$

The references "a1" and "b1" in equation 6 can be respectively indicated by equations 7 and 8.

$$a1 = \frac{x6-x9}{y6-y9} \quad (7)$$

$$b1 = x6 - y9 \frac{x6-x9}{y6-y9} \quad (8)$$

Also, the line L3A is indicated by equation 9.

$$y = \frac{y2A}{x2A} x \quad (9)$$

Equations 10 and 11 are obtained by substituting equation 9 into equation 6.

$$x3A = \frac{b1}{1 - a1 \frac{y2A}{x2A}} \quad (10)$$

$$y3A = x3A \cdot \frac{y2A}{x2A} \quad (11)$$

The correction unit 358 calculates the coordinate (x3A, y3A) of the point P3A according to equations 10 and 11.

In addition, the correction unit 358 calculates a ratio k0 of the distance d2A relative to the distance d3A according to equation 12.

$$k0 = \frac{\sqrt{x2A^2 + y2A^2}}{\sqrt{x3A^2 + y3A^2}} \quad (12)$$

The correction unit 358 also calculates a coordinate (x4, y1A) of the point P1A. Here, the line L2A is indicated by equation 13.

$$x = x4 \quad (13)$$

Equations 14 and 15 can be obtained by using equation 13.

$$x1A = x4 \quad (14)$$

$$y1A = x1A \cdot \tan \theta 2A \quad (15)$$

The correction unit 358 calculates a coordinate (x4, y1A) of the point P1A according to equations 14 and 15 based on the above.

In addition, the correction unit 358 calculates the distance d1A according to equation 16.

$$d1A = \sqrt{x1A^2 + y1A^2} \quad (16)$$

The correction unit 358 assumes that the point P0A is a point having a ratio of the distance d0A relative to the distance d1A which becomes k0. The correction unit 358 calculates a coordinate (x0A, y0A) of the point P0A according to equations 17 and 18.

$$x0A = d1A \cdot k0 \cdot \cos \theta 2A \quad (17)$$

$$y0A = d1A \cdot k0 \cdot \sin \theta 2A \quad (18)$$

Also in the other partial region, the correction unit 358 corrects the position of the point of regard for analysis which belongs to each partial region according to a similar expression.

Figure 12:
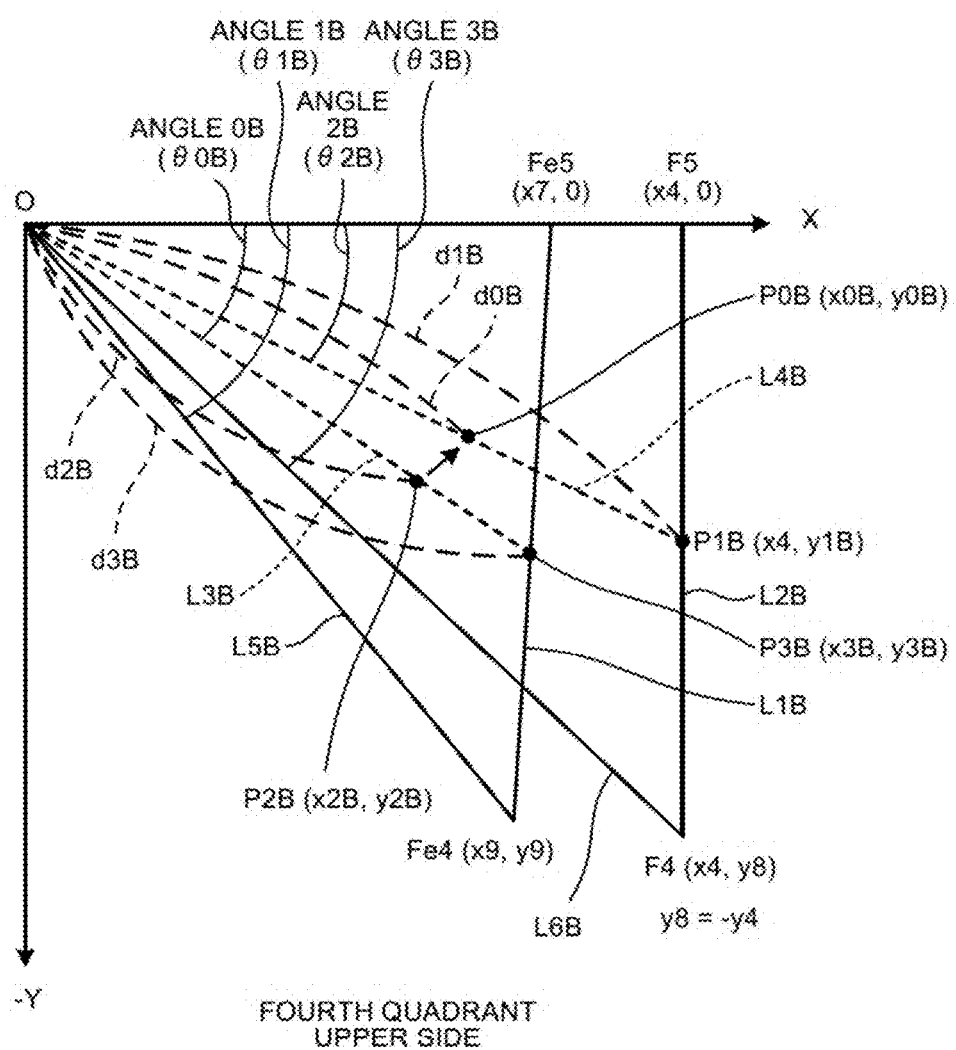
FIG. 12 is a diagram of a fourth quadrant upper region H.

FIG. 12 is a diagram of the fourth quadrant upper region H. When the point of regard for analysis belongs to the fourth quadrant upper region H, angles 0B to 3B are determined by using the X-axis as a reference. Also, lines L1B to L6B are determined. The correction unit 358 obtains an angle θ2B of the angle 2B while assuming that a ratio of an angle θ0B of the angle 0B relative to an angle θ1B of the angle 1B is equal to a ratio of the angle θ2B of the angle 2B relative to an angle θ3B of the angle 3B. In addition, the correction unit 358 obtains a distance d0B while assuming that a ratio of a distance d2B relative to a distance d3B is equal to a ratio of the distance d0B relative to a distance d1B. Accordingly, the correction unit 358 calculates a coordinate (x0B, y0B) of the point of regard for analysis P0B after the correction of the point of regard for analysis P2B (x2B, y2B).

Figure 13:
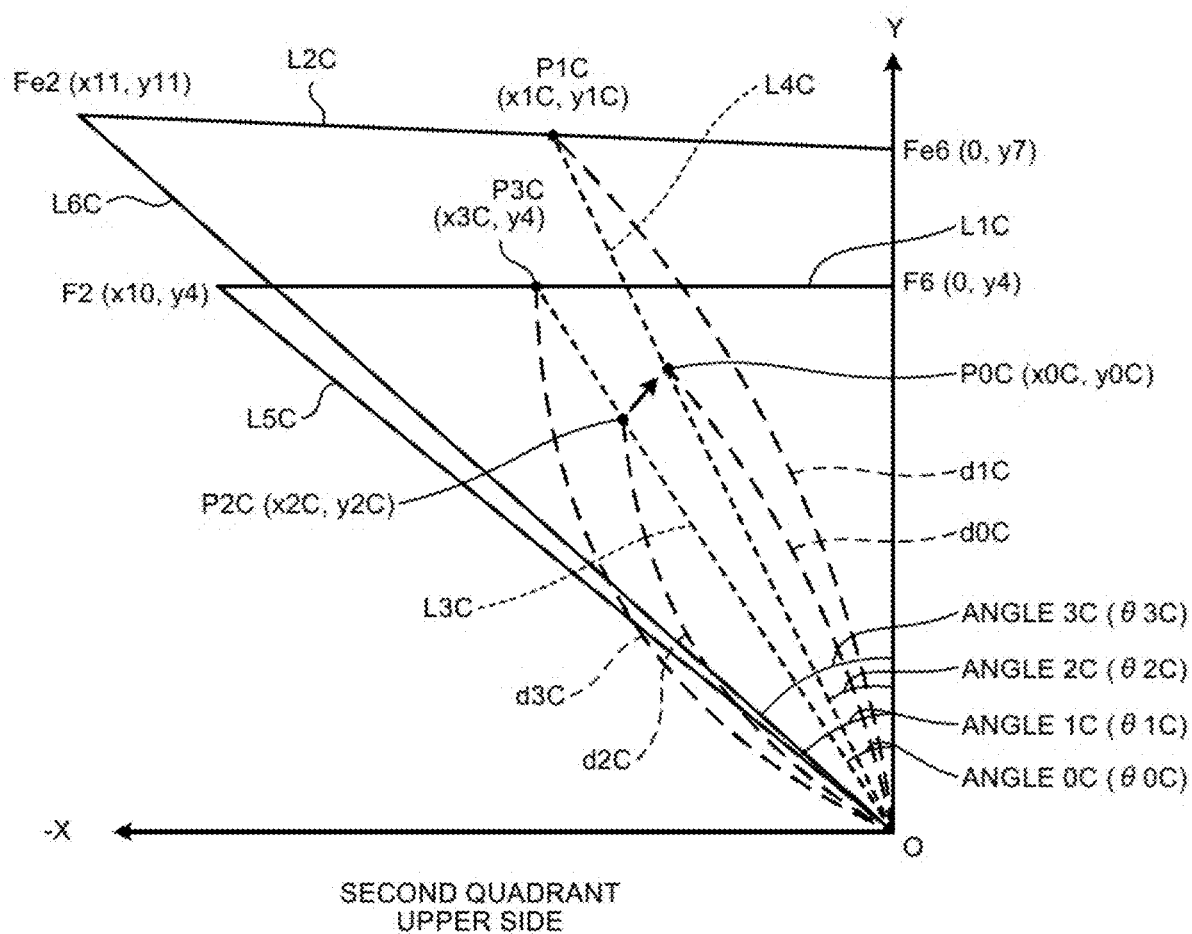
FIG. 13 is a diagram of a second quadrant upper region C.

FIG. 13 is a diagram of the second quadrant upper region C. When the point of regard for analysis belongs to the second quadrant upper region C, angles 0C to 3C are determined by using the Y-axis as a reference. Also, lines L1C to L6C are determined. The correction unit 358 obtains an angle θ2C of an angle 2C while assuming that a ratio of an angle θ0C of the angle 0C relative to an angle θ1C of the angle 1C is equal to a ratio of the angle θ2C of the angle 2C relative to an angle θ3C of the angle 3C. In addition, the correction unit 358 obtains a distance d0C while assuming that a ratio of a distance d2C relative to a distance d3C is equal to a ratio of the distance d0C relative to a distance d1C. Accordingly, the correction unit 358 calculates a coordinate (x0C, y0C) of the point of regard for analysis P0C after the correction of the point of regard for analysis P2C (x2C, y2C).

Figure 14:
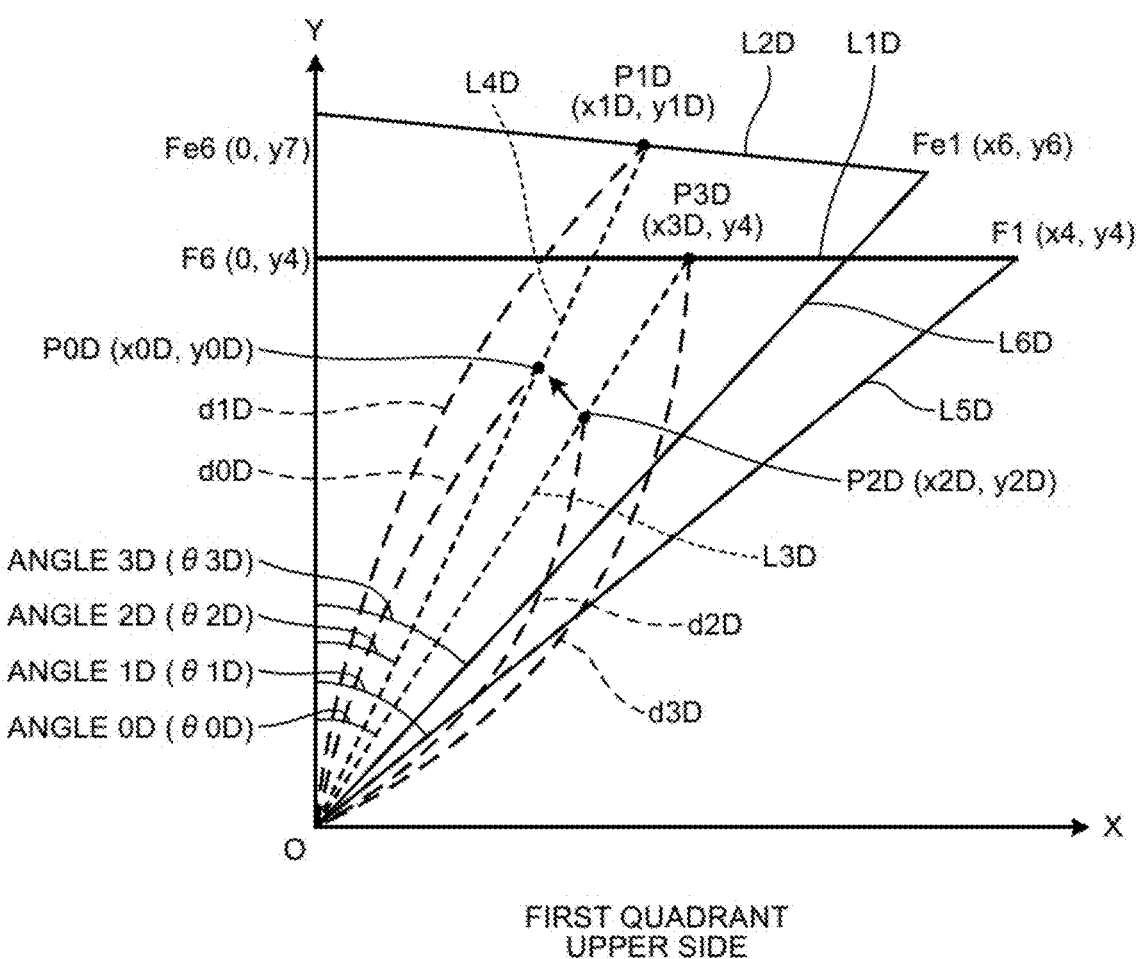
FIG. 14 is a diagram of a first quadrant upper region B.

FIG. 14 is a diagram of the first quadrant upper region B. When the point of regard for analysis belongs to the first quadrant upper region B, angles 0D to 3D are determined by using the Y-axis as a reference. Also, lines L1D to L6D are determined. The correction unit 358 obtains an angle θ2D of the angle 2D while assuming that a ratio of an angle θ0D of the angle 0D relative to an angle θ1D of the angle 1D is equal to a ratio of the angle θ2D of the angle 2D relative to an angle θ3D of the angle 3D. In addition, the correction unit 358 obtains a distance d0D while assuming that a ratio of a distance d2D relative to a distance d3D is equal to a ratio of the distance d0D relative to a distance d1D. Accordingly, the correction unit 358 calculates a coordinate (x0D, y0D) of the point of regard for analysis POD after the correction of the point of regard for analysis P2D (x2D, y2D).

The description returns to FIG. 3. The evaluation unit 359 calculates an evaluation value as an index regarding a degree of the developmental disorder based on the diagnostic image and the corrected point of regard for analysis. The evaluation unit 359 calculates a ratio in which the subject looks at the face image as the diagnostic image, for example, based on the positions of the points of regard for analysis of the subject in a case where the diagnostic images in FIGS. 39 to 44 to be described below are displayed as the evaluation value. As the evaluation value becomes lower, an evaluation value indicating that the possibility of the developmental disorder is high is calculated. It is preferable that the evaluation unit 359 calculate the evaluation value based on the diagnostic image and the point of regard for analysis. The calculation method is not limited to the embodiment.

Figure 15:
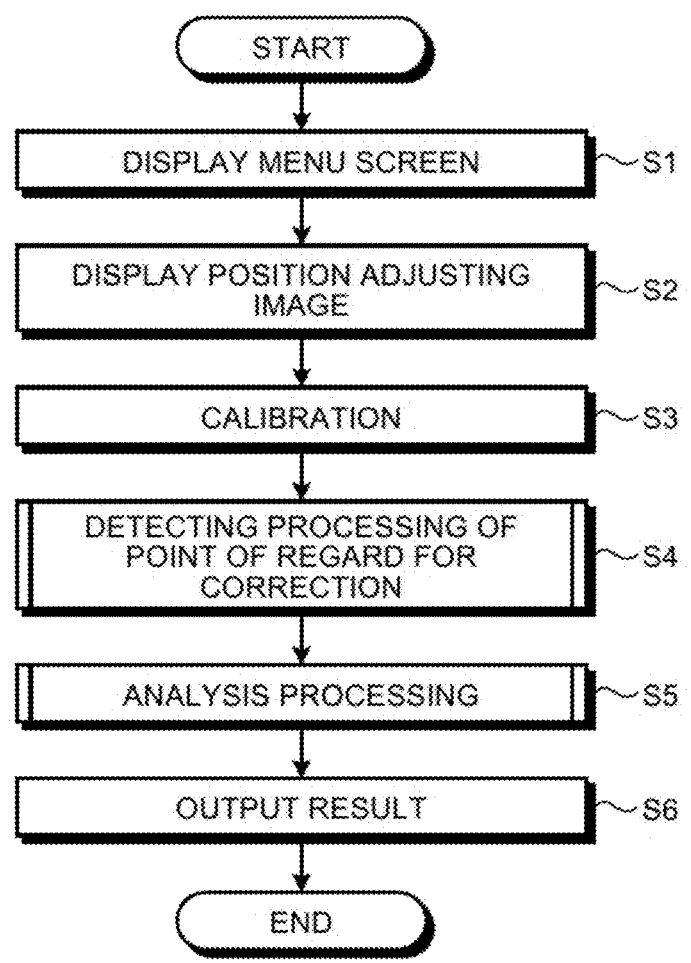
FIG. 15 is a flowchart of an exemplary diagnosis assisting process according to the first embodiment.

Next, a diagnosis assisting process by the diagnosis assisting apparatus 100 according to the first embodiment formed in this way will be described with reference to FIG. 15. FIG. 15 is a flowchart of an exemplary diagnosis assisting process according to the first embodiment.

Figure 16:
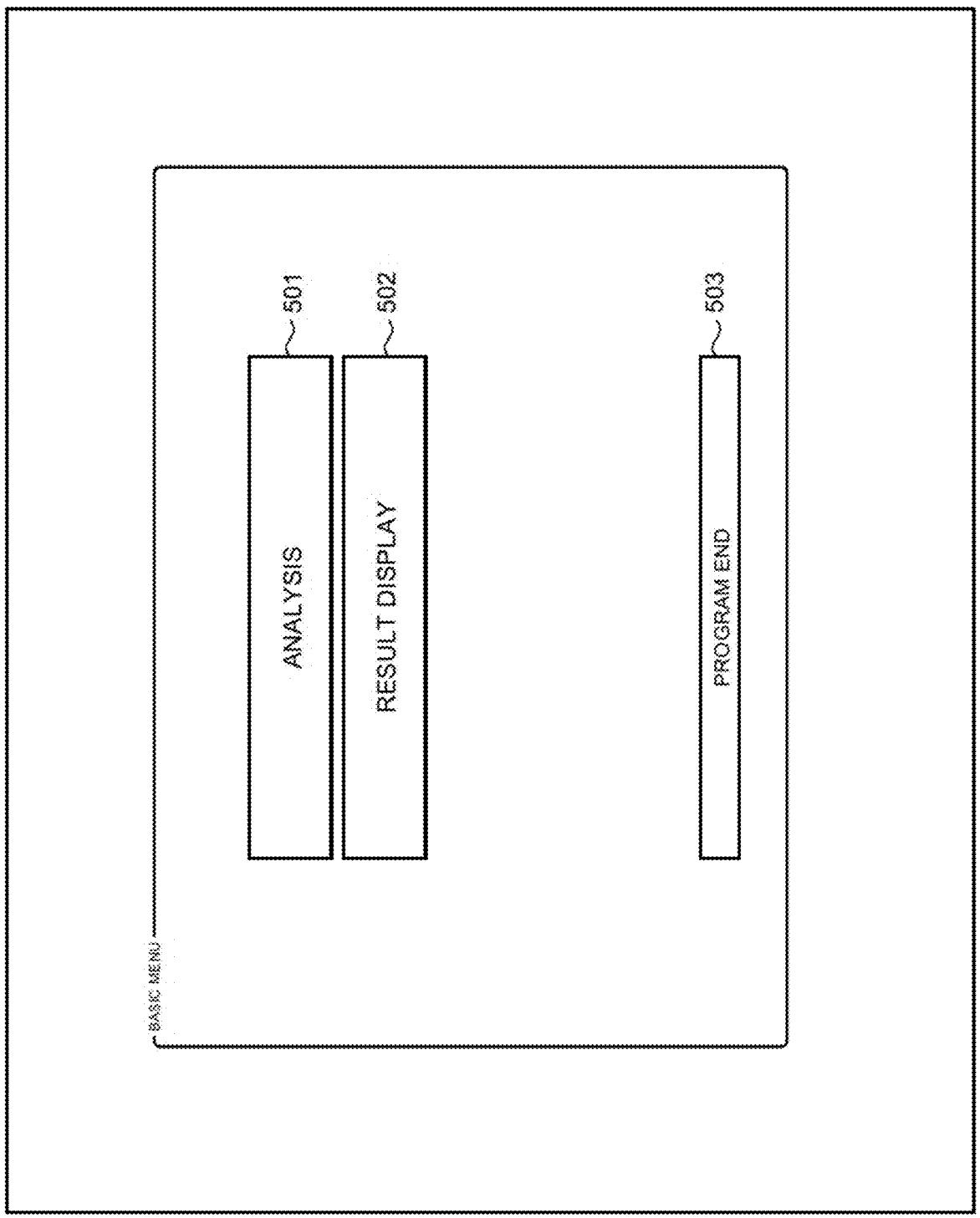
FIG. 16 is a diagram of an exemplary menu screen.

First, the output controller 354 displays a menu screen (step S1). FIG. 16 is a diagram of an exemplary menu screen. As illustrated in FIG. 16, the menu screen includes an analysis button 501, a result display button 502, and a program end button 503. When the analysis button 501 is pressed, the output controller 354 displays an analysis menu screen on the display 210. The analysis menu screen is a screen to perform analysis processing using the diagnostic image. When the result display button 502 is pressed, the output controller 354 displays a result display screen (to be described below) on the display 210. When the program end button 503 is pressed, the output controller 354 ends the diagnosis assisting process.

Figure 17:
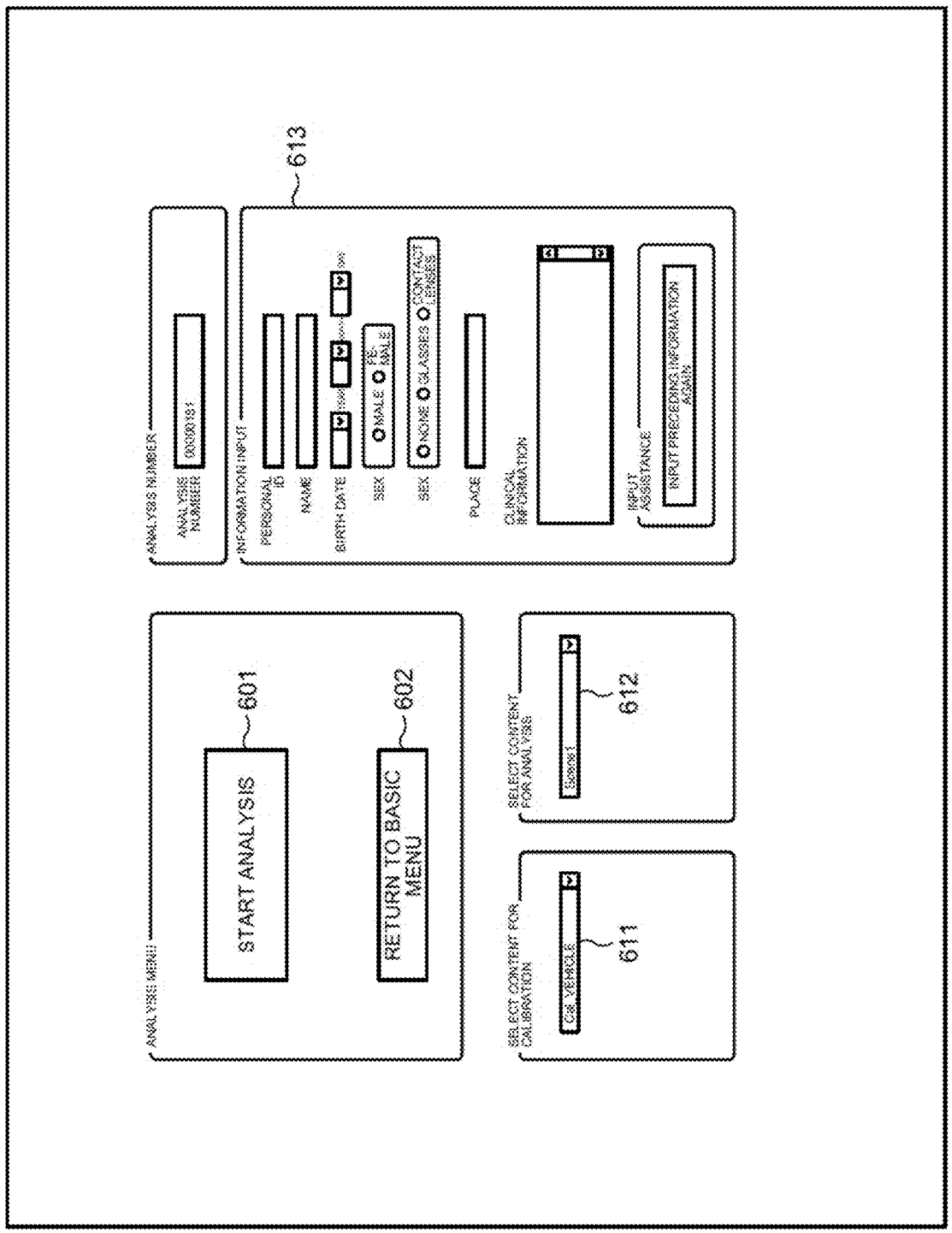
FIG. 17 is a diagram of an exemplary analysis menu screen.

FIG. 17 is a diagram of an exemplary analysis menu screen. As illustrated in FIG. 17, the analysis menu screen includes a "start analysis" button 601, a "return to basic menu" button 602, a pulldown 611 to select a content for the calibration, a pulldown 612 to select a content for the analysis, and an information input column 613.

Figure 21:
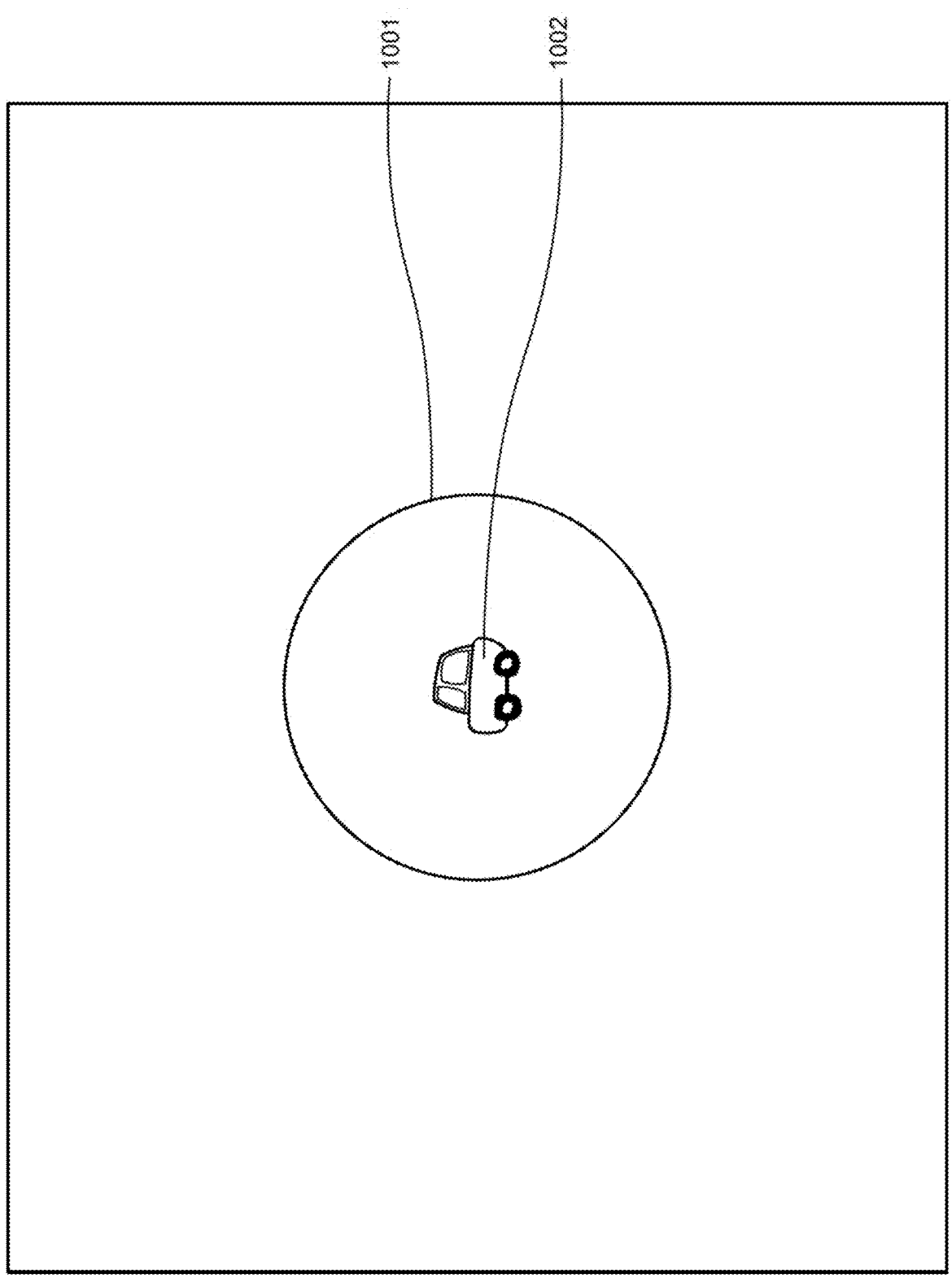
FIG. 21 is a diagram of an exemplary image for calibration.
Figure 22:
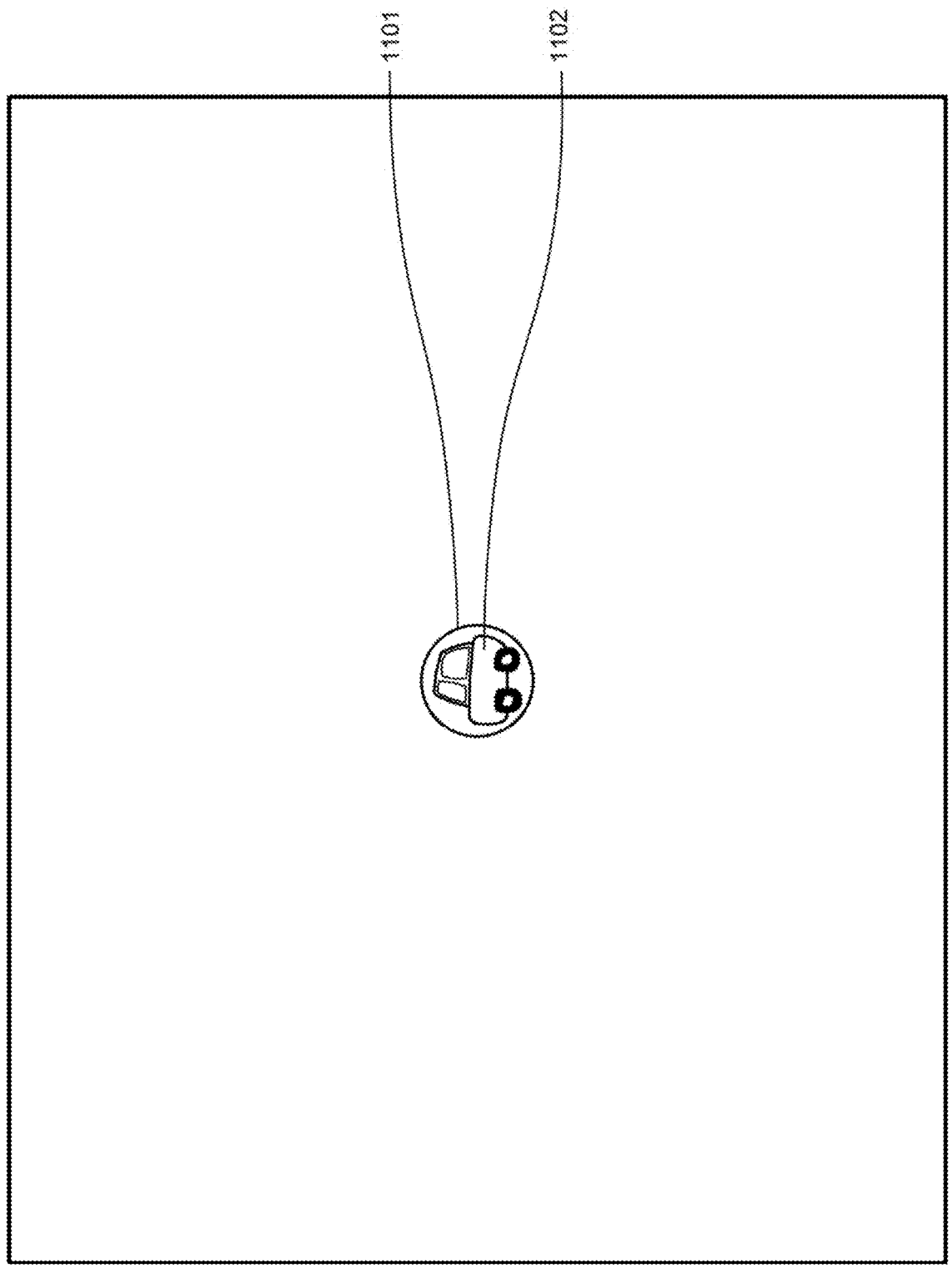
FIG. 22 is a diagram of an exemplary image for calibration.

When the "start analysis" button 601 is pressed, processing using the diagnostic image (processing in and after step S2 in FIG. 15) starts. When the "return to basic menu" button 602 is pressed, the display returns to the menu screen in FIG. 16. The content for the calibration indicates a content, for example, an image used for the calibration (calibration for detecting the line of sight) by the calibration unit 355. An exemplary content for the calibration is illustrated in FIGS. 21 and 22. A content selected by using the pulldown 611 is used for the calibration by the calibration unit 355. The content for the analysis indicates a content such as an image used for the diagnosis (diagnostic image). The content selected by using the pulldown 612 is used as the diagnostic image. The information input column 613 is a column to input various information necessary for the diagnosis such as information on the subject.

The description returns to FIG. 15. When the start of the analysis has been instructed, for example, when the analysis button 501 has been pressed on the menu screen and the "start analysis" button 601 has been pressed on the analysis menu screen, the output controller 354 displays the position adjusting image on the display 210 (step S2).

Figure 18:
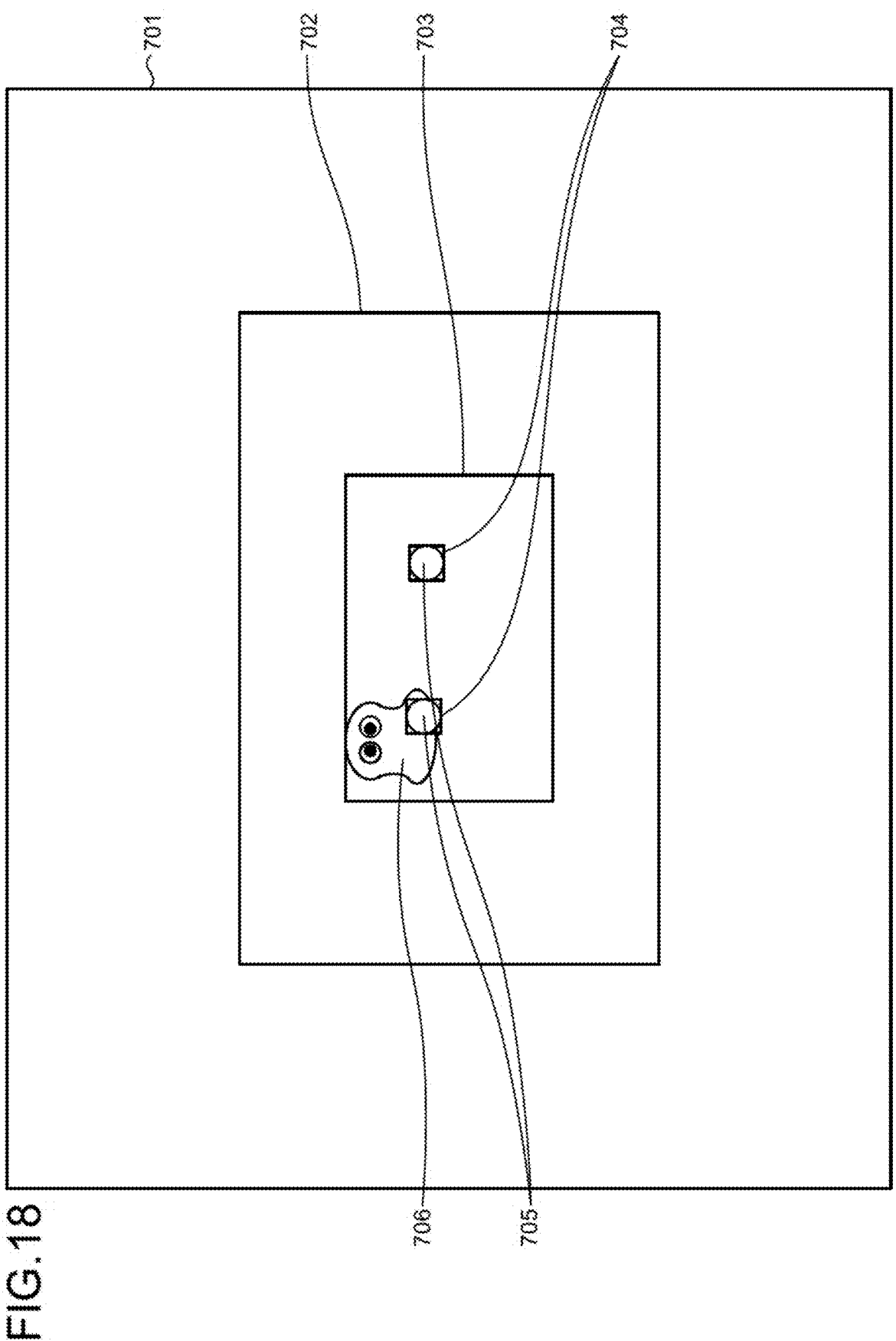
FIG. 18 is a diagram of an exemplary position adjusting image.

FIG. 18 is a diagram of an exemplary position adjusting image 701. The position adjusting image 701 includes a scale 703 as a reference image, a frame 702 as an imaging range image, eye position images 705, markers 704, and a character image 706. The character image 706 is a moving image. Since the subject is positioned in an appropriate distance in the example in FIG. 18, the images are displayed so that the diameter of the eye position image 705 coincides with the width of the marker 704. In this case, the output controller 354 may display, for example, the eye position image 705 in a color (for example, green) which indicates that the distance is appropriate. Also, since the subject exists within the reference region in the example in FIG. 18, the output controller 354 may display the scale 703 in a color (for example, green) which indicates that the subject is within the reference region. When detecting a situation where at least one of the right and left eye position images 705 of the subject is outside the reference region, the output controller 354 may display the scale 703 in a color (for example, red) which indicates that the eye position image 705 is outside the reference region. Also, when detecting a situation where at least one of the right and left eye position images 705 of the subject is outside the reference region, the output controller 354 may output the voice, such as "move rightward" or "move leftward". The output controller 354 moves the character image 706 in the scale 703 with time, and at the same time, the output controller 354 displays the character image 706 so as to change the eye position (direction of line of sight) and the shape. It is preferable that the moving image be an image, which attracts attention, other than the character image 706. For example, an image like fireworks and an image in which the brightness and the color change can be considered as the moving image.

In the present embodiment, the output controller 354 displays the character image 706 in the reference image (scale 703). This makes the subject pay attention to an appropriate position in the display screen 101.

Figure 19:
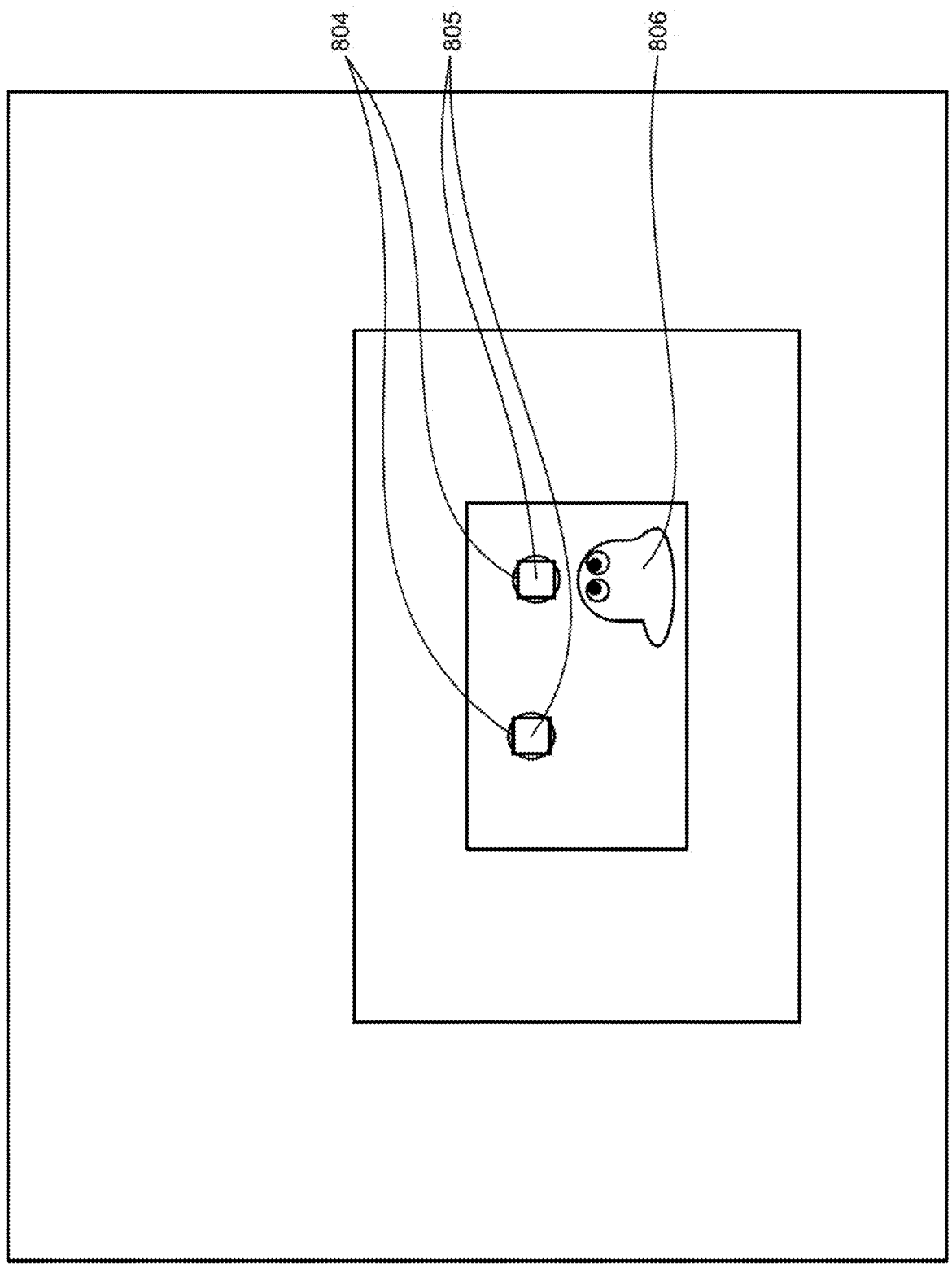
FIG. 19 is a diagram of another example of the position adjusting image.

FIG. 19 is a diagram of another example of the position adjusting image. For example, FIG. 19 is an example of the position adjusting image after time has been elapsed from the example in FIG. 18. Also, FIG. 19 is an example in which eye position images 805 are displayed larger than markers 804 because the eye positions of the subject has approached the stereo camera 102. In this case, the output controller 354 may display, for example, the eye position image 805 in a color (for example, red) which indicates that the distance is not appropriate. Also, when the eye position image 805 has been displayed larger than the marker 804, the output controller 354 may output the voice such as "move backward". Also, when the eye position image 805 has been displayed smaller than the marker 804, the output controller 354 may output the voice such as "move forward".

Figure 20:
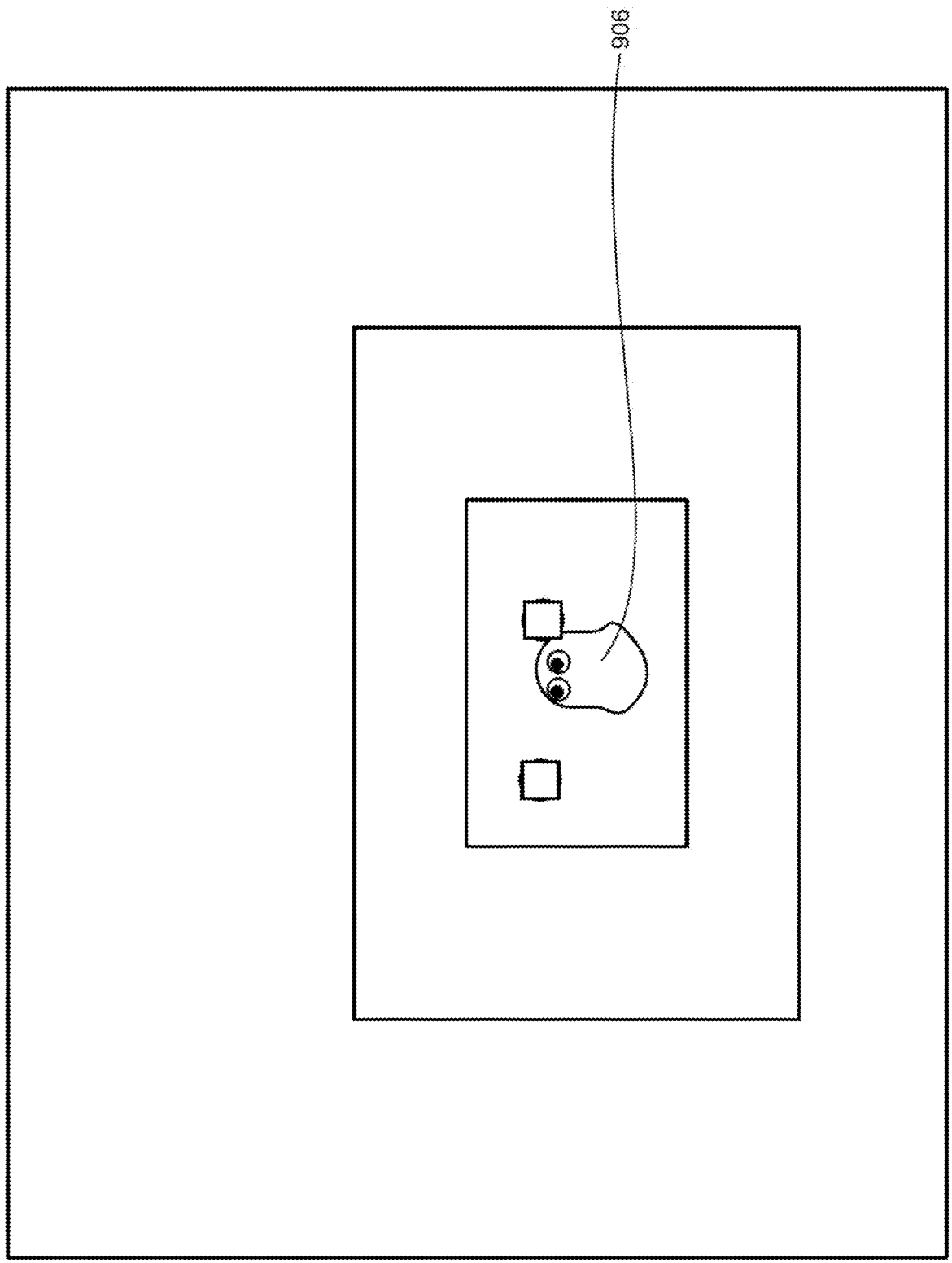
FIG. 20 is a diagram of a still another example of the position adjusting image.

FIG. 20 is a diagram of a still another example of position adjusting image. For example, FIG. 20 is an example of the position adjusting image after more time has been elapsed from the example in FIG. 19. As illustrated in FIGS. 19 and 20, the output controller 354 displays character images 806 and 906 which move in the reference image.

The description returns to FIG. 15. The position of the subject can be appropriately adjusted by displaying the position adjusting image in step S2. As a result, the subsequent processing can be performed with high accuracy. Next, the diagnosis assisting apparatus 100 performs the calibration to detect the line of sight (calibration for detecting line of sight) (step S3).

In the calibration processing, the output controller 354 displays an image for calibration (for example, content for the calibration selected by the pulldown 611 in FIG. 17) on the display 210 first.

FIGS. 21 and 22 are diagrams of exemplary images for calibration. First, the output controller 354 displays the image for calibration as illustrated in FIG. 21 on the display 210. The image for calibration includes a circular frame 1001 positioned around the center of the display screen 101 and an image 1002 of an object positioned around the center of the frame 1001. After displaying the image illustrated in FIG. 21 first, the output controller 354 displays the image while gradually reducing it toward the center of the frame 1001. FIG. 22 is an exemplary image for calibration displayed after reducing the image in this way. The image for calibration after the reduction includes a circular frame 1101 and an image 1102 of an object positioned around the center of the frame 1101. With the display of these images, the subject can pay attention to the position around the center of the display screen 101.

The calibration unit 355 calibrates the calculation parameter to detect the line of sight so that the line of sight direction detected by the line of sight detecting unit 351 is directed to the center of the display screen 101 while assuming that the subject regards the center of the display screen 101.

The description returns to FIG. 15. After the calibration in step S3, the diagnosis assisting apparatus 100 performs the detecting processing of point of regard for correction to correct the position of the point of regard for analysis (step S4). In the detecting processing of point of regard for correction, the diagnosis assisting apparatus 100 detects the point of regard relative to the mark indicating the target point, that is, the point of regard for correction. The detecting processing of point of regard for correction will be described below.

Next, the diagnosis assisting apparatus 100 performs the analysis processing using the diagnostic image (step S5). In the analysis processing, the output controller 354 displays the diagnostic image, and the point of view detecting unit 352 detects the point of regard for analysis. Also, after the correction unit 358 has corrected the position of the point of regard for analysis by using the point of regard for correction, the evaluation unit 359 calculates the evaluation value as an index regarding the degree of the developmental disorder by using the corrected point of regard for analysis. The analysis processing will be described in detail below. The diagnosis by a diagnosing person can be assisted, for example, by displaying the detection result of the point of regard for analysis as illustrated in FIGS. 50 to 54 without calculating the evaluation value by the evaluation unit 359.

Next, the output controller 354 outputs an analysis result (evaluation result) according to the analysis processing to the display 210 and the like (step S6). Processing for outputting the result will be described in detail below.

Figure 23:
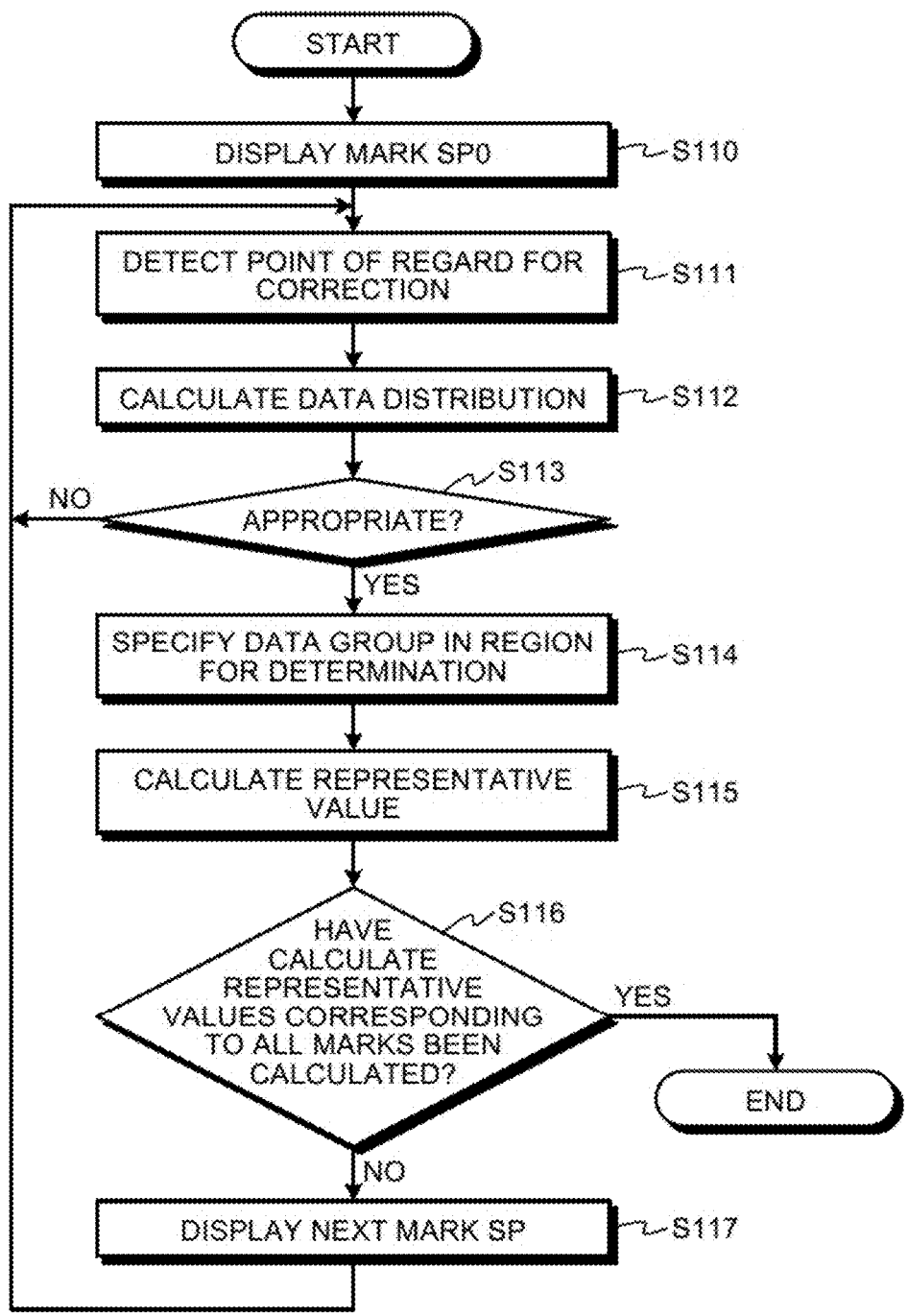
FIG. 23 is a flowchart of detailed detecting processing of point of regard for correction.

Next, the detecting processing of point of regard for correction in step S4 will be described in detail. FIG. 23 is a flowchart of an exemplary detecting processing of point of regard for correction according to the first embodiment.

In the detecting processing of point of regard for correction, the output controller 354 displays a mark SP0 indicating the target point at a predetermined position (origin position) first (step S110). Next, the point of view detecting unit 352 detects the position of the point of regard for correction obtained relative to the mark SP0 (step S111). The point of view detecting unit 352 detects a predetermined number of the points of regard for correction and calculates a data distribution of these (step S112).

Figure 24:
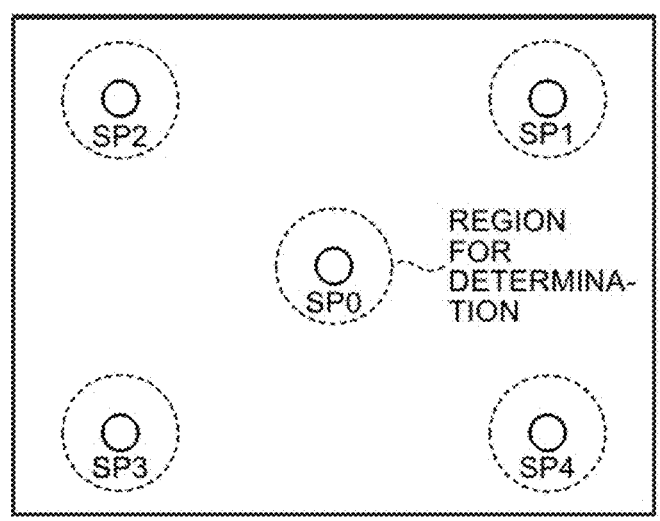
FIG. 24 is a diagram to describe calculation processing of data distribution.

FIG. 24 is a diagram to describe the calculation processing of the data distribution. Regions for determination having the marks (SP0 to SP4) as the centers are previously set relative to the respective marks. In the present embodiment, a circle having a predetermined radius and having the mark as the center is the region for determination. When equal to or more than the predetermined number of the points of regard for correction cannot be obtained in the region for determination, there is a high possibility that the subject has not carefully regarded the mark of the target point. Also, there is a possibility that the point of regard for correction effective to correct the point of regard has not been detected. In the present embodiment, the point of view detecting unit 352 determines whether the detected point of regard for correction is appropriate according to whether equal to or more than the predetermined number of the points of regard have been detected in the region for determination in a predetermined time when the mark is displayed.

In the data distribution calculation processing in step S112, the point of view detecting unit 352 measures the number of the points of regard for correction which belong to the region for determination. When the number of the points of regard for correction which belong the region for determination is equal to or more than a threshold which has been previously set, the point of view detecting unit 352 determines that the detected points of regard for correction are appropriate (step S113, Yes). Then, the point of view detecting unit 352 specifies a data group in the region for determination in which the points of regard for correction not belonging to the region for determination are removed from the detected plurality of points of regard for correction (step S114).

When it has been determined in step S113 that the points of regard for correction are not appropriate (step S113, No), the procedure returns to step S111. The point of view detecting unit 352 detects the point of regard for correction again.

Next, the point of view detecting unit 352 calculates a representative value of the data group in the region for determination based on the coordinate of each point of regard for correction of the data group in the region for determination (step S115). In the present embodiment, an average value of the data group in the region for determination is calculated as the representative value. The representative value may be a value other than the average value. The representative value may be, for example, a standard deviation. In the subsequent processing, the representative value calculated in step S115 is used as the point of regard for correction.

Next, when the representative value relative to the marks of all the target points is not calculated (step S116, No), the output controller 354 displays the mark indicating the next target point (step S117). The procedure returns to step S111. The representative value relative to the displayed marks is calculated (steps S111 to 115).

When the representative value relative to the marks of all the target points is calculated in step S116 (step S116, Yes), the detecting processing of point of regard for correction (step S4) is completed.

FIGS. 25A to 25E are diagrams to describe the display processing of the mark of each target point in the detecting processing of point of regard for correction (step S4). First, the output controller 354 displays a mark SP0 on the display 210 as illustrated in FIG. 25-A in step S110 illustrated in FIG. 23. Next, the output controller 354 displays the marks of other target points on the display 210 one by one in an order in step S117.

Figure 25A:
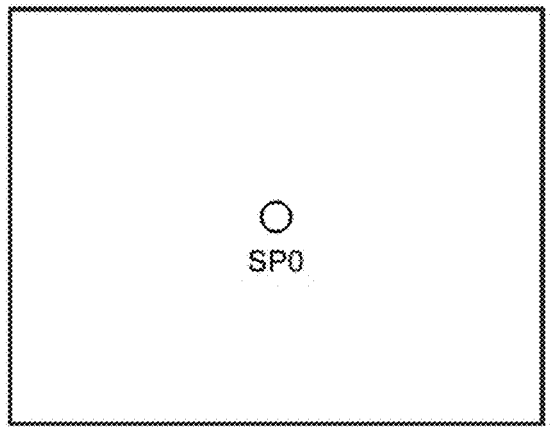
FIG. 25A is a diagram to describe display processing of the mark of the target point in the detecting processing of point of regard for correction.
Figure 25B:
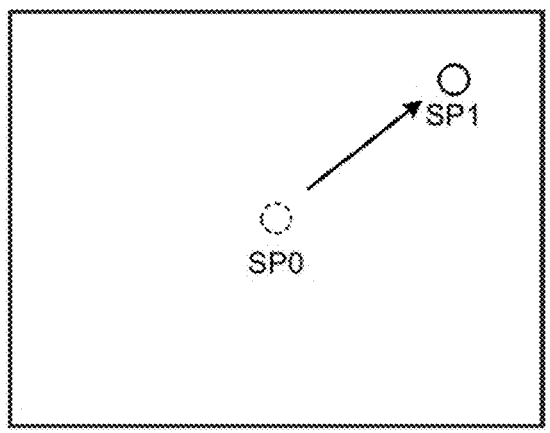
FIG. 25B is a diagram to describe the display processing of the mark of the target point in the detecting processing of point of regard for correction.
Figure 25C:
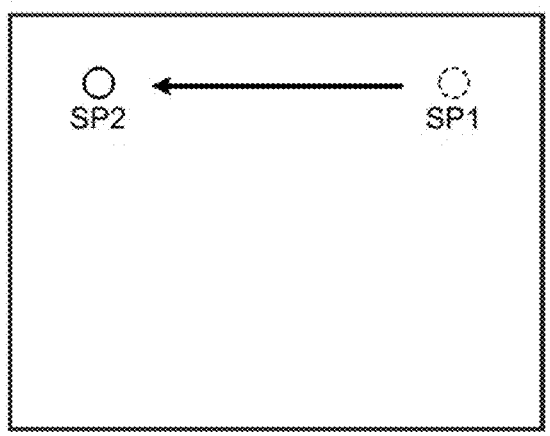
FIG. 25C is a diagram to describe the display processing of the mark of the target point in the detecting processing of point of regard for correction.
Figure 25D:
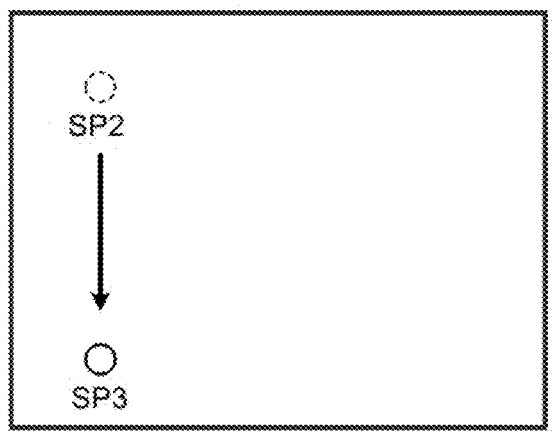
FIG. 25D is a diagram to describe the display processing of the mark of the target point in the detecting processing of point of regard for correction.
Figure 25E:
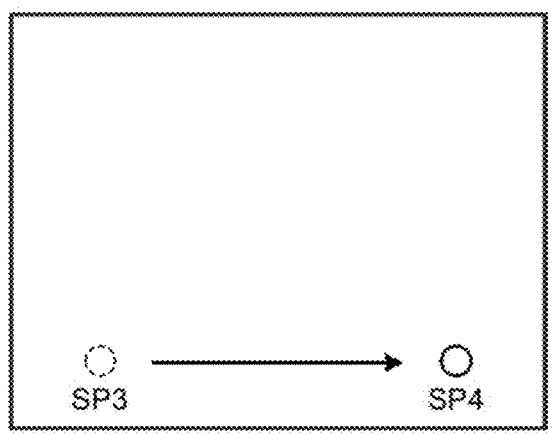
FIG. 25E is a diagram to describe the display processing of the mark of the target point in the detecting processing of point of regard for correction.

That is, the output controller 354 stops displaying SP0 and newly displays SP1 in step S117 as illustrated in FIG. 25B. After the representative value of SP1 is calculated, the output controller 354 stops displaying SP1 and newly displays SP2 as illustrated in FIG. 25C in step S117 again. Similarly, the output controller 354 subsequently stops displaying SP2 and newly displays a target point of SP3 as illustrated in FIG. 25D. Subsequently, the output controller 354 stops displaying SP3 and newly displays a target point of SP4 as illustrated in FIG. 25E.

In this way, the respective target points are displayed one by one in the order so that the points of regard for correction of the subject can be detected.

Next, another example of the mark of the target point will be described. FIGS. 26 to 36 are diagrams of exemplary marks of the target points. In the examples in FIGS. 26 to 36, a mark including a frame with a predetermined shape and an image displayed in the frame is used. Also, output controller 354 displays different images for each of the plurality of target points from each other. In addition, the output controller 354 displays the moving image as the image in the frame. The moving image is such that the display mode of a part including the center of the frame changes. This makes the subject regard the position closer to the center of the marks of the target points. It is preferable that the part where the display mode changes in the frame does not strictly include a center point of the frame. For example, it is not necessary to be the center when a point to attract the attention is determined. In this case, it is necessary to consider that the point to attract the attention is not the center when the point of regard for correction is calculated.

In FIGS. 26 to 36, five marks of the target points are displayed in an order of SP0□SP2□SP3□SP4□SP1 in FIG. 5. In this way, a display order of the marks of the target points may be voluntarily changed.

Figure 26:
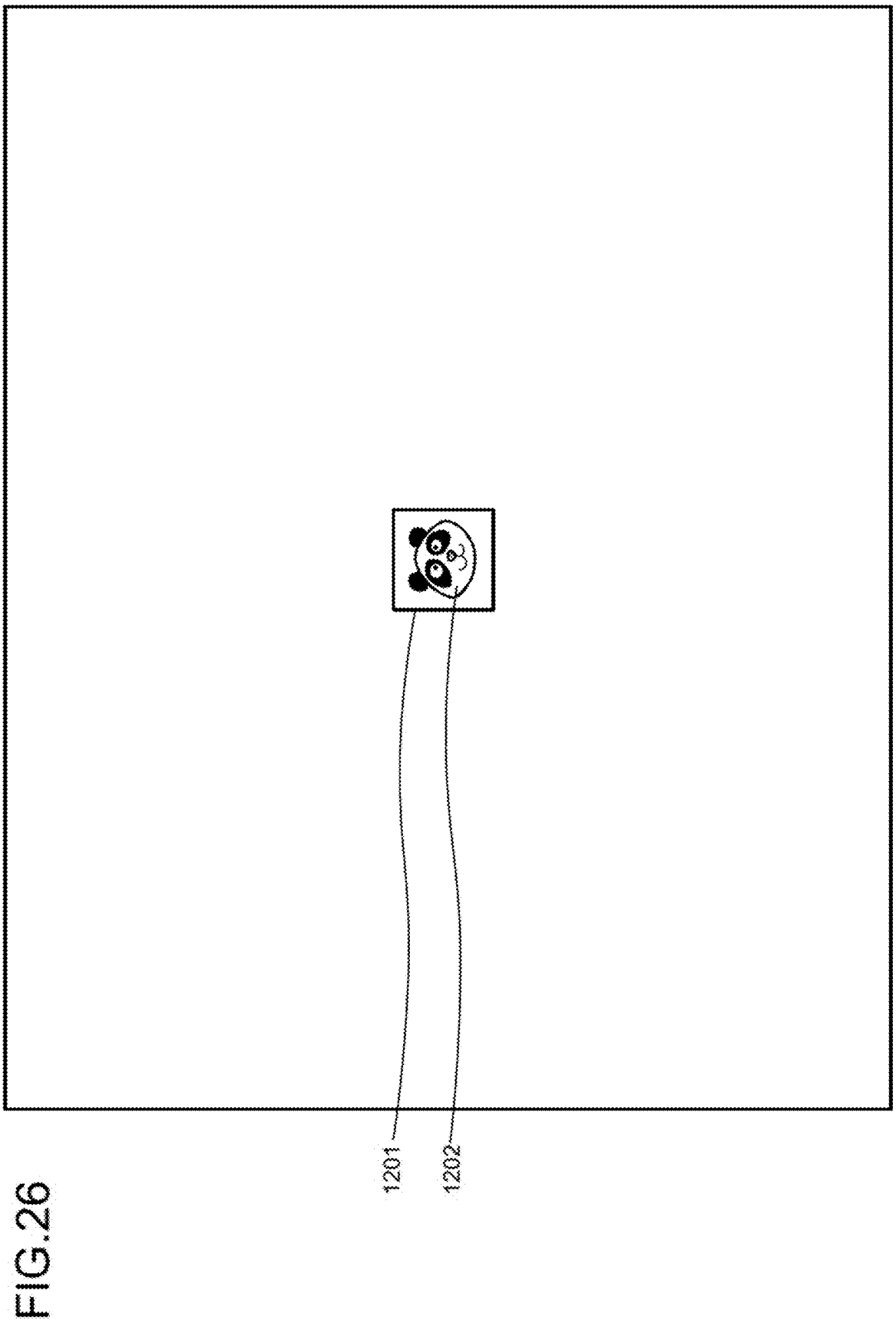
FIG. 26 is a diagram of an exemplary mark of the target point.
Figure 27:
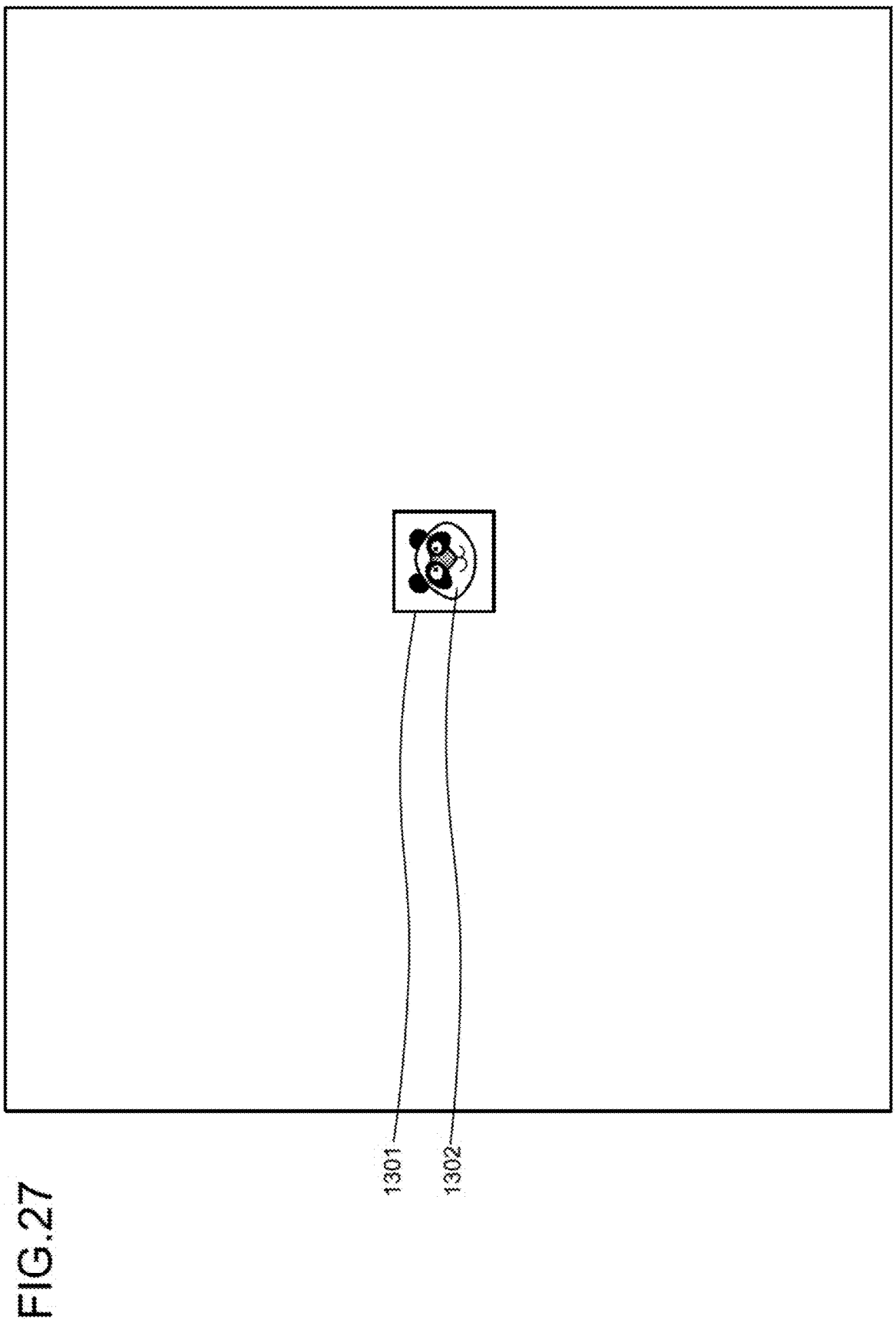
FIG. 27 is a diagram of an exemplary mark of the target point.

In FIG. 26, the output controller 354 displays a frame 1201 and an image 1202 of a character positioned in the frame at a position corresponding to SP0 first. The image 1202 is a moving image in which a region around the center moves. FIG. 27 is a diagram of a situation where an image 1302 of the character after a part of a nose around the center has moved to be enlarged is displayed in a frame 1301.

Figure 28:
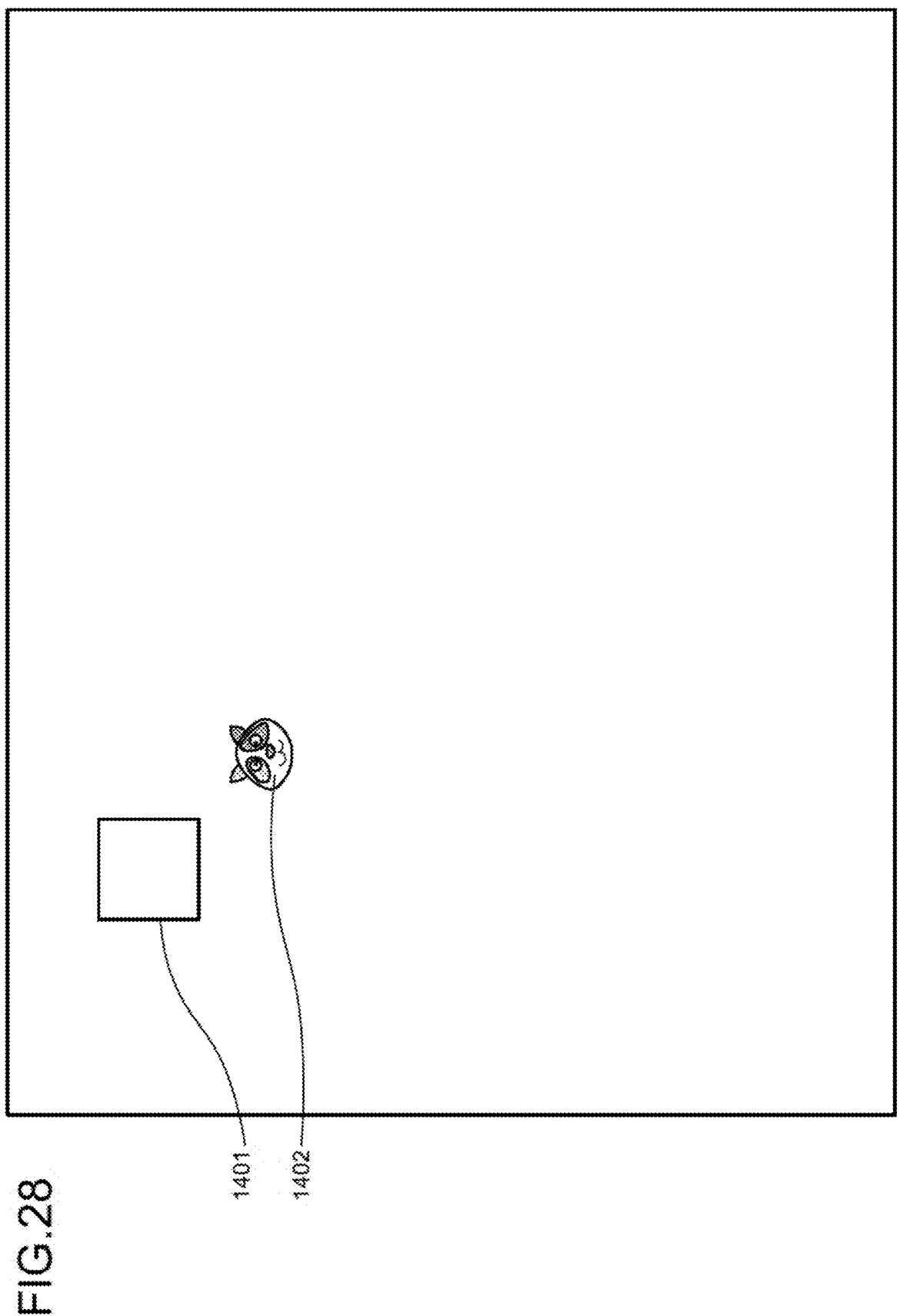
FIG. 28 is a diagram of an exemplary mark of the target point.

As illustrated in FIG. 28, the output controller 354 may display the frame at the target point first. After that, the output controller 354 may display the image of the character so as to move it toward the target point. Accordingly, the point of regard of the subject can be appropriately led to the next target point. FIG. 28 is a diagram of a situation where a frame 1401 is displayed at the target point (position of SP2 in FIG. 5) and an image 1402 of a character is moving to the frame 1401.

Figure 29:
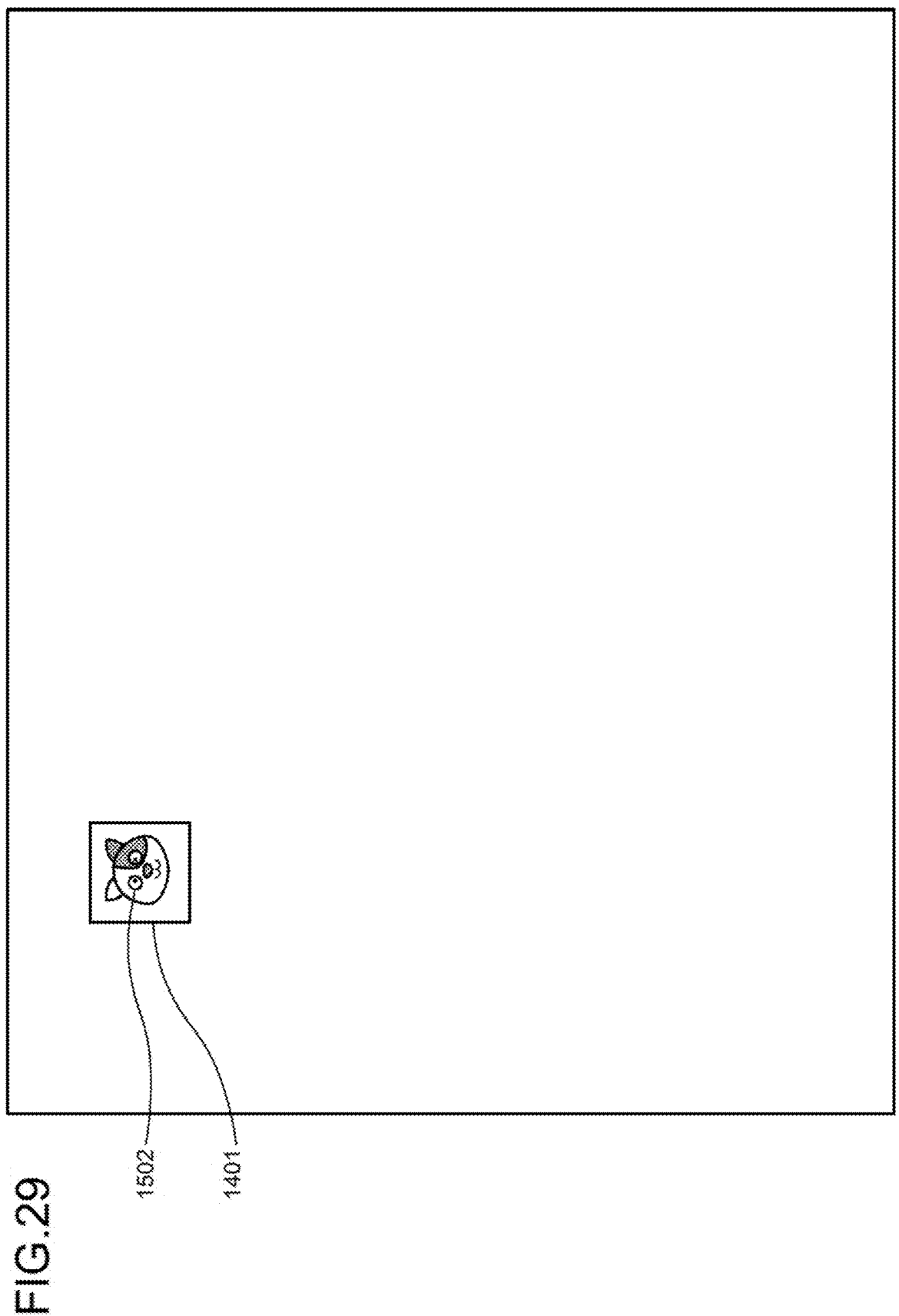
FIG. 29 is a diagram of an exemplary mark of the target point.
Figure 30:
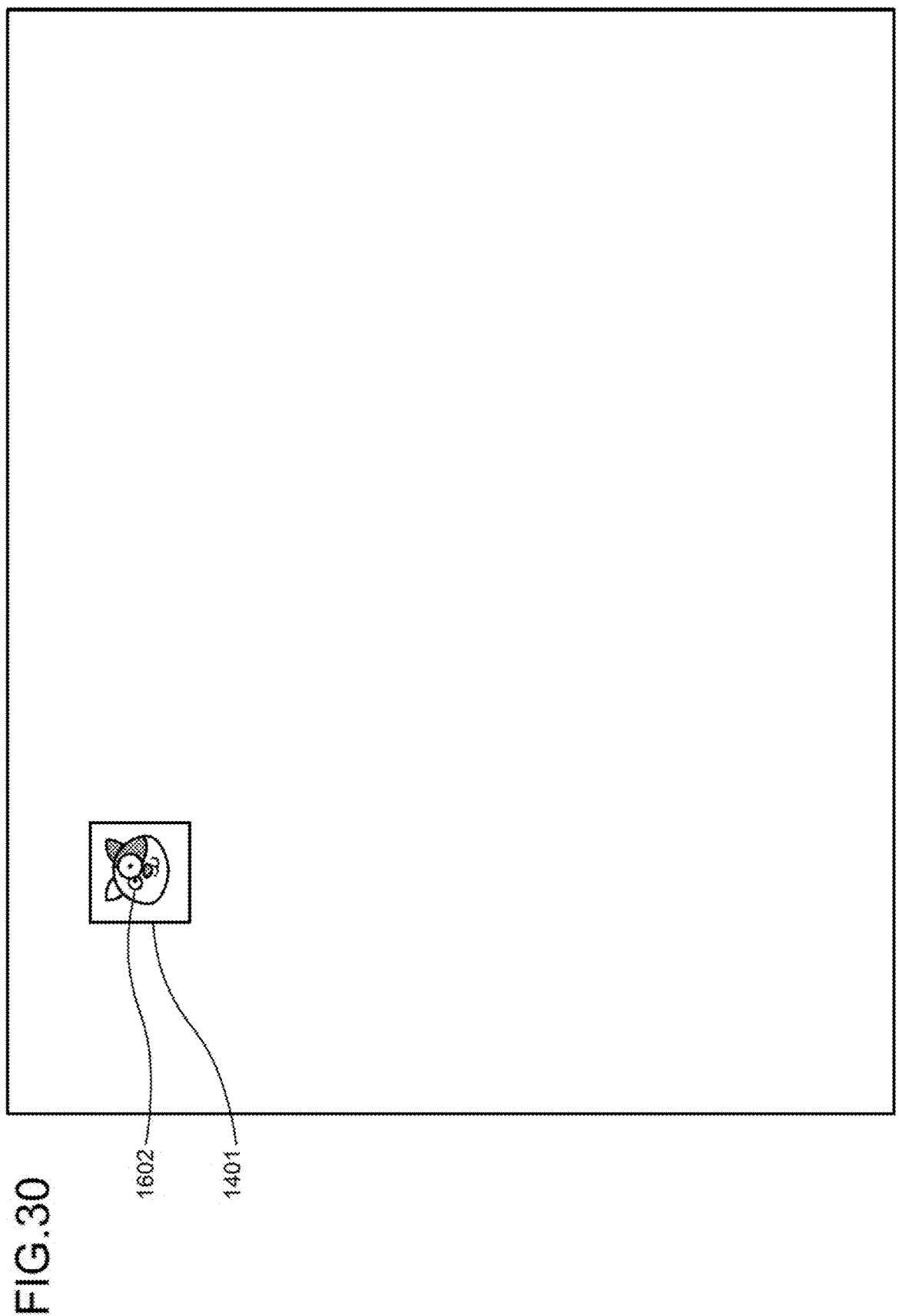
FIG. 30 is a diagram of an exemplary mark of the target point.

FIG. 29 is a diagram of a situation where an image 1502 of a character different from that of the image 1402 is displayed after the image 1402 of the character in FIG. 28 has been moved to the position of the frame 1401. In this way, the subject can pay attention to the image without getting bored by displaying different images from each other for each target point. FIG. 30 is a diagram of a situation where an image 1602 of the character after it has been moved so that parts of the eyes near the center of the image 1502 are enlarged is displayed in a frame 1401.

Figure 31:
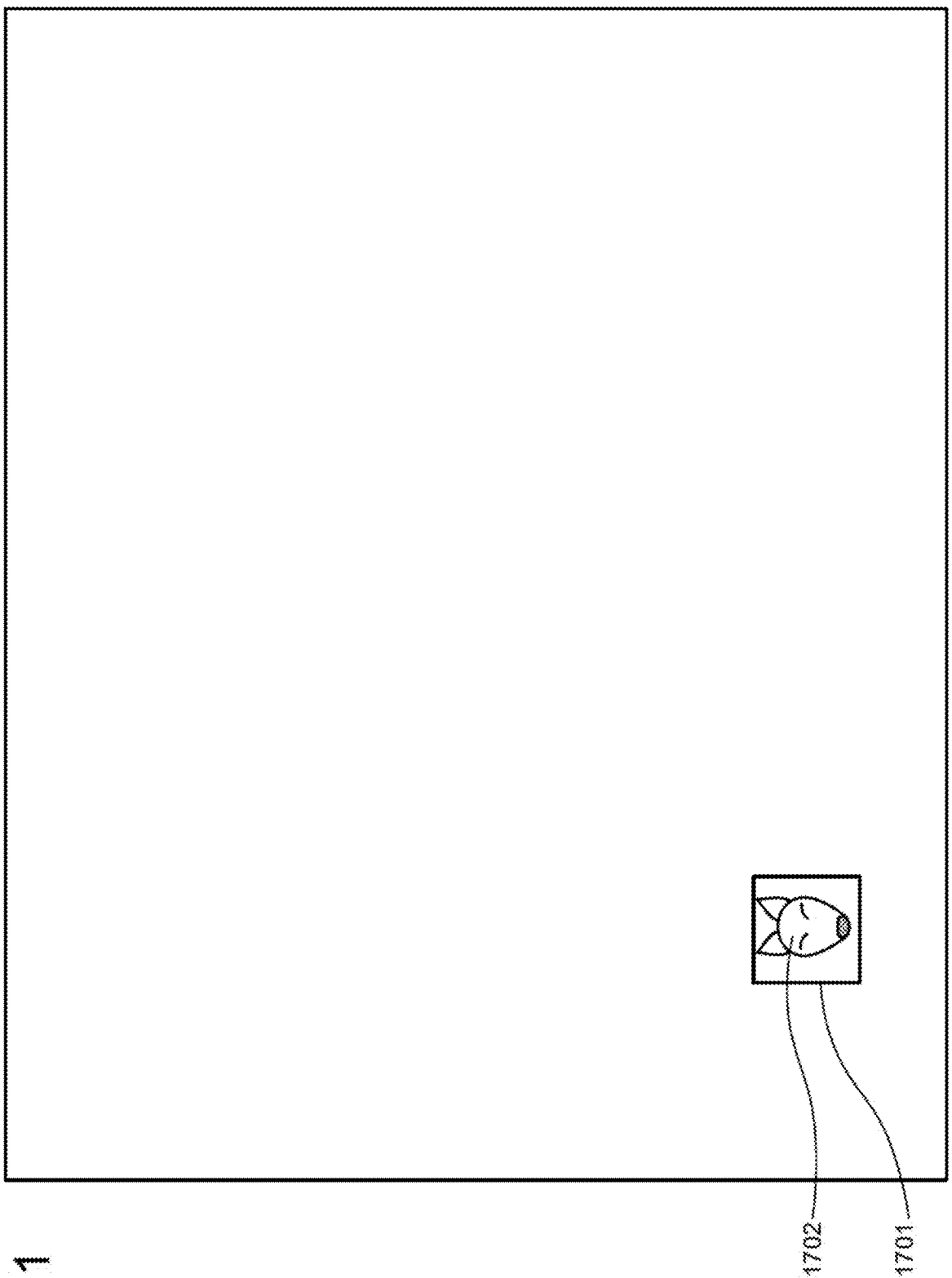
FIG. 31 is a diagram of an exemplary mark of the target point.
Figure 32:
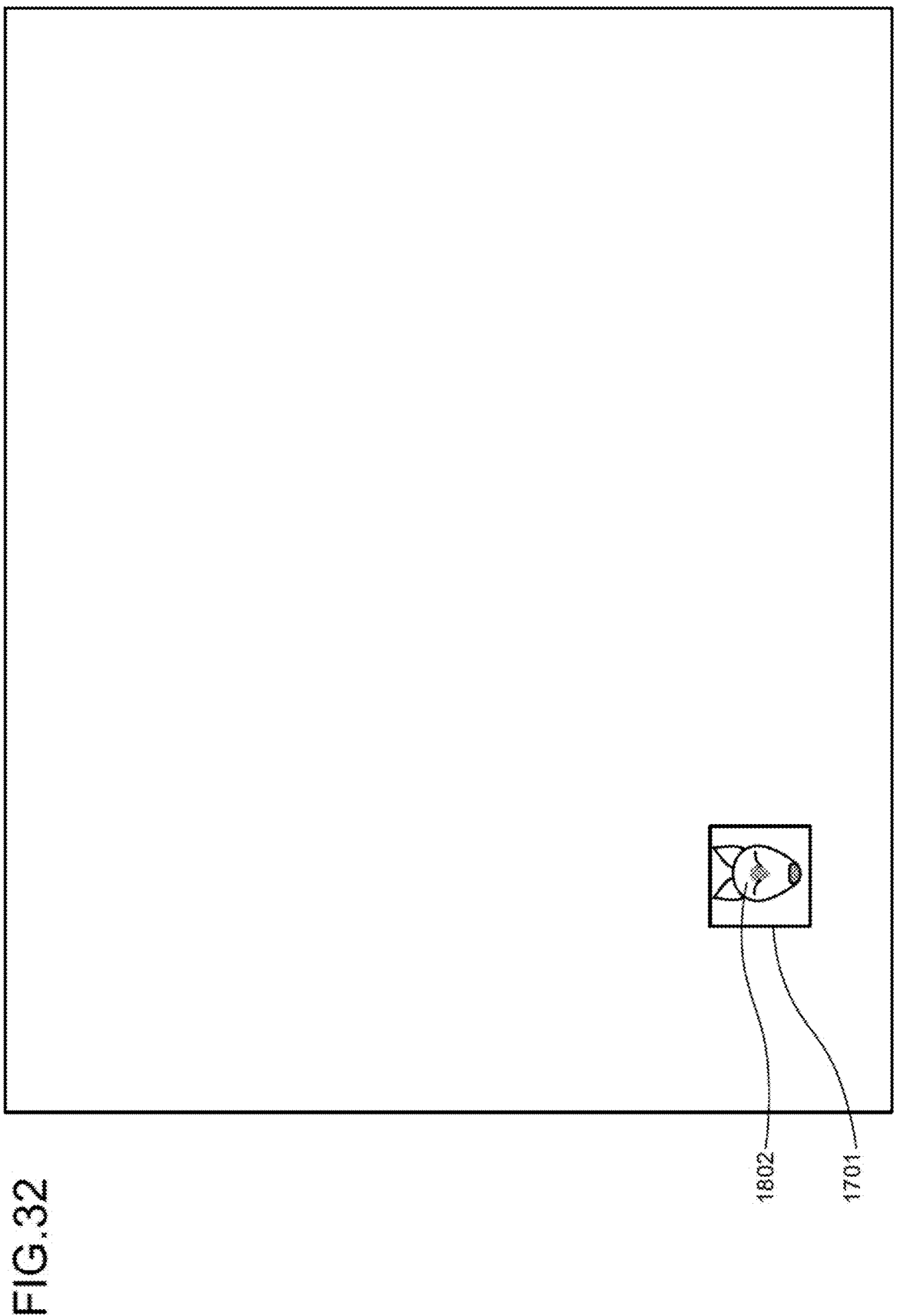
FIG. 32 is a diagram of an exemplary mark of the target point.

FIG. 31 is a diagram of a situation where an image 1702 of a character different from that of the image 1602 is displayed after the image 1602 of the character in FIG. 30 has been moved to a position of a frame 1701 (position of SP3 in FIG. 5). FIG. 32 is a diagram of a situation where an image 1802 of a character of which the color of a place near the center of the image 1702 has changed is displayed in a frame 1701.

Figure 33:
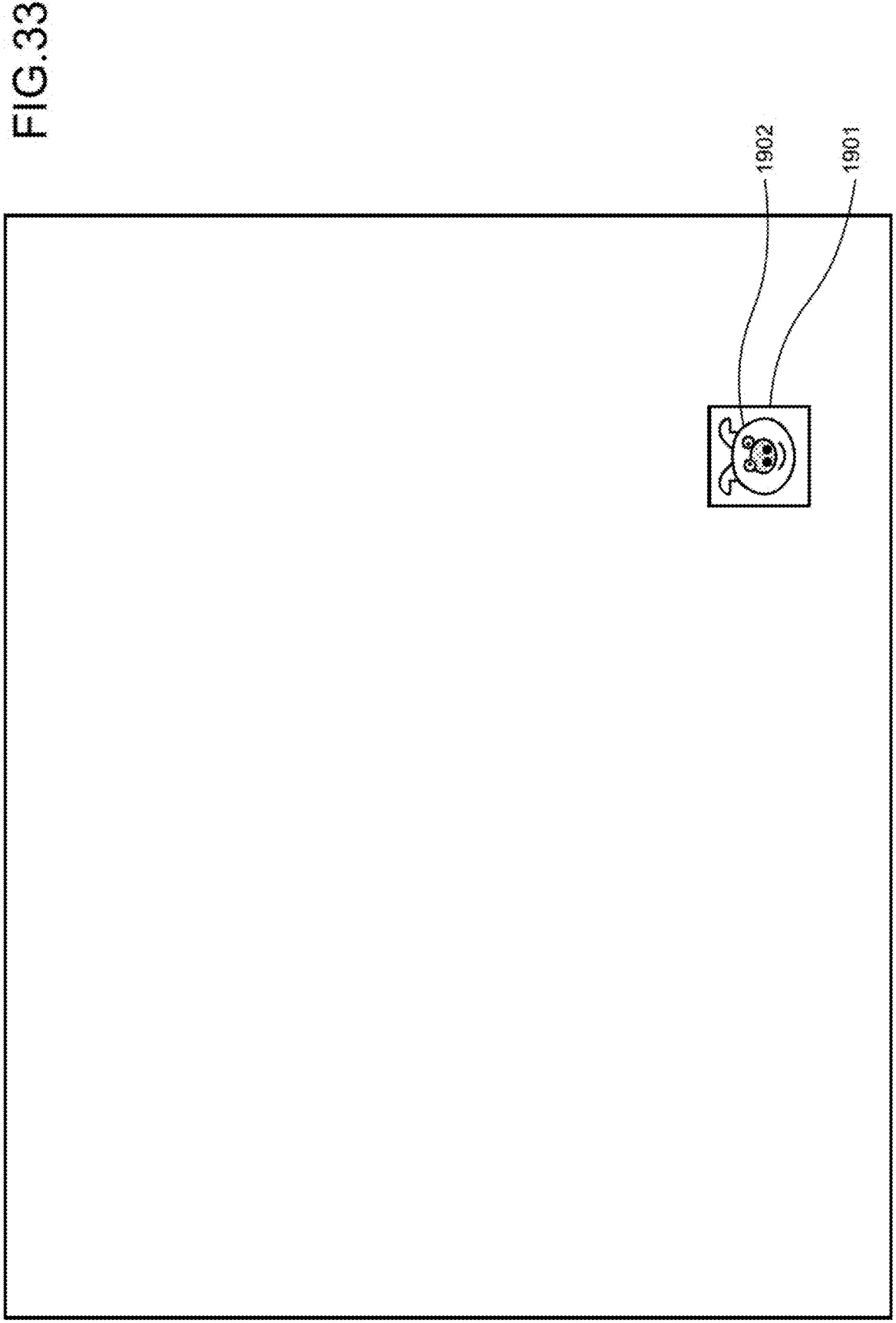
FIG. 33 is a diagram of an exemplary mark of the target point.
Figure 34:
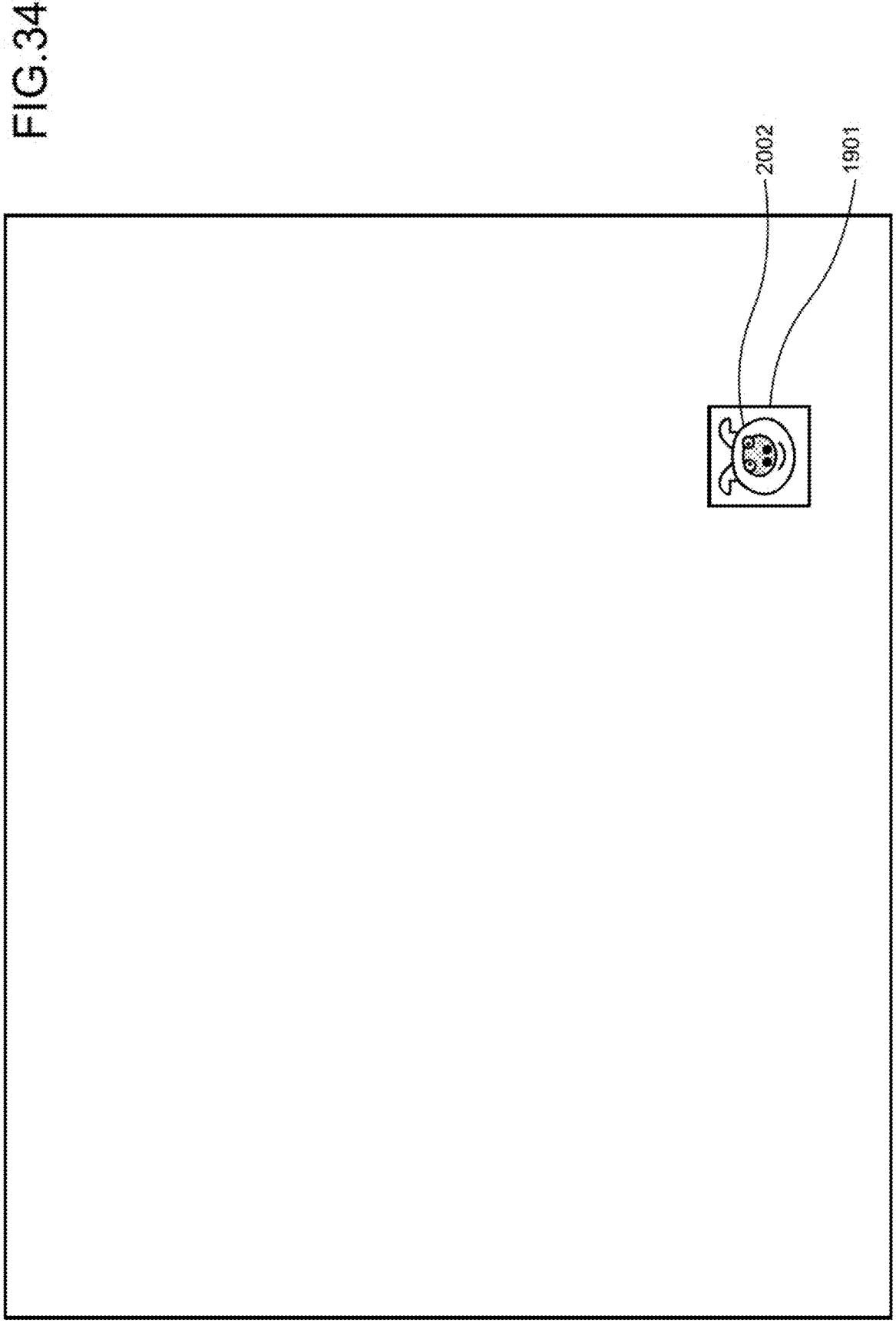
FIG. 34 is a diagram of an exemplary mark of the target point.

FIG. 33 is a diagram of a situation where an image 1902 of a character different from that of the image 1802 is displayed after the image 1802 of the character in FIG. 32 has been moved to a position of a frame 1901 (position of SP4 in FIG. 5). FIG. 34 is a diagram of a situation where an image 2002 of a character is displayed in the frame 1901 after a nose part near the center of the image 1902 has moved to be enlarged.

Figure 35:
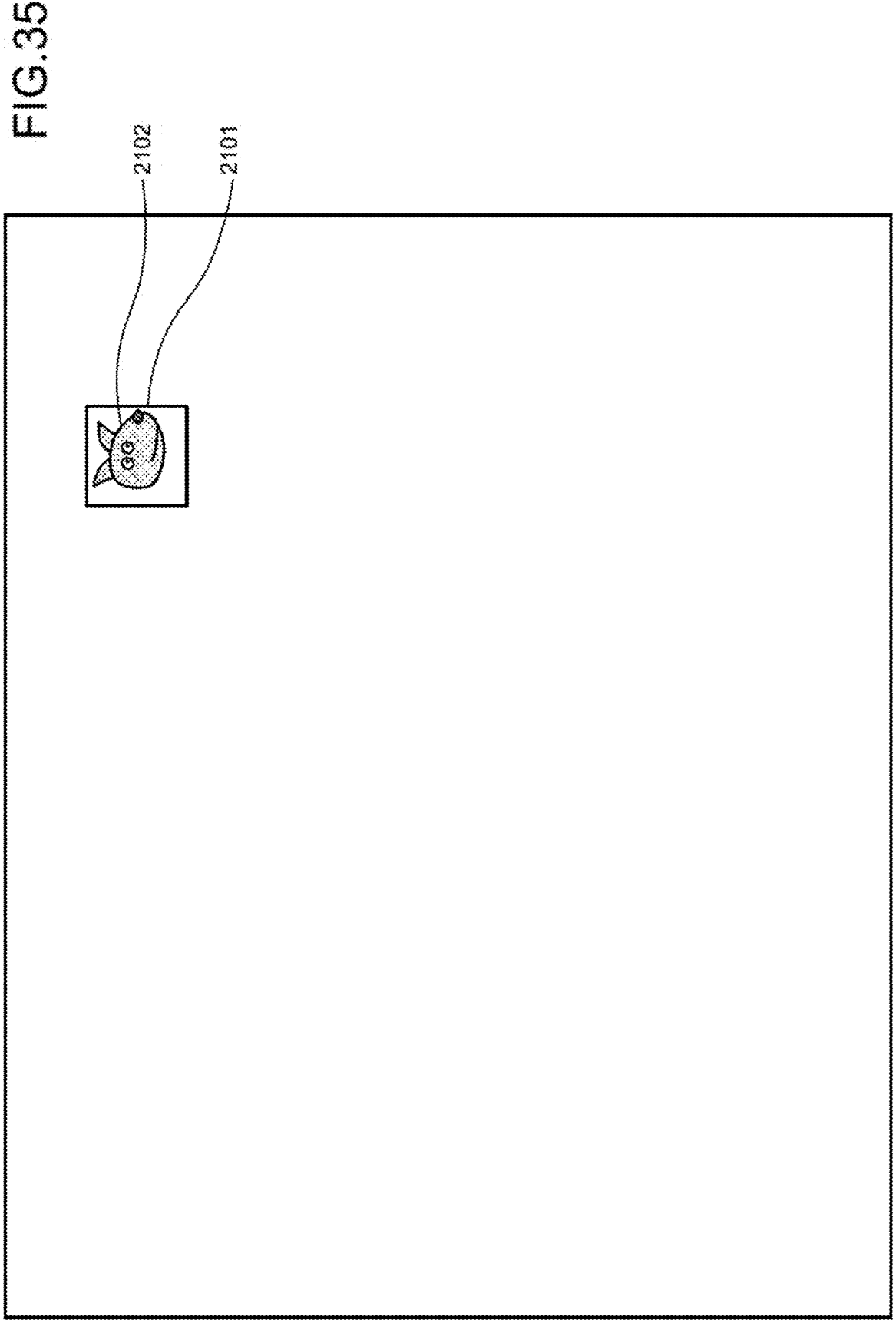
FIG. 35 is a diagram of an exemplary mark of the target point.
Figure 36:
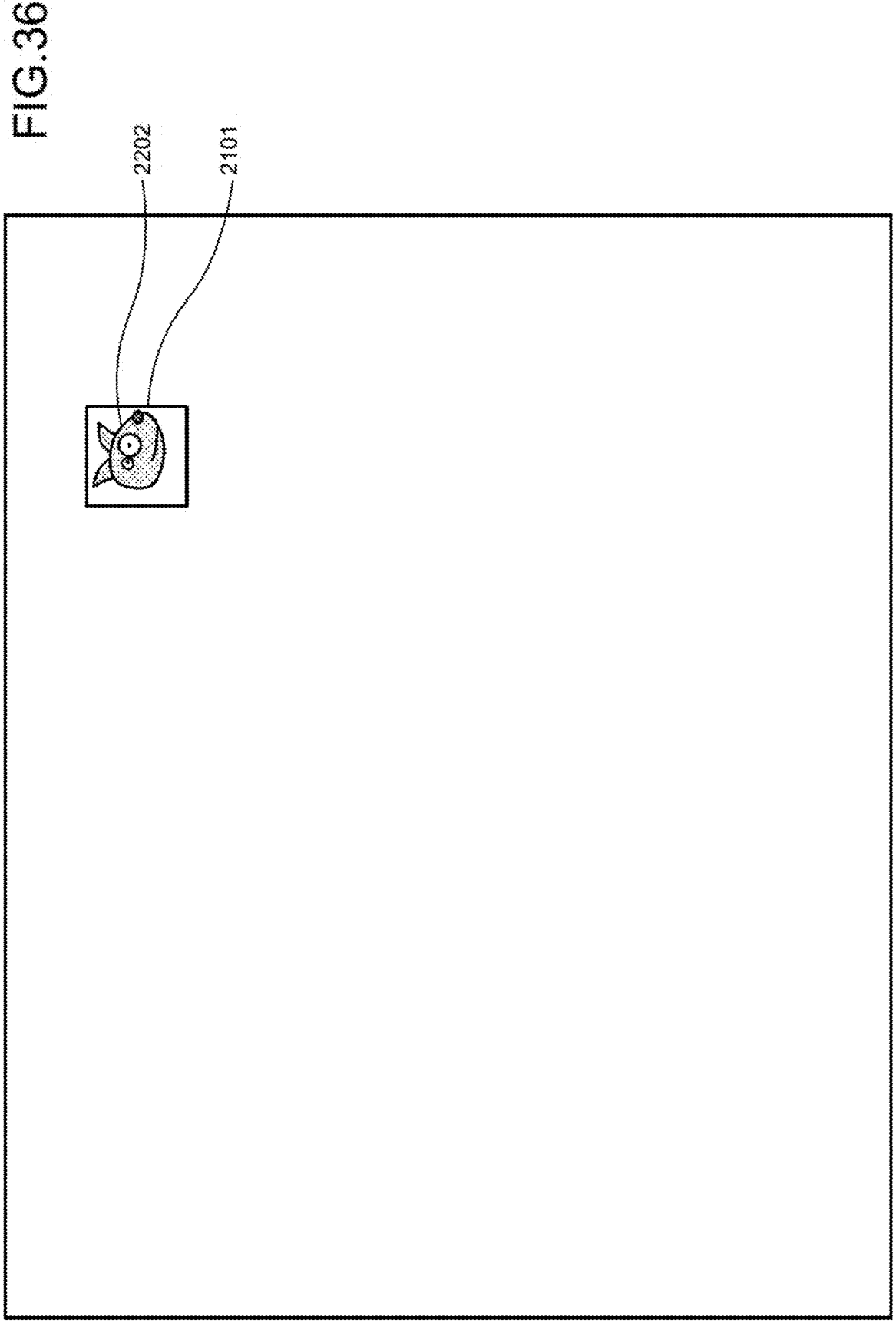
FIG. 36 is a diagram of an exemplary mark of the target point.

FIG. 35 is a diagram of a situation where an image 2102 of a character different from that of the image 2002 is displayed after the image 2002 of the character in FIG. 34 has been moved to a position of a frame 2101 (position of SP1 in FIG. 5). FIG. 36 is a diagram of a situation where an image 2202 of a character after it has been moved so that parts of the eyes near the center of the image 2102 are moved to be enlarged is displayed in the frame 2101.

Figure 37:
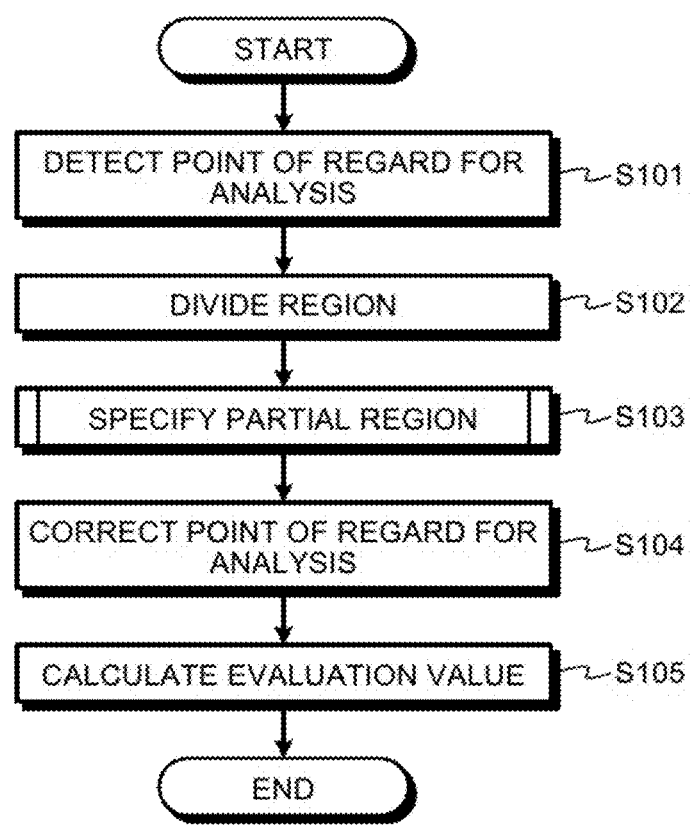
FIG. 37 is a flowchart of exemplary analysis processing according to the first embodiment.

Next, the analysis processing in step S5 will be described in detail. In the analysis processing in step S5, a single analysis processing or a plurality of analysis processing may be performed. When the plurality of analysis processing is performed, the evaluation unit 359 calculates the evaluation value by integrating the results of the respective analysis processing. FIG. 37 is a flowchart of exemplary analysis processing according to the first embodiment.

First, the diagnosis assisting apparatus 100 performs the detecting processing of point of regard for analysis (step S101). In the detecting processing of point of regard for analysis, the output controller 354 displays the diagnostic image on the display 210 first. Next, the point of view detecting unit 352 detects the point of regard of the subject, that is, the point of regard for analysis in a case where the diagnostic image is displayed on the display 210.

Subsequently, the region dividing unit 356 divides the target region into eight partial regions (A to H) based on the point of regard for correction which is the representative value relative to the marks of the target points (step S102). Next, the correction unit 358 specifies a partial region in the frame Fe to which the point of regard for analysis obtained in step S101 belongs. In addition, the correction unit 358 specifies a partial region in the frame F corresponding to the specified partial region (step S103).

Figure 38:
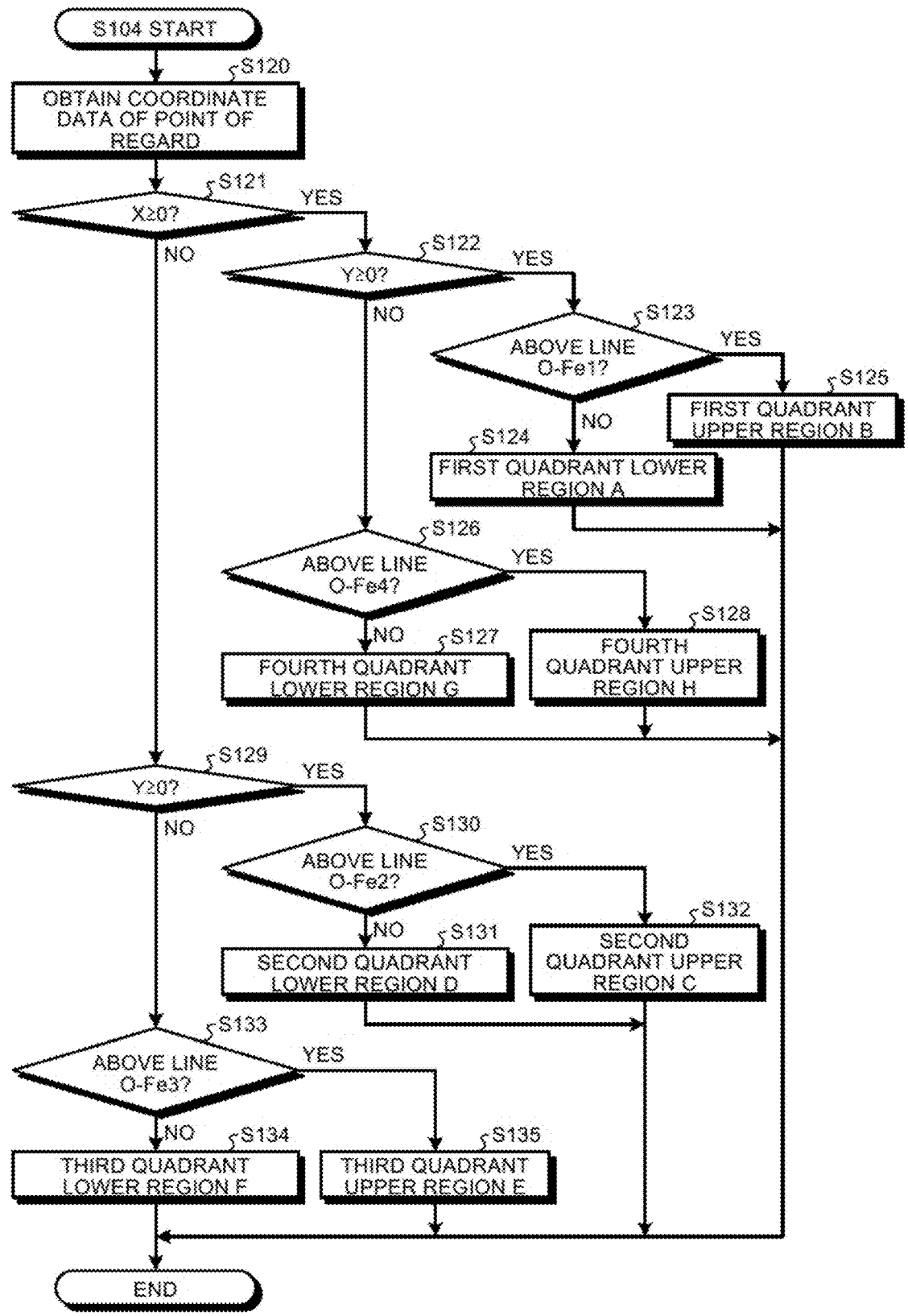
FIG. 38 is a flowchart of processing for specifying the partial region in the frame Fe in partial region specifying processing.

FIG. 38 is a flowchart of processing for specifying the partial region in the frame Fe in the partial region specifying processing (step S103). As illustrated in FIG. 38, first, the region specifying unit 357 obtains the coordinate of the point of regard for analysis obtained in step S101 from the point of view detecting unit 352 (step S120).

Next, the region specifying unit 357 specifies the partial region to which the point of regard for analysis belongs based on the coordinate of the point of regard for analysis and the partial regions (A to H) in the frame Fe. The region specifying unit 357 specifically specifies a sign of the x-coordinate of the point of regard for analysis and subsequently specifies a sign of the y-coordinate. When the x-coordinate of the point of regard for analysis is equal to or more than zero and the y-coordinate of the point of regard for analysis is equal to or more than zero (step S121, Yes and step S122, Yes), the region specifying unit 357 specifies whether the point of regard for analysis is positioned above a line connecting the origin O and the point Fe1 (line O-Fe1) based on the xy-coordinate of the point of regard for analysis and the coordinate of the point Fe1 (step S123).

When the point of regard for analysis is positioned on the line O-Fe1 or below the line O-Fe1 (step S123, No), the region specifying unit 357 determines that the point of regard for analysis belongs to the first quadrant lower region A (step S124).

When the point of regard for analysis is positioned above the line O-Fe1 (step S123, Yes), the region specifying unit 357 determines that the point of regard for analysis belongs to the first quadrant upper region B (step S125).

When the x-coordinate of the point of regard for analysis is equal to or more than zero and the y-coordinate of the point of regard for analysis is less than zero (step S121, Yes and step S122, No), the region specifying unit 357 specifies whether the point of regard for analysis is positioned above a line connecting the origin O and the point Fe4 (line O-Fe4) based on the xy-coordinate of the point of regard for analysis and the coordinate of the point Fe4 (step S126).

When the point of regard for analysis is positioned on the line O-Fe4 or below the line O-Fe4 (step S126, No), the region specifying unit 357 determines that the point of regard for analysis belongs to the fourth quadrant lower region G (step S127).

When the point of regard for analysis is positioned above the line O-Fe4 (step S126, Yes), the region specifying unit 357 determines that the point of regard for analysis belongs to the fourth quadrant upper region H (step S128).

When the x-coordinate of the point of regard for analysis is smaller than zero and the y-coordinate of the point of regard for analysis is equal to or more than zero (step S121, No and step S129, Yes), the region specifying unit 357 specifies whether the point of regard for analysis is positioned above a line connecting the origin O and the point Fe2 (line O-Fe2) based on the xy-coordinate of the point of regard for analysis and the coordinate of the point Fe2 (step S130).

When the point of regard for analysis is positioned on the line O-Fe2 or below the line O-Fe2 (step S130, No), the region specifying unit 357 determines that the point of regard for analysis belongs to the second quadrant lower region D (step S131).

When the point of regard for analysis is positioned above the line O-Fe2 (step S130, Yes), the region specifying unit 357 determines that the point of regard for analysis belongs to the second quadrant upper region C (step S132).

When the x-coordinate of the point of regard for analysis is smaller than zero and the y-coordinate of the point of regard for analysis is smaller than zero (step S121, No and step S129, No), the region specifying unit 357 specifies whether the point of regard for analysis is positioned above a line connecting the origin O and the point Fe3 (line O-Fe3) based on the xy-coordinate of the point of regard for analysis and the coordinate of the point Fe3 (step S133).

When the point of regard for analysis is positioned on the line O-Fe3 or below the line O-Fe3 (step S133, No), the region specifying unit 357 determines that the point of regard for analysis belongs to the third quadrant lower region F (step S134).

When the point of regard for analysis is positioned above the line O-Fe3 (step S133, Yes), the region specifying unit 357 determines that the point of regard for analysis belongs to the third quadrant upper region E (step S135).

As described above, processing for specifying the partial region to which the point of regard for analysis belongs in step S103 is completed.

The description returns to FIG. 37. After a partial region in the frame Fe to which the point of regard for analysis belongs has been specified, and in addition, a partial region in the frame F corresponding to the specified partial region has been specified, the correction unit 358 corrects the position of the point of regard for analysis (step S104). In correcting processing of point of regard for analysis in step S104, the correction unit 358 calculates the position of the corrected point of regard for analysis by performing arithmetic processing which is different for each partial region specified in step S103. The detail of the arithmetic processing is as described above.

Next, the evaluation unit 359 calculates the evaluation value based on the position of the corrected point of regard for analysis (step S105). For example, the evaluation unit 359 calculates the evaluation value by integrating a plurality of evaluation items. The evaluation unit 359 calculates the evaluation value, for example, according to the ratio in which the position of the point of regard for analysis is included in an evaluation region of the diagnostic image to be described in FIGS. 39 to 44. The evaluation unit 359 may calculate the evaluation value according to a concentration degree calculated by time when the position of the point of regard for analysis stays at a single position. The analysis processing is completed as described above. When the result display to be output for the diagnosing person (doctor and the like) is performed as illustrated in FIGS. 51 to 54, the processing for calculating the evaluation value in step S105 is omitted. During the display of the diagnostic image, the point of view detecting unit 352 may calculate the evaluation region which includes the point of regard of the subject during the display of the diagnostic image on the display 210, that is, the position of the point of regard for analysis or an index of the concentration degree.

The correction method by the correction unit 358 is only exemplary, and the correction method is not limited to this. All the other methods can be applied when the method is to correct the point of regard for analysis by using the point of regard for correction detected from the marks corresponding a predetermined number (for example, five) of the target points.

Next, an example of the diagnostic image will be described. FIGS. 39 to 44 are diagrams of exemplary diagnostic images. FIGS. 39 to 44 are examples of the diagnostic image including a natural image and a geometrical image. The geometrical image indicates an image including one or more geometric patterns. This is because the developmental disorder child prefers an image of the geometrical image rather than the natural image. It is preferable that the natural image be an image of a natural object or an image for suggesting the natural object other than the geometrical image. For example, an image (still image, moving image) of a human, an animal, a plant, and a natural landscape taken by the camera may be used as the natural image. Also, an image (still image, moving image) of a character shaped like a human and an animal may be used as the natural image.

The evaluation unit 359 calculates the evaluation value, for example, when the geometrical image attracts more attention than the natural image. The above evaluation value indicates that the degree of the developmental disorder is high. The evaluation unit 359, for example, determines whether the point of view detected by the point of view detecting unit is in the evaluation region where the geometric pattern is displayed or the evaluation region where the natural image is displayed. Also, for example, the evaluation unit 359 determines whether the point of view detected by the point of view detecting unit is in the evaluation region where the geometric pattern is displayed. When there is a high possibility that the point of view is in the evaluation region where the geometric pattern is displayed, the evaluation value of the developmental disorder is calculated to be higher.

In a case where the diagnostic image is the moving image and when the diagnostic image in which the geometrical image attracts more attention is used, such as a case where the geometrical image moves faster than the natural image and a case where the color of the geometrical image is bright, there is a possibility that a non-handicapped person pays attention to the geometrical image. As illustrated in the examples in FIGS. 39 to 44, the diagnostic image including the geometrical image similar to the natural image may be displayed. For example, the geometrical image which has at least one of the color tone, the distribution of the brightness, the shape, the moving speed, and the position in the image (composition) similar to or corresponding to that of the natural image can be used. Also, when the natural image includes objects such as humans and animals, the geometrical image including the same number of the geometric patterns as that of the objects in the natural image may be used. In this case, the geometric patterns corresponding to the humans may be circles or ellipses.

Also, when the natural image includes a face of the human, the animal, and the character shaped like the human and the animal, the geometrical image including the geometric pattern having the same size as that of the face may be used. For example, the geometrical image may be used which includes a circle in which a difference between the width or length of the face and the radius is equal to or less than a first threshold, an ellipse in which a difference between the width of the face and the length of a minor axis is equal to or less than a second threshold, or an ellipse in which a difference between the length of the face and the length of a major axis is equal to or less than a third threshold as the geometric pattern.

Also, when a plurality of diagnostic images is used, the plurality of diagnostic images having different arrangements of the natural image and the geometrical image from each other may be used. For example, the diagnostic image including the natural image and the geometric pattern arranged in a first direction relative to the natural image has been used, and after that, the diagnostic image including the natural image and the geometric pattern arranged in a second direction (for example, opposite direction of the first direction) different from the first direction relative to the natural image may be used. Accordingly, the diagnosis accuracy can be improved.

Figure 39:
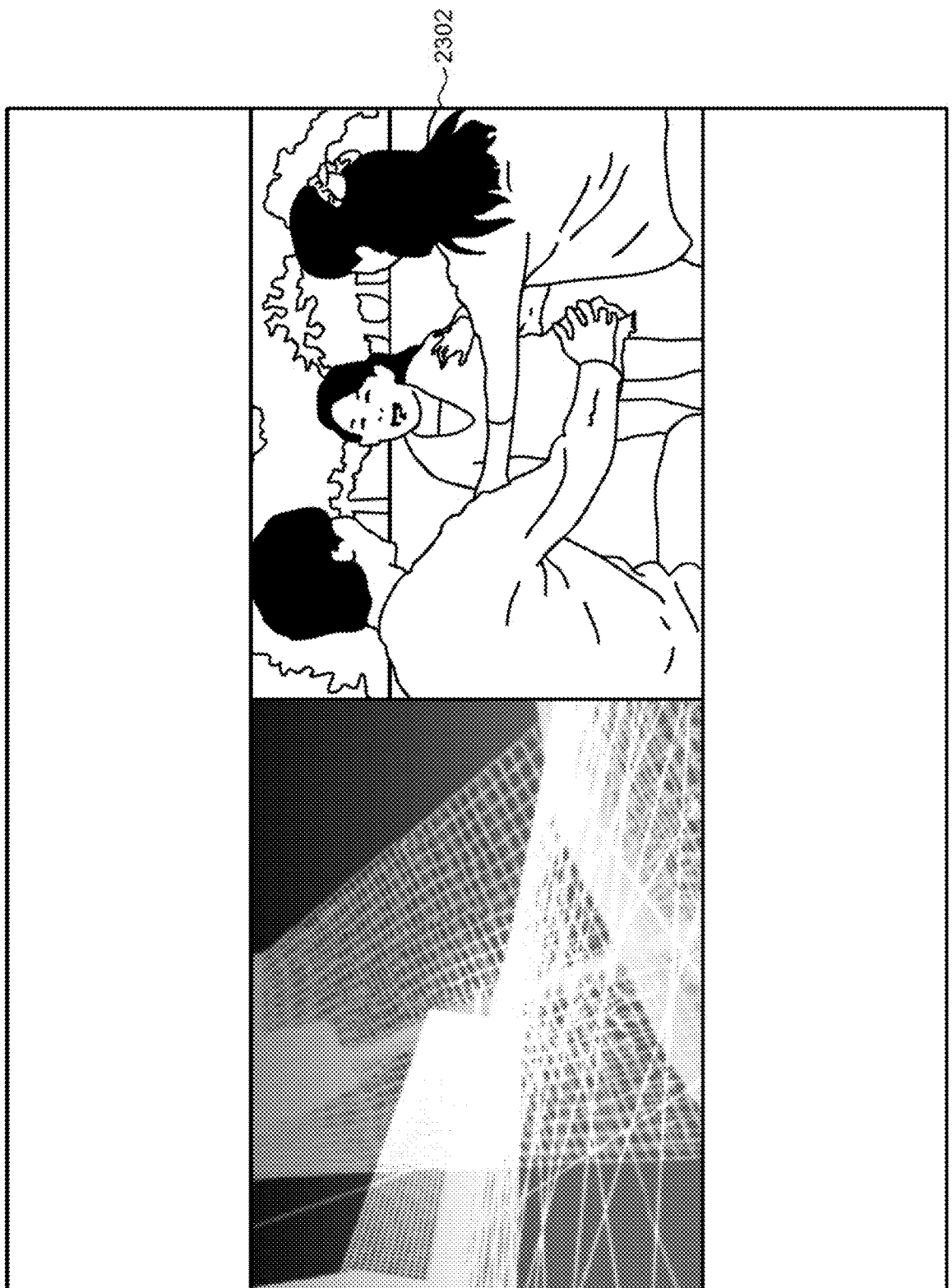
FIG. 39 is a diagram of an exemplary diagnostic image.

FIG. 39 is an exemplary diagnostic image including a geometrical image 2301 and a natural image 2302. The natural image 2302 including three humans against an open space in a park and trees is schematically illustrated in FIG. 39. However, a photograph having this composition may be used as the natural image 2302. The image in FIG. 39 does not indicate the color. However, when a colored natural image 2302 is used, the geometrical image 2301 including the geometric pattern having colors similar to those of the natural image 2302 may be used. For example, a background of the geometric pattern may be green according to the green color of grass in the forest and the park of the background. Also, the geometrical image 2301 including the geometric pattern of the color similar to that of the clothing of the human (a part where a plurality of lines is overlapped and the like in the example in FIG. 39) may be used.

Figure 40:
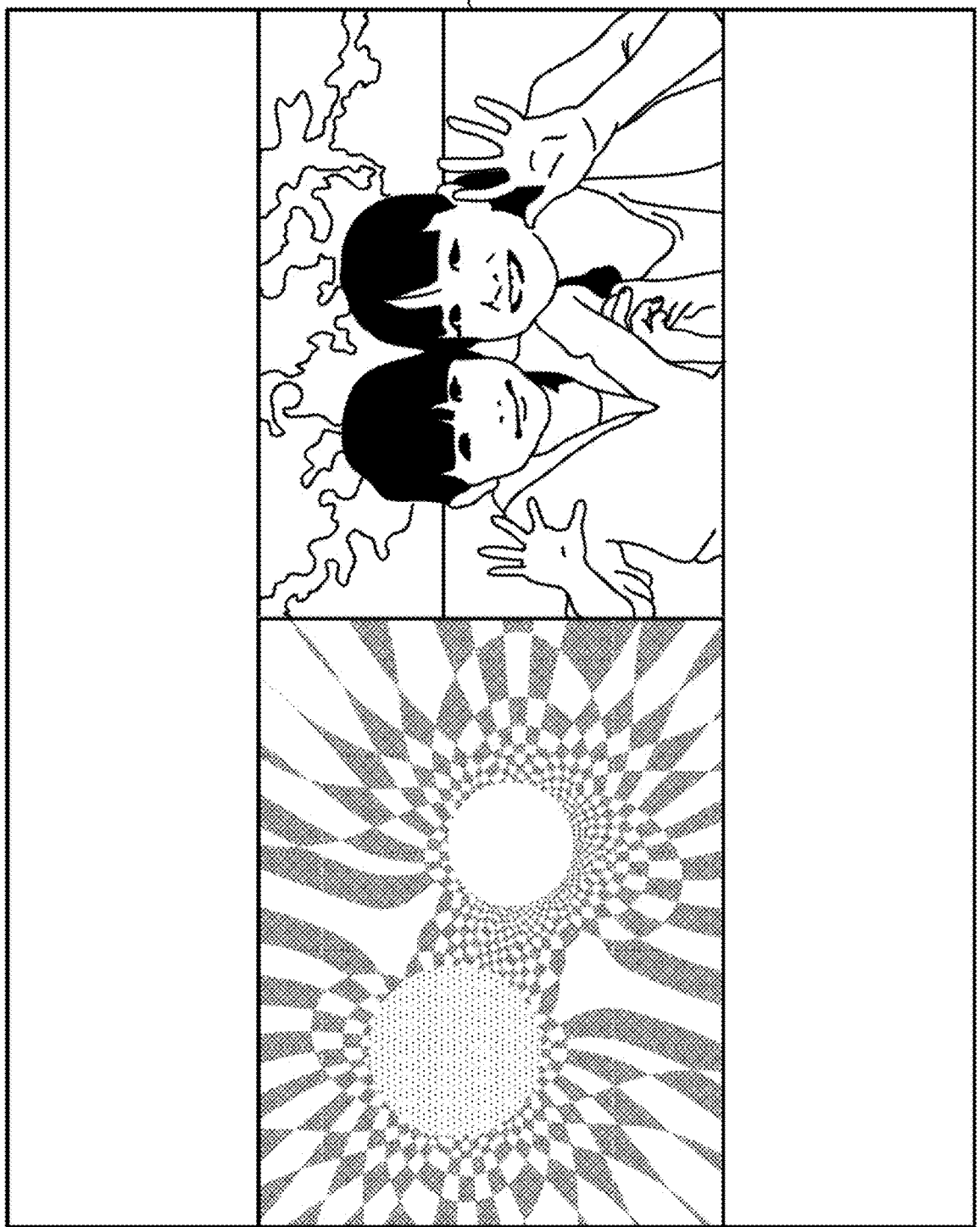
FIG. 40 is a diagram of an exemplary diagnostic image.

FIG. 40 is an exemplary diagnostic image including a geometrical image 2401 and a natural image 2402. The natural image 2402 including two humans against the open space of the park and trees is schematically illustrated in FIG. 40. In FIG. 40, an example of a geometrical image 2401 is illustrated which includes two circular geometric patterns having the sizes substantially similar to those of the faces of the two humans. The image in FIG. 40 does not indicate the color. However, for example, the circular geometric patterns respectively having the colors corresponding to or similar to those of the clothing of the two humans may be used.

Figure 41:
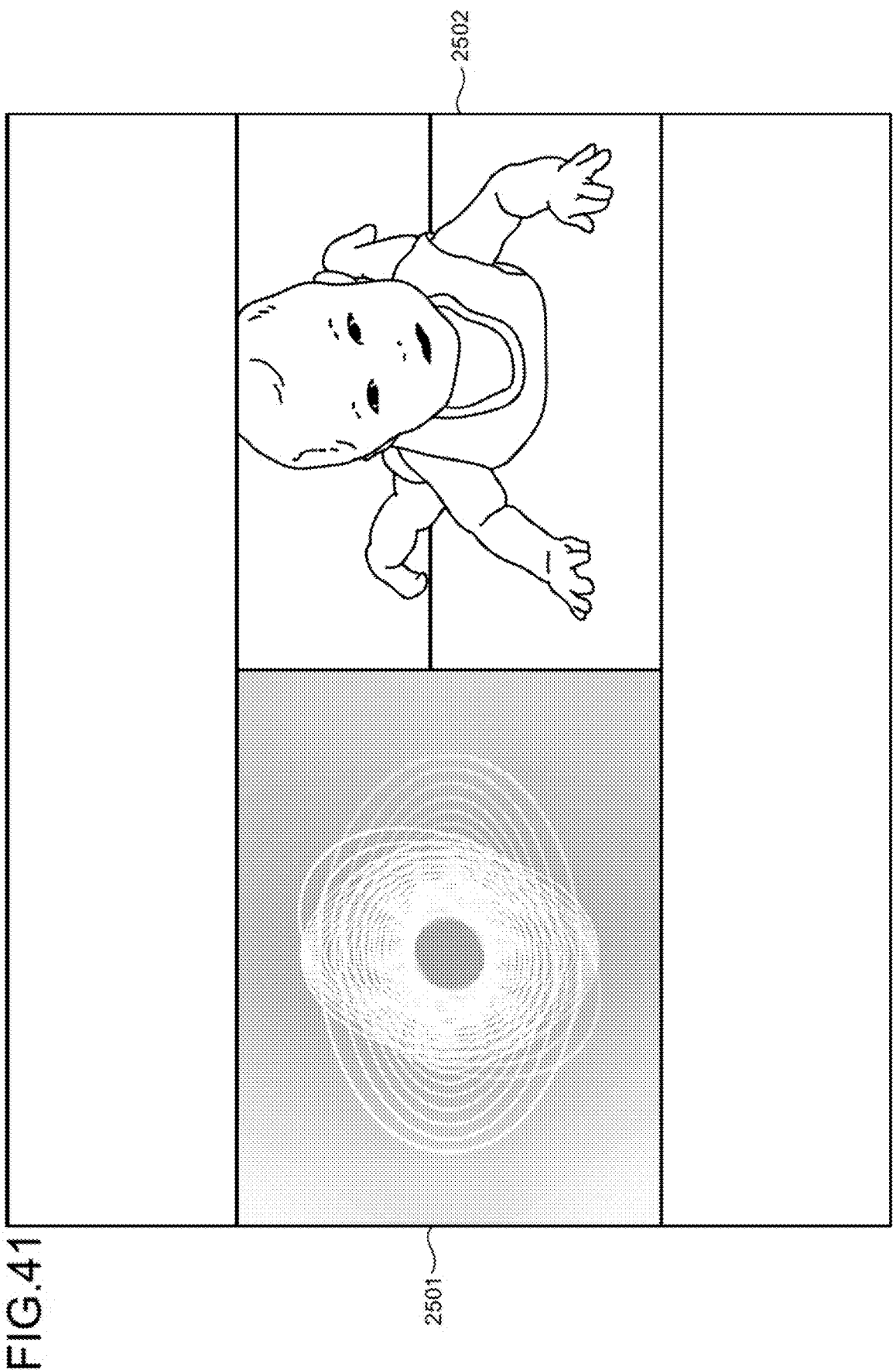
FIG. 41 is a diagram of an exemplary diagnostic image.

FIG. 41 is an exemplary diagnostic image including a geometrical image 2501 and a natural image 2502. The natural image 2502 including a single infant is schematically illustrated in FIG. 41. Also, in FIG. 41, an example of the geometrical image 2501 is illustrated which includes the geometric pattern of the elliptical shape having the size substantially similar to that of the face of the infant. The image in FIG. 41 does not indicate the color. However, for example, the geometric pattern having the color which is the same as or similar to that of the infant or the background in the natural image or the geometric pattern including the background may be used. Also, the arrangement of the colors in the natural image may be the same as or similar to that of the geometric pattern. Also, the arrangement of the shading of the color in the natural image may be the same as or similar to that of the geometric pattern.

Figure 42:
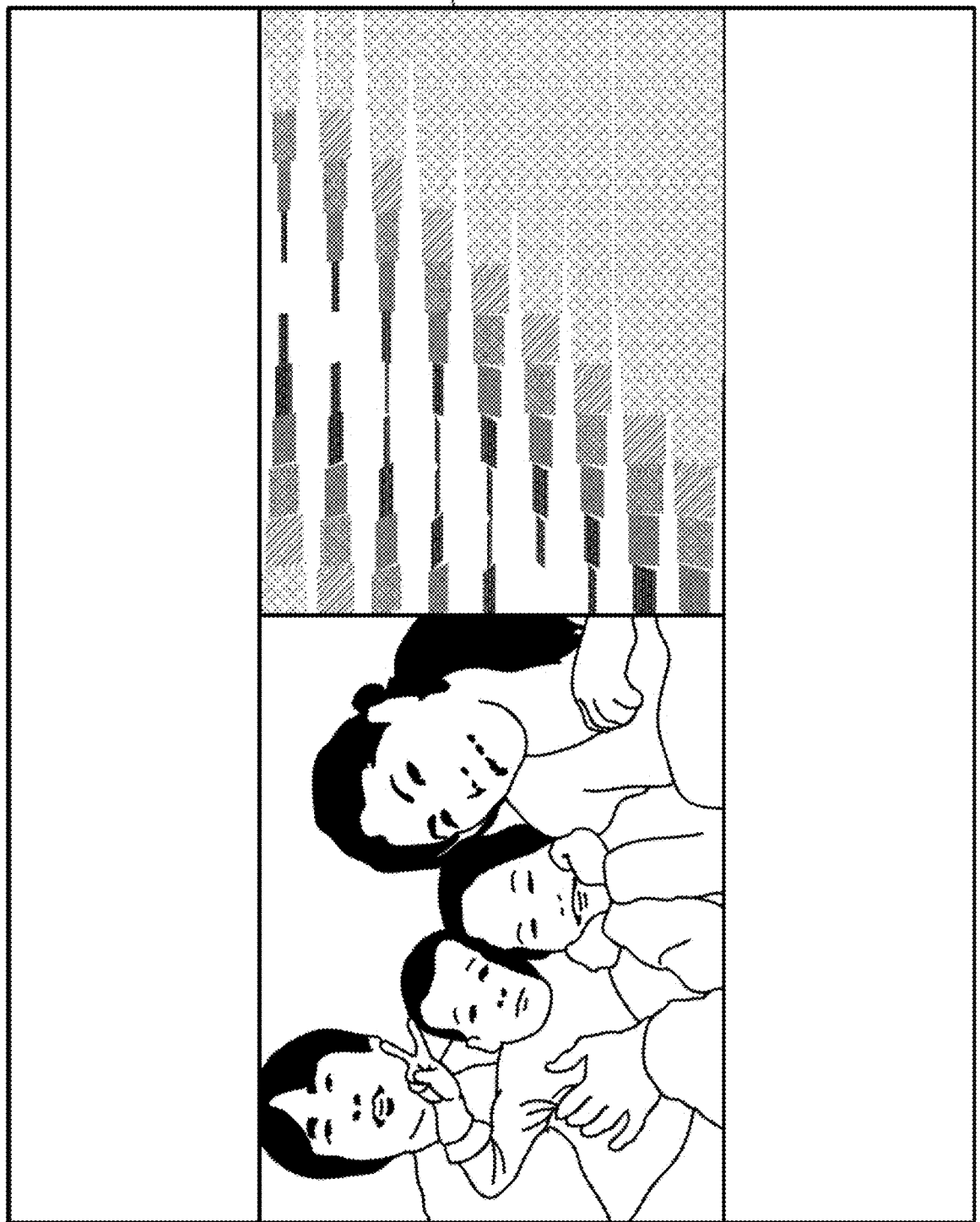
FIG. 42 is a diagram of an exemplary diagnostic image.

FIG. 42 is an exemplary diagnostic image including a geometrical image 2602 and a natural image 2601. The natural image 2601 including four humans against the sky in the background is schematically illustrated in FIG. 42. The image in FIG. 42 does not indicate the color. However, for example, the geometrical image 2602 including a blue geometric pattern may be used according to the blue sky in the background.

Figure 43:
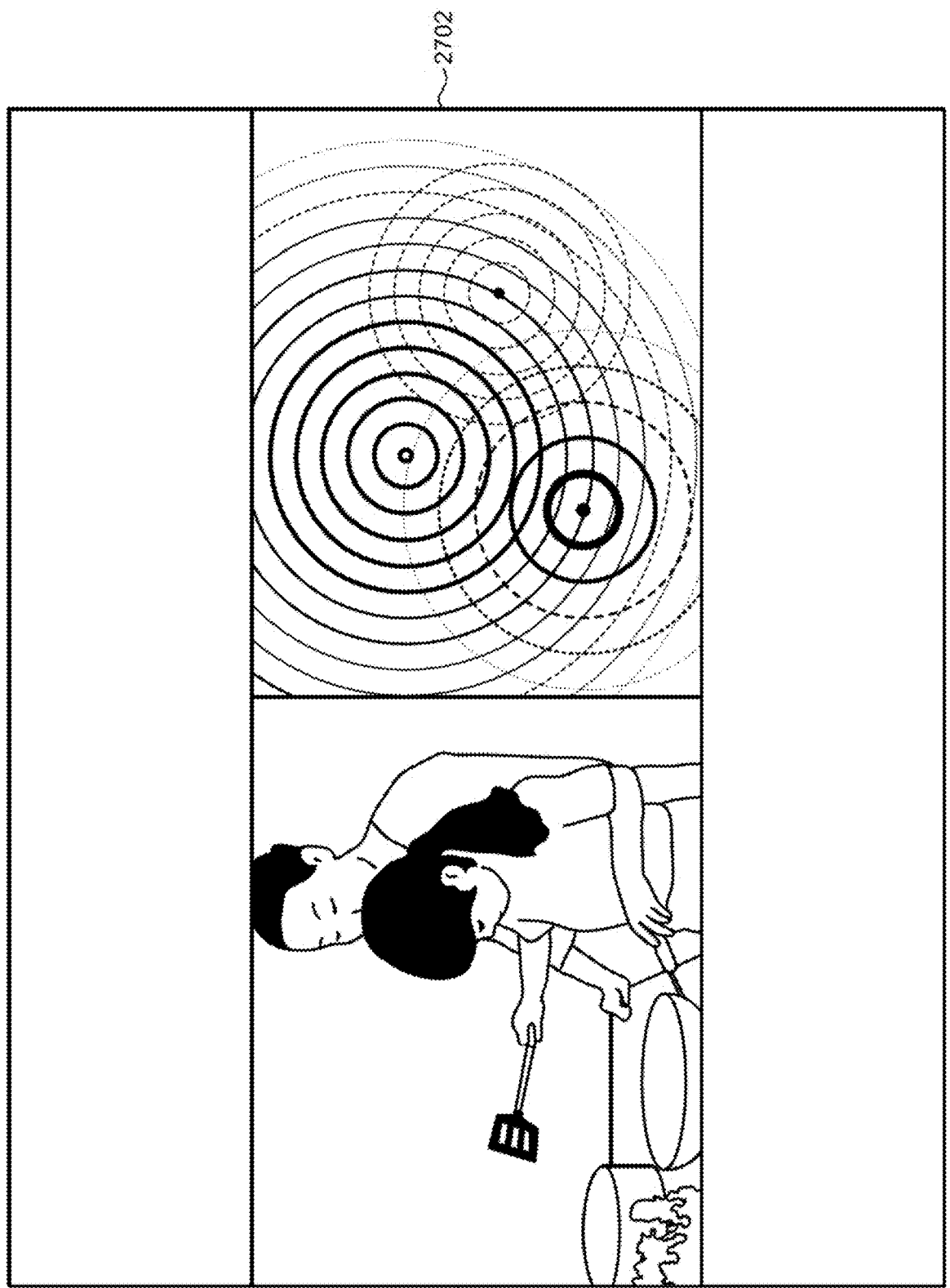
FIG. 43 is a diagram of an exemplary diagnostic image.

FIG. 43 is an exemplary diagnostic image including a geometrical image 2702 and a natural image 2701. The natural image 2701 including two humans who are cooking is schematically illustrated in FIG. 43. Also, in FIG. 43, an example of the geometrical image 2702 is illustrated which includes three circular geometric patterns corresponding to two humans and a circular frying pan. The image in FIG. 43 does not indicate the color. However, for example, the geometrical image 2702 including the circular geometric patterns having the color which is the same as or similar to that of the closing of the human located in front (for example, color of the line) may be used.

Figure 44:
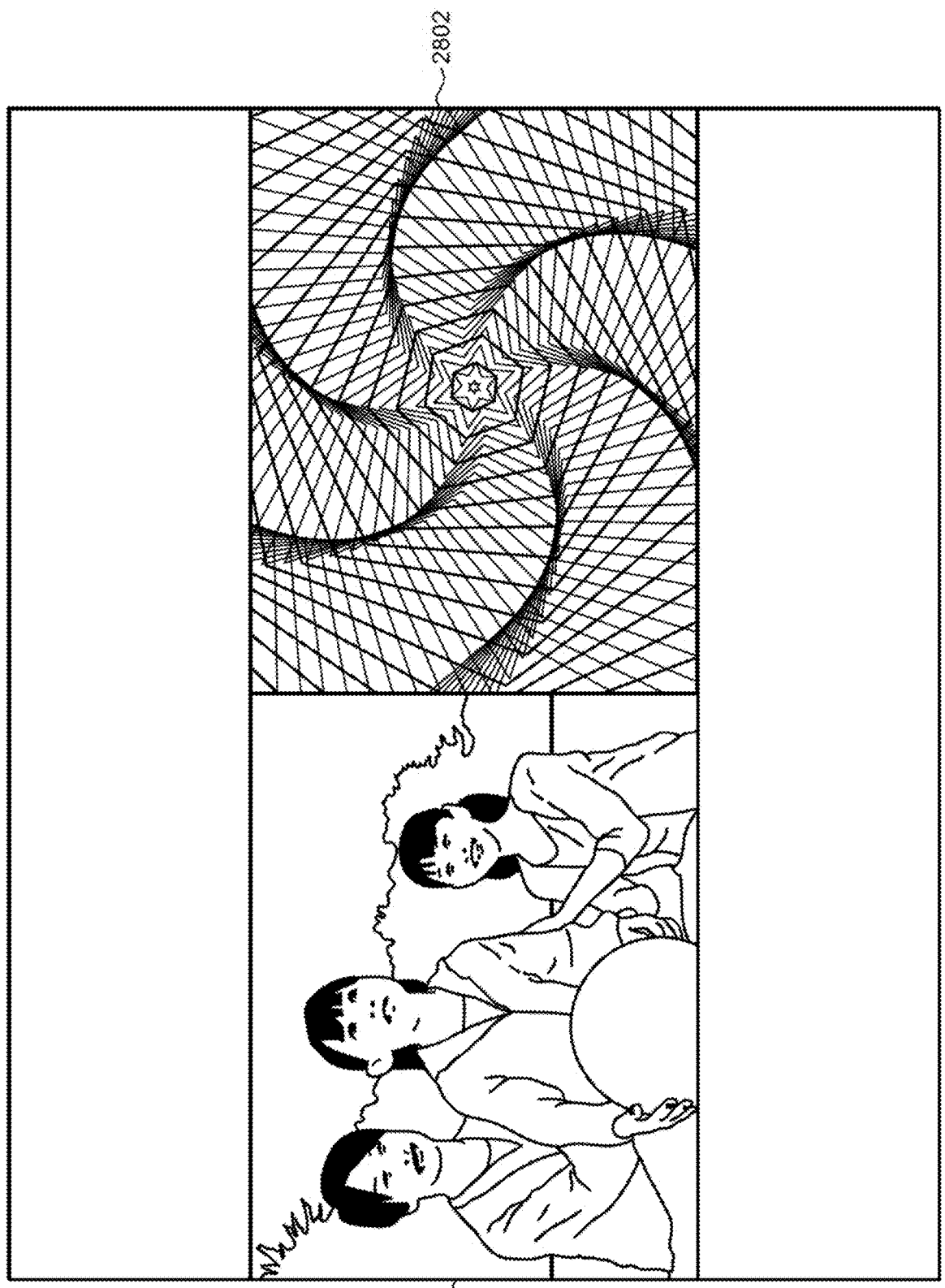
FIG. 44 is a diagram of an exemplary diagnostic image.

FIG. 44 is an exemplary diagnostic image including a geometrical image 2802 and a natural image 2801. The natural image 2801 including three humans against the open space and trees in the park is schematically illustrated in FIG. 44. The image in FIG. 44 does not indicate the color. However, for example, the back ground of the geometric pattern may be green according to the green color of the forest and the grass of the park in the background.

The arrangement of the geometrical image in the left and the natural image in the right in FIGS. 39 to 41 is switched in that in FIGS. 42 to 44. Accordingly, when a plurality of diagnostic images is used, for example, any one of the diagnostic images in FIGS. 39 to 41 and any one of the diagnostic images in FIGS. 42 to 44 may be sequentially displayed.

Figure 45A:
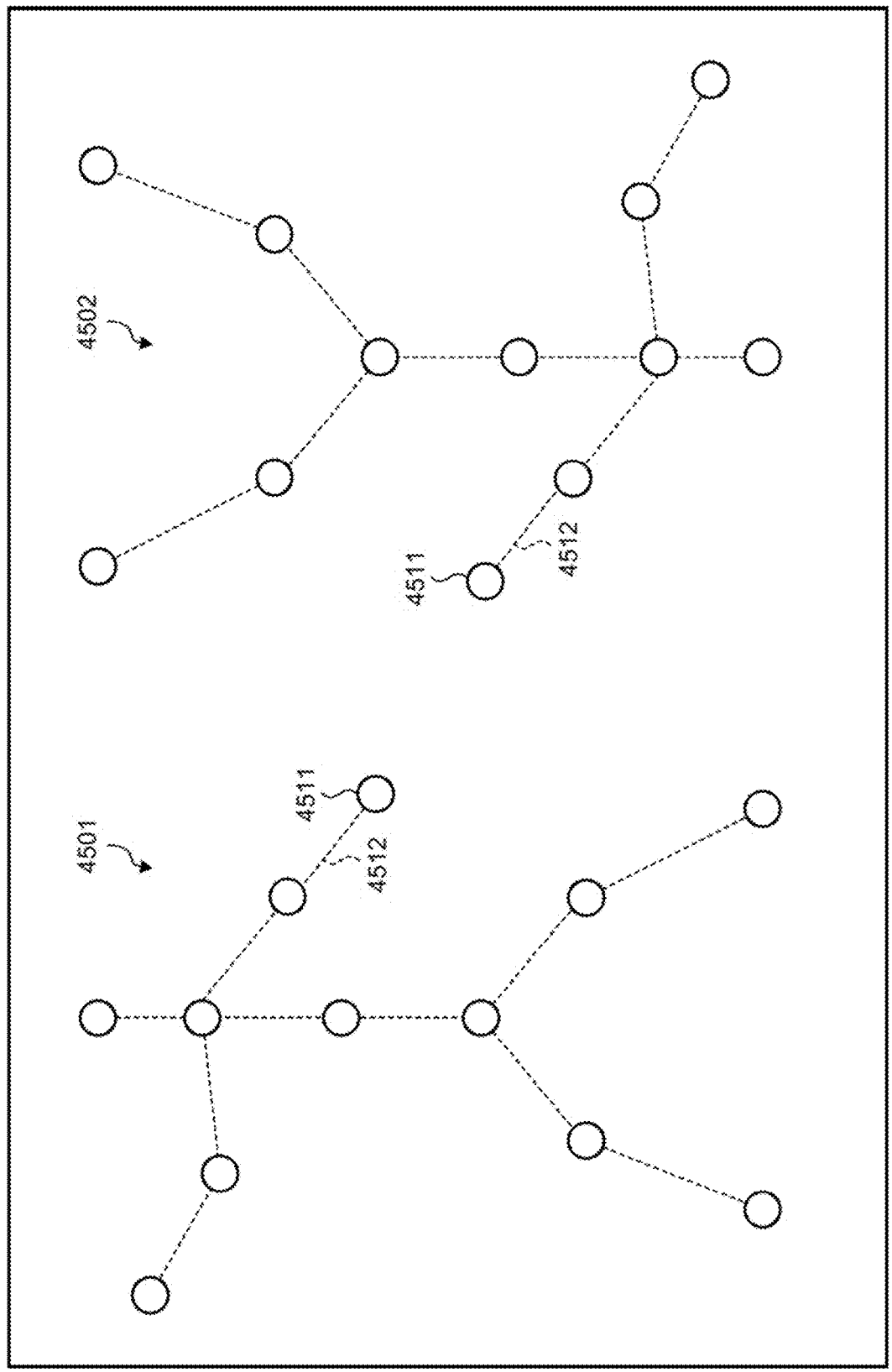
FIG. 45A is a diagram of an exemplary diagnostic image.
Figure 45B:
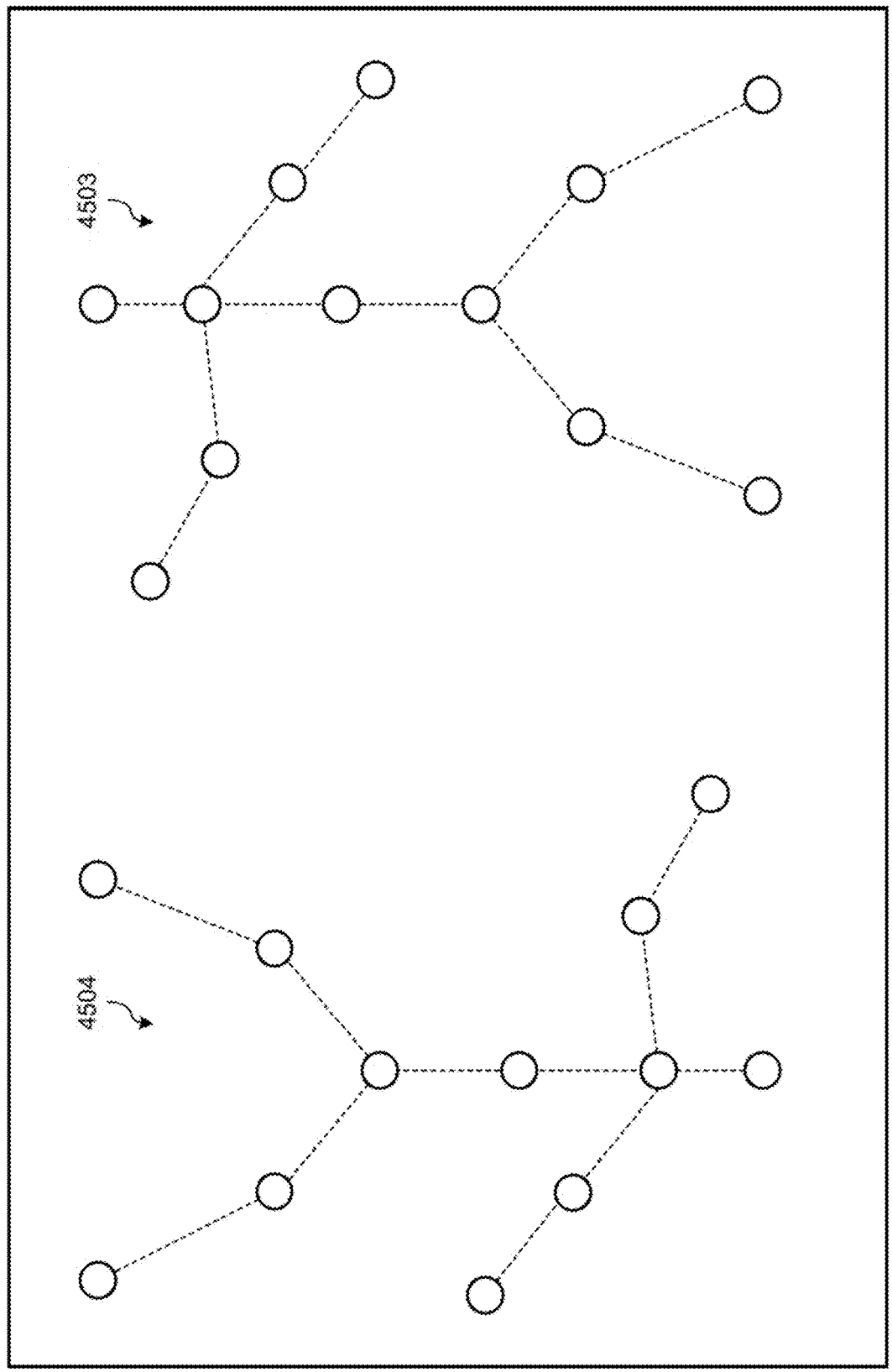
FIG. 45B is a diagram of an exemplary diagnostic image.

Next, another example of the diagnostic image will be described. FIGS. 45A and 45B are diagrams of exemplary diagnostic images. FIG. 45A is an exemplary diagnostic image including a first object 4501 and a second object 4502. The first object 4501 is a moving image in which a shape of the human is expressed with dots 4511. The second object 4502 is an image in which a shape of the human is expressed upside down (rotate by 180 degrees) with the dots.

The second object 4502 is not limited to the shape which is upside down of the human. It is preferable that the second object 4502 is a moving image rotated in a direction other than the correct direction. A moving image in which the first object 4501 is reversely reproduced (operated in a reverse order) and rotated may be used as the second object 4502. This is to evaluate the degree of the developmental disorder by using the tendency that the non-handicapped person pays attention to the moving image of the shape of the human in the correct direction. For example, the evaluation unit 359 calculates the evaluation value to be lower as the index regarding the degree of the developmental disorder when the moving image of the shape of the human in the correct direction attracts attention. Dotted lines 4512 connecting the dots 4511 are illustrated in the drawings. However, the dotted line 4512 is not actually displayed.

The output controller 354 outputs the voice from the speaker 105, and at the same time, the output controller 354 displays the first object 4501 which is the moving image shaped like the human for moving according to the voice on the display 210. At the same time, the second object 4502 is displayed on the display 210. The second object 4502 is the moving image shaped like the human turned upside down which moves without corresponding to the music. The output controller 354 may display the second object 4502 on the display 210 as an object which moves in a reverse order with respect to the first object 4501 and in which the first object 4501 is rotated by 180 degrees. The second object 4502 reproduces the music, for example, music well known to the infants from the speaker 105, and at the same time, may display the moving image in which the shape of the human dancing with the music is expressed by the dots 4511. A moving image indicating the movement of radio gymnastics may be displayed together with the music of the radio gymnastics. According to this, the non-handicapped person can pay more attention to the moving image in the correct direction. The moving image has the music and the movement similar to those familiar to that person.

A plurality of the diagnostic images as FIG. 45A may be used to for the analysis. In this case, a plurality of diagnostic images having different arrangements of the moving images in the correct direction from each other may be used. For example, the diagnostic image including the moving image in the correct direction and the reversed moving image arranged in the first direction relative to the moving image is used. After that, the diagnostic image including the moving image in the correct direction and the reversed moving image arranged in the second direction (for example, reverse direction of the first direction), which is different from the first direction, relative to the moving image may be used. Accordingly, the diagnosis accuracy can be improved. The first direction is, for example, a right direction of the display 210. For example, when two diagnostic images are used, a first diagnostic image including a first object 4501 shaped like a human for moving according to the voice as illustrated in FIG. 45A and a second object 4502 in which the first object 4501 for moving according to the voice is rotated is displayed on the display. After that, a second diagnostic image including a third object 4503 which is a moving image shaped like a human for moving according to the voice as illustrated in FIG. 45-2 and a fourth object 4504 which is a moving image arranged in the second direction different from the first direction relative to the third object and which is the image of the rotated third object 4503 is displayed on the display 210. The second direction is, for example, a left direction of the display 210. In the first and second diagnostic images, the objects on the right and left for moving with the voice may be switched with each other. The third object is a shape like the human expressed by the dots, and the dots move like dancing according to the music. The fourth object is an image of a shape like the human turned upside down (rotate by 180 degrees) which is expressed by the dots, and the movements of the dots do not correspond to the music.

Figure 46:
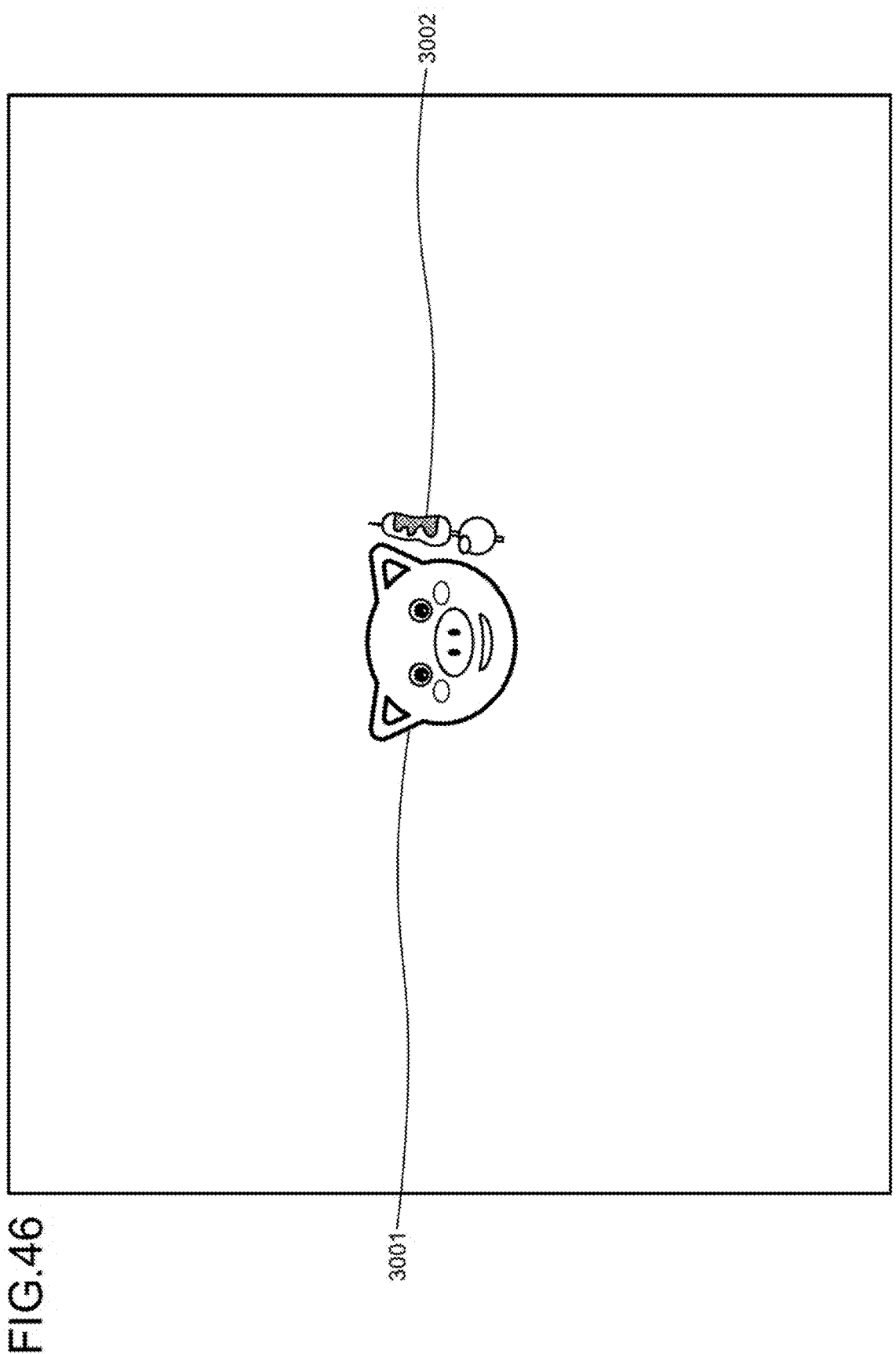
FIG. 46 is a diagram of an exemplary eye-catch image.
Figure 47:
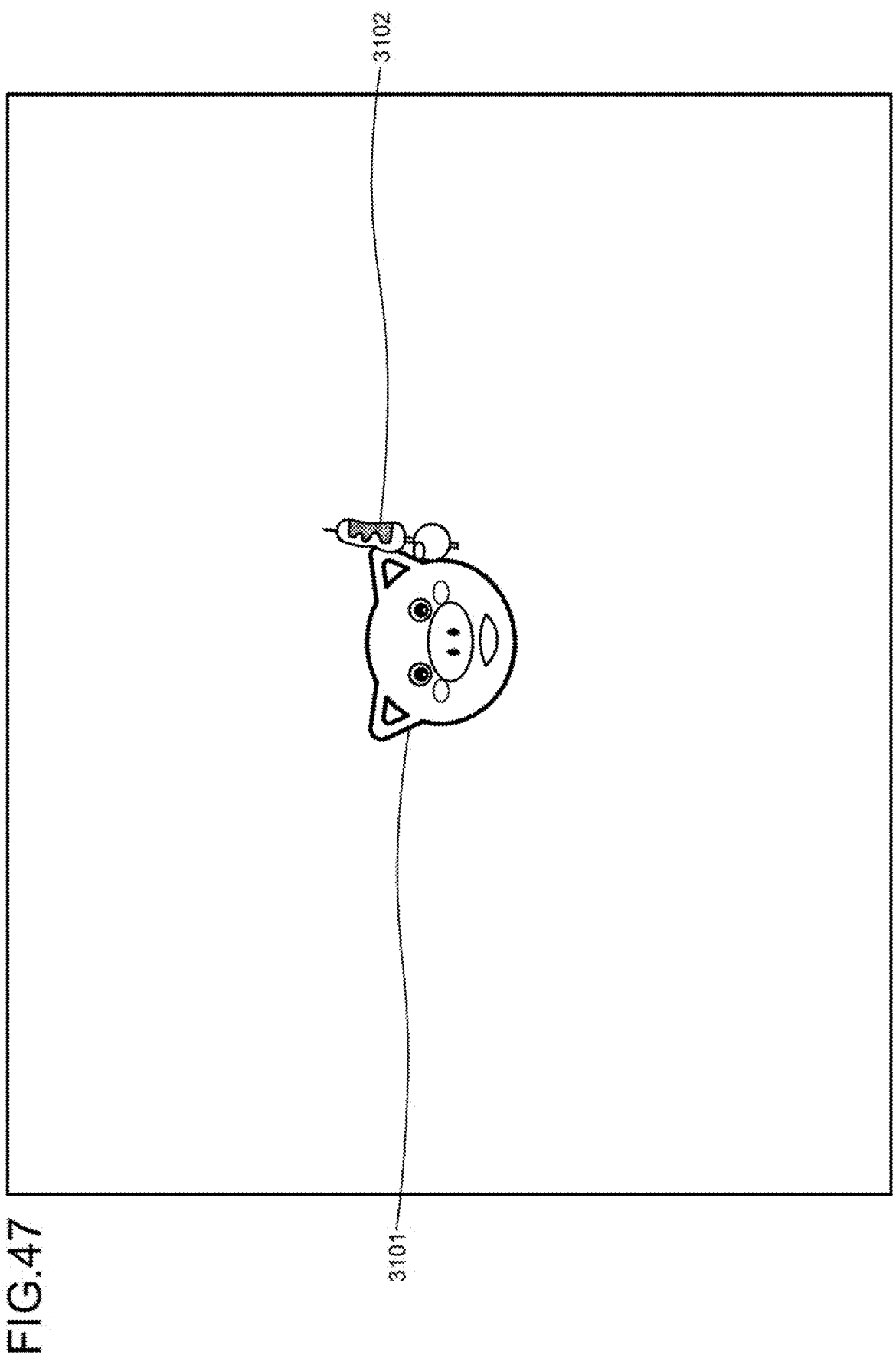
FIG. 47 is a diagram of an exemplary eye-catch image.
Figure 48:
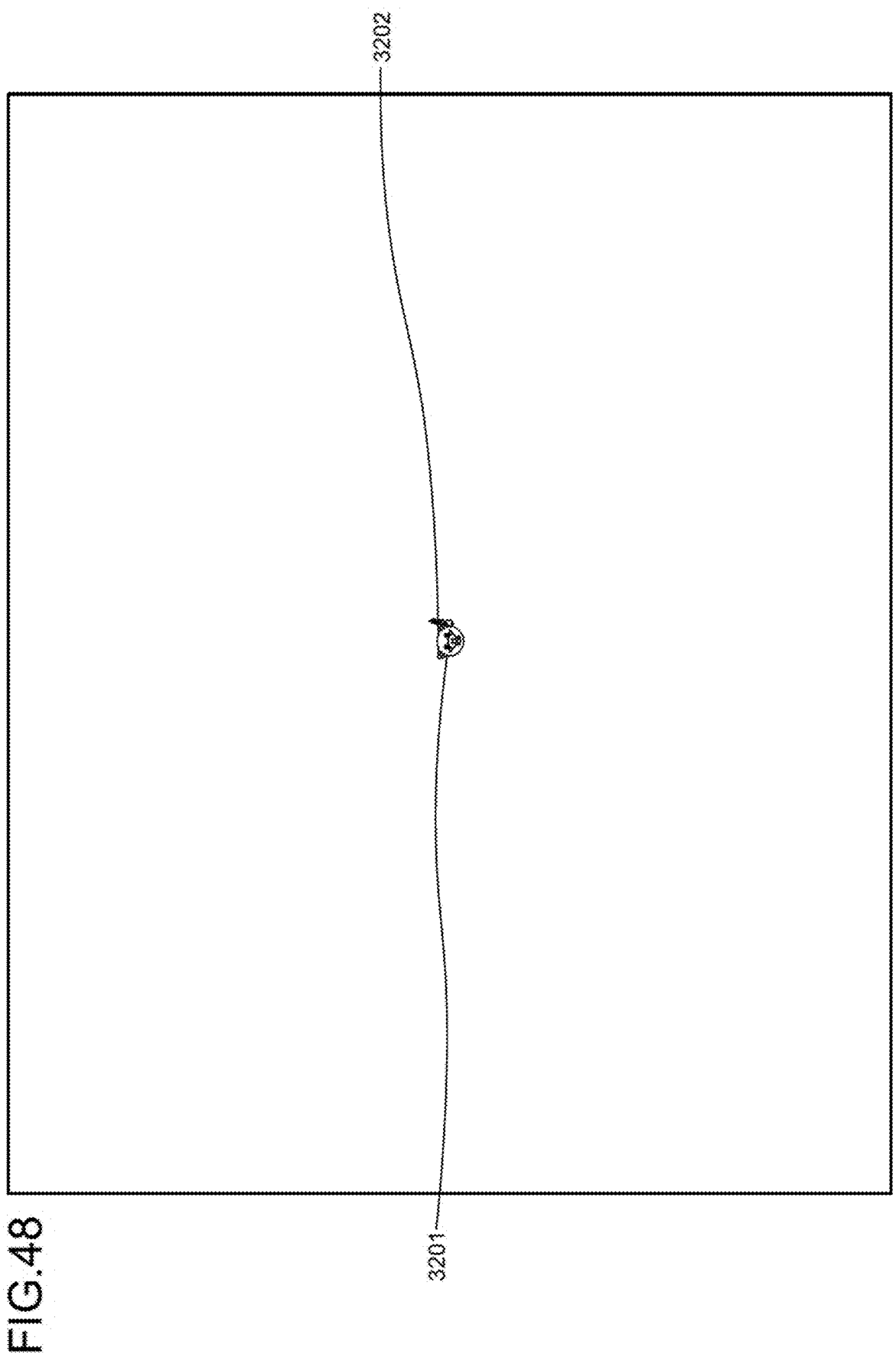
FIG. 48 is a diagram of an exemplary eye-catch image.

Next, the example of the eye-catch images displayed before/after the display of the diagnostic image will be described. The eye-catch image represents an image displayed to attract attention of the subject (image before the diagnosis). FIGS. 46 to 48 are diagrams of exemplary eye-catch images. As illustrated in FIG. 46, the eye-catch image including a face of the character 3001 and a food 3002 held by the character is displayed at a position attracting the attention of the subject (center of the display screen 101 in the example in FIG. 46). The output controller 354 displays the eye-catch image as illustrated in FIG. 46 to attract the attention of the subject, for example, before displaying the diagnostic image.

The output controller 354 may display the background of the diagnostic image and the background of the eye-catch image in different display modes from each other. For example, the background of the diagnostic image may be displayed in a different color from that of the background of the eye-catch image. This allows the subject to easily recognize that the image is switched to the different one. This can make the subject pay more attention to the display screen 101. The display mode is not limited to the color. For example, the display mode may be the color tone and the brightness.

As the eye-catch image, the output controller 354 may display the moving image for moving to be decreased in size having a specific position (for example, a position to attract attention) as a center. Also, the output controller 354 outputs the voice by the speaker 105 and at the same time may display the eye-catch image which moves according to the voice. For example, a voice such as "look! look!" for calling the subject is output, and at the same time, the eye-catch image may be displayed. This can make the subject pay attention to the specific position in the display screen 101. As a result, the point of view of the subject can be accurately detected at the time of the analysis processing, and the analysis (diagnosis) accuracy can be improved.

After the eye-catch image has been moved according to the voice, the output controller 354 may display the eye-catch image so as to be decreased in size having the specific position as the center. FIG. 47 is an exemplary eye-catch image after the eye-catch image in FIG. 46 has been moved. FIG. 48 is an exemplary eye-catch image (face 3201 and food 3202) after the eye-catch image has been decreased in size. The output controller 354 may display a part of the image in the frame so as to move it according to the voice. For example, the food 3102 may be moved without moving the face of the character 3101. FIG. 47 is an exemplary image in which a nose part of the character changes. When the part close to the center of the image is moved, this can make the subject pay attention to the position closer to the center.

Figure 49:
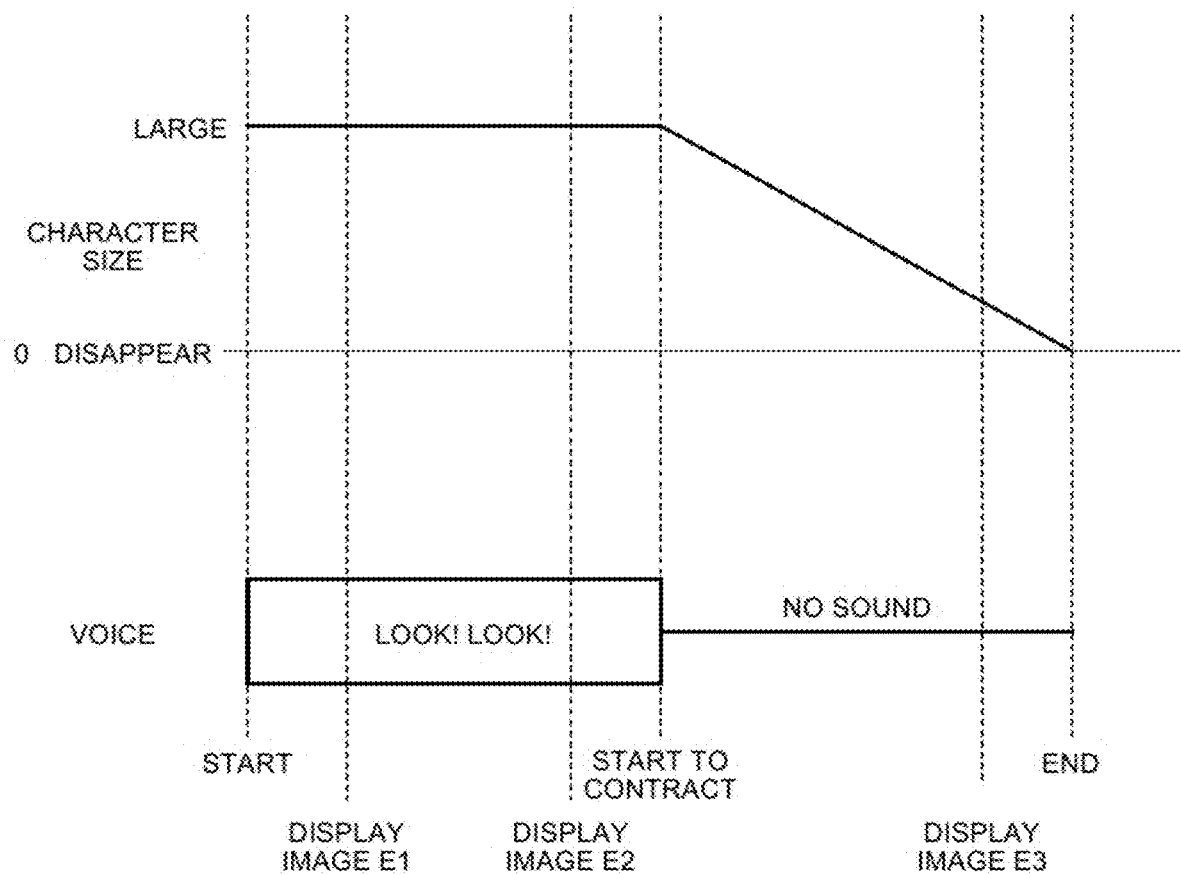
FIG. 49 is a diagram of timings of a display of the eye-catch image and a voice output.

FIG. 49 is a diagram of exemplary timings of the display of the eye-catch image and the voice output. In the example in FIG. 49, the output controller 354 displays the eye-catch image of the larger character. At the same time, the output controller 354 starts to output the voice for calling the subject such as "look! look!". The output controller 354 may use the image for moving according to the voice (moving image) as the eye-catch image. In this case, for example, the eye-catch image in FIG. 46 is displayed at a timing described as "DISPLAY IMAGE E1" in FIG. 49. Also, for example, the eye-catch image in FIG. 47 is displayed at a timing described as "DISPLAY IMAGE E2".

When the voice output has ended, the output controller 354 starts to contract the eye-catch image. When the display of the eye-catch image is contracted, the output controller 354 may not output voice (no voice). The output controller 354 continues to display the contracted eye-catch image until the size of the image becomes zero. For example, the eye-catch image in FIG. 48 is displayed at a timing described as "DISPLAY IMAGE E3" in FIG. 49.

Next, the result display screen and the processing for outputting the result will be described in detail. As described above, for example, when the result display button 502 on the menu screen is pressed, the output controller 354 displays the result display screen on the display 210. FIGS. 51 to 54 are diagrams of exemplary result display screens.

The output controller 354 may display a different result display screen for each subject of which the evaluation result is output. For example, the output controller 354 may display the result by a specified result display method which is one of a result display method for outputting the result to the subject and a result display method for outputting the result to the diagnosing person (doctor and the like). For example, the result may be displayed relative to the subject by the result display method for displaying the subject's evaluation result. Also, the result may be displayed relative to the diagnosing person by the result display method for displaying a plurality of evaluation results relative to a plurality of subjects. The convenience can be improved by switching the display methods according to the subject in this way.

A specifying method for specifying a result display method for displaying the result by the output controller 354 can be voluntarily selected. However, for example, methods below can be applied, i.e., a method for determining the result display method by storing the specifying method of the result display method in an external file (INI file and the like) and referring to the stored specifying method, a method for adding a function for specifying the result display method to be displayed on the menu screen, and a method for switching the specifying method according to an authority of the subject authenticated by a login authentication function.

Figure 50:
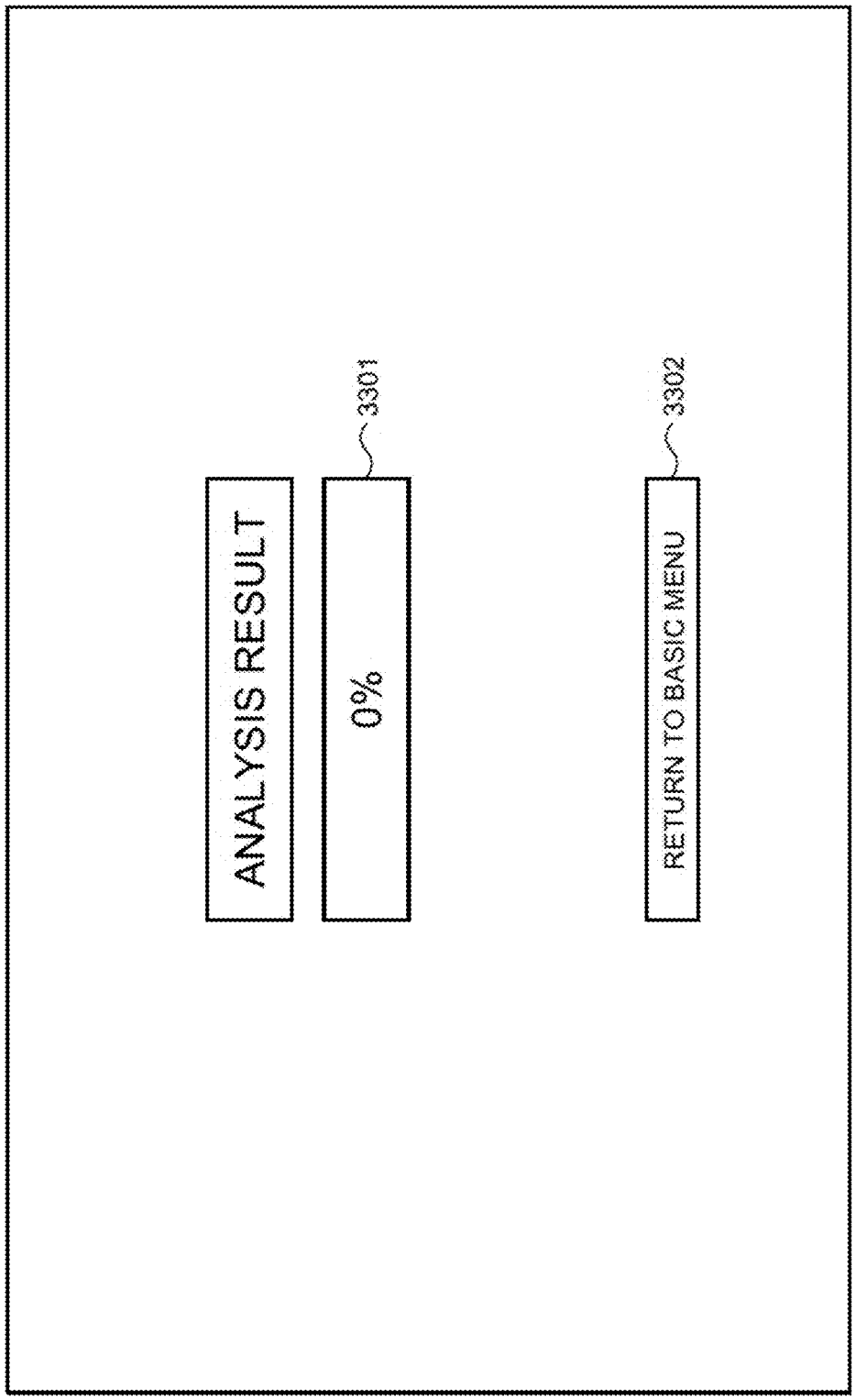
FIG. 50 is a diagram of an exemplary result display screen.

FIG. 50 is an exemplary result display screen to be output to the subject. As illustrated in FIG. 50, the result may be displayed relative to the subject by the result display method for displaying the evaluation result (analysis result) regarding the subject. In FIG. 50, an example is illustrated in which the evaluation value is displayed in an analysis result output column 3301 in percentage terms. The evaluation value is an index regarding the degree of the developmental disorder calculated by the evaluation unit 359. When the return to basic menu button 3302 is pressed, for example, the menu screen as illustrated in FIG. 16 is displayed. The evaluation unit 359 calculates the evaluation value based on the plurality of evaluation items. The evaluation unit 359 determines whether to calculate the evaluation value higher/lower with respect to each of the plurality of evaluation items described above. Then, the evaluation unit 359 outputs the determined values to the analysis result output column 3301 as final evaluation values. The evaluation unit 359 may give the evaluation value as a point to each evaluation item.

As illustrated in FIG. 50, instead of displaying the evaluation result on the display 210 or while displaying the evaluation result on the display 210, the output controller 354 may be configured to output a recording media, such as paper where the evaluation result is printed, from the printer 324.

Figure 51:
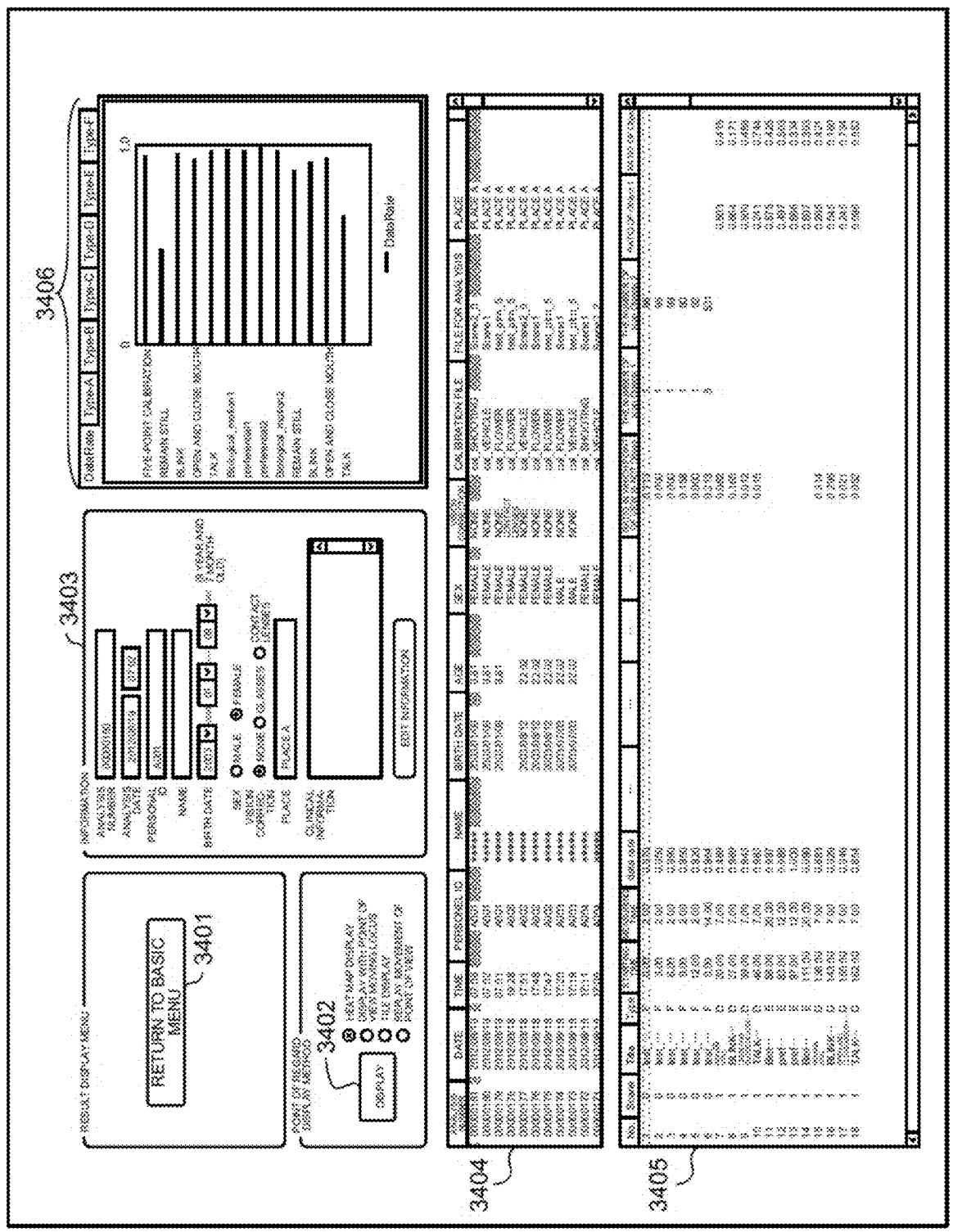
FIG. 51 is a diagram of an exemplary result display screen.

FIGS. 51 to 54 are exemplary result display screens to be output to the diagnosing person. As illustrated in FIG. 51, the result may be displayed relative to the diagnosing person by the result display method for displaying a plurality of evaluation results relative to a plurality of subjects. The result display screen in FIG. 51 includes a return to basic menu button 3401, a display button 3402, an information display column 3403, a subject list 3404, an evaluation item list 3405, and a result display column 3406.

Figure 55:
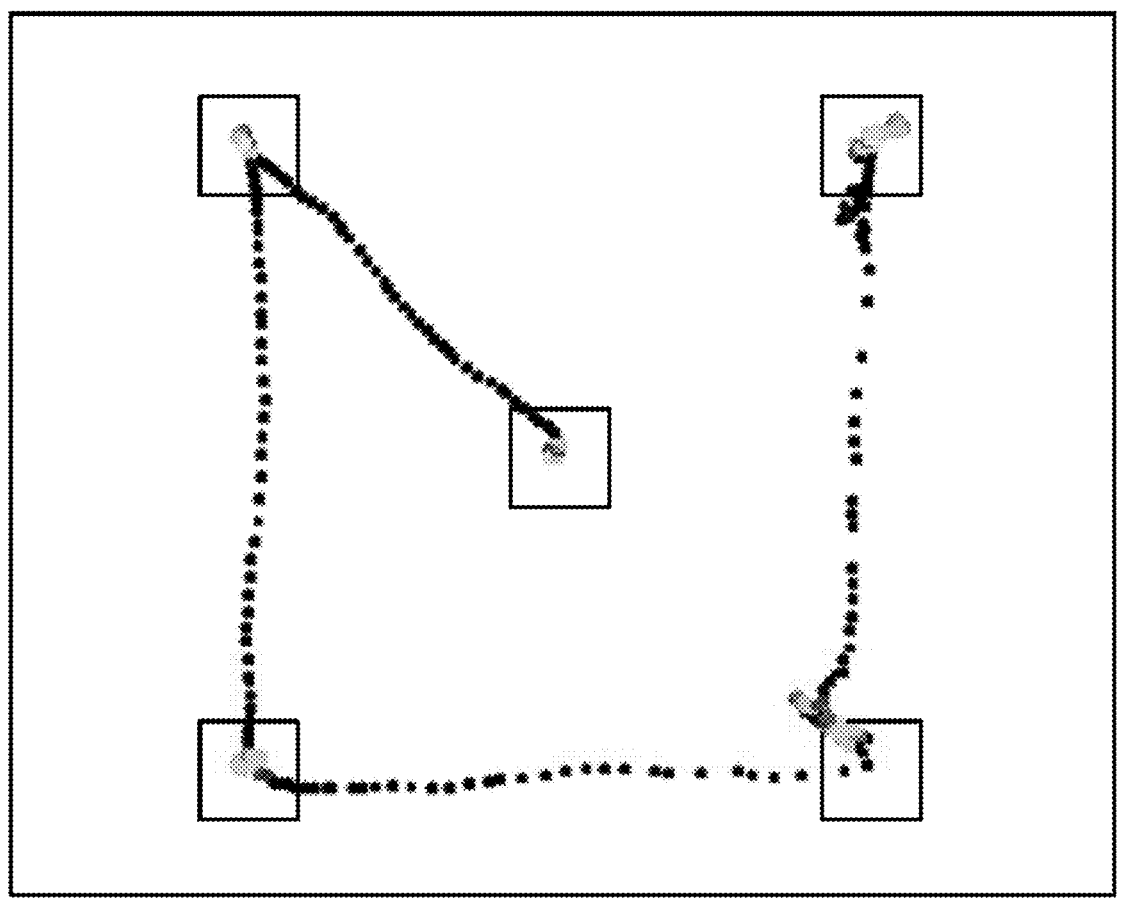
FIG. 55 is a diagram of an exemplary display system of the point of regard.
Figure 56:
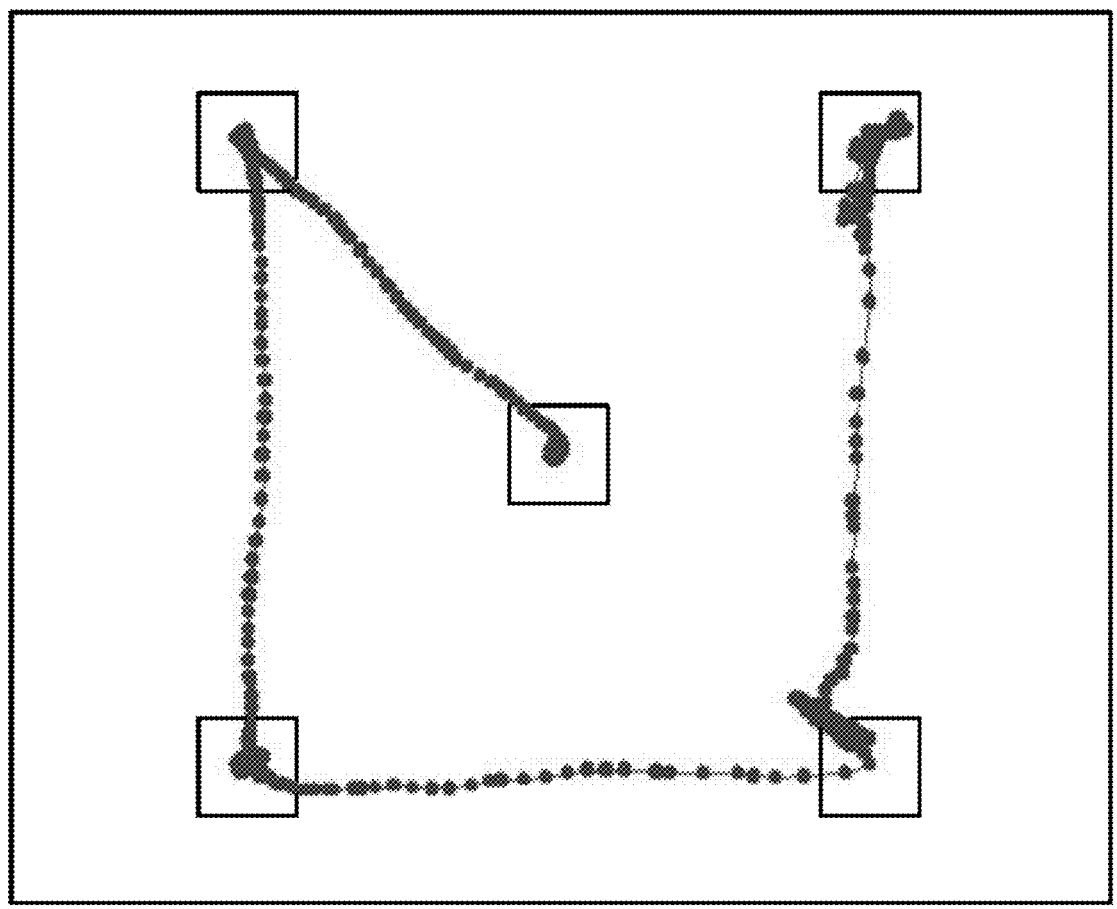
FIG. 56 is a diagram of an exemplary display system of the point of regard.
Figure 57:
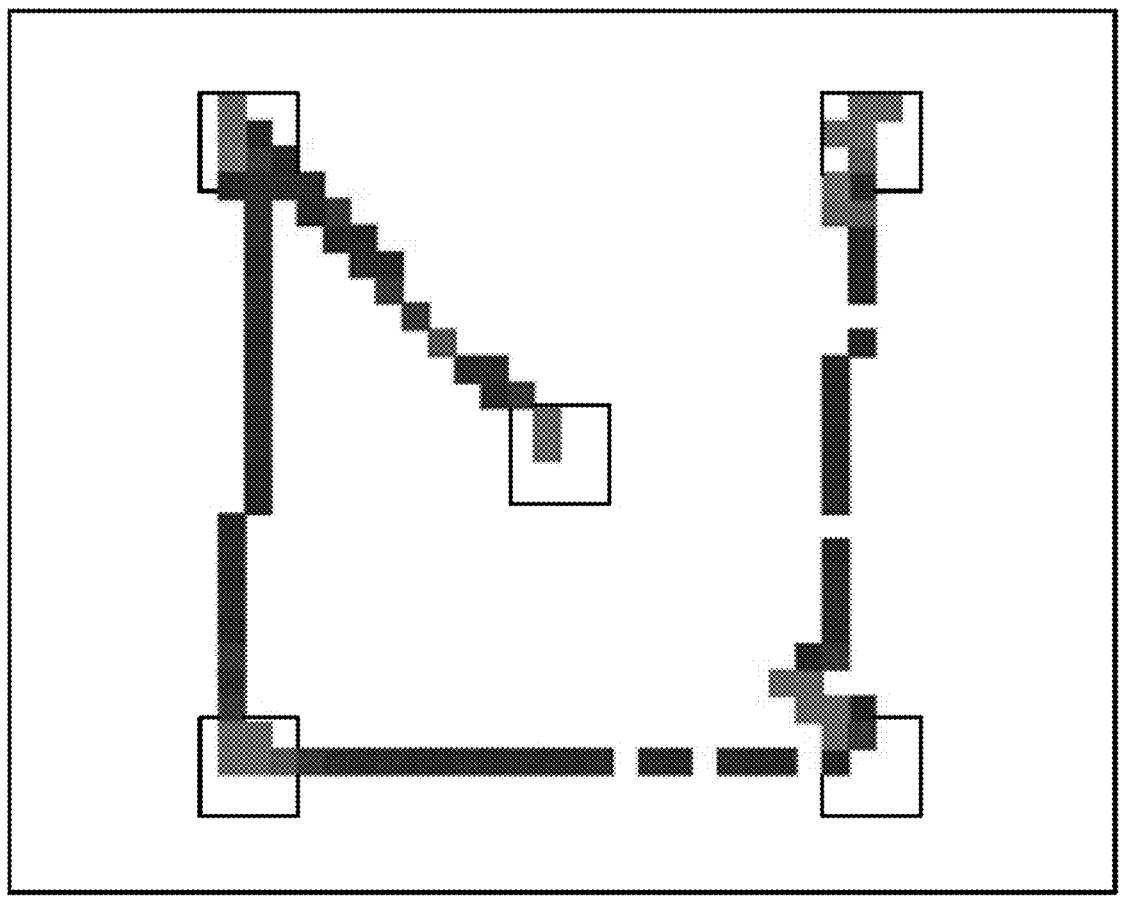
FIG. 57 is a diagram of an exemplary display system of the point of regard.
Figure 58:
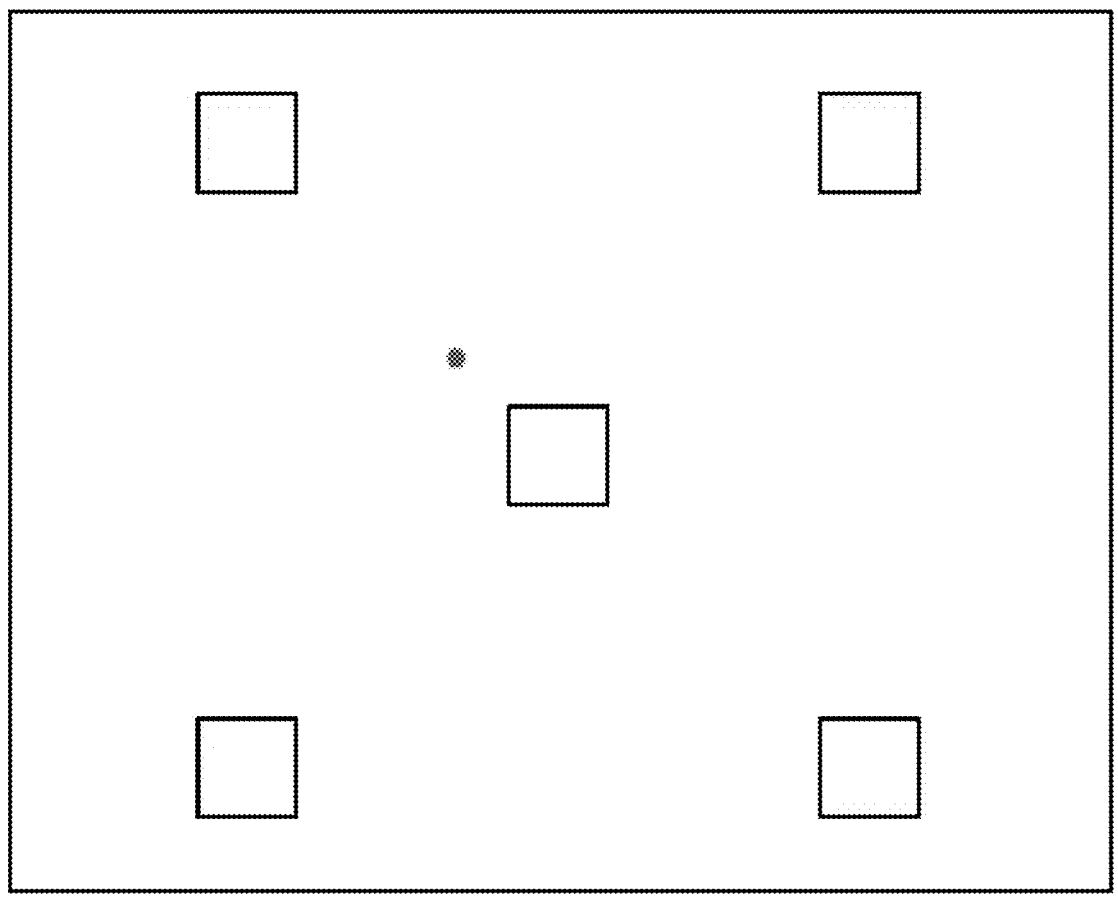
FIG. 58 is a diagram of an exemplary display system of the point of regard.

When the return to basic menu button 3401 is pressed, for example, the menu screen as illustrated in FIG. 16 is displayed. When the point of regard display button 3402 to display the point of regard is pressed, the detected point of regard is displayed according to a display system selected by a radio button which is on the right of the point of regard display button 3402. As the display system of the point of regard which can be selected, for example, "heat map display", "display with the point of view moving locus", "tile display", and "replay the movement of the point of view" can be exemplified. "Heat map display" is a display system in which the lines of sight of the subject detected in a certain period of time are plotted on the screen as illustrated in FIG. 55. When the coordinates are overlapped, the output controller 354 displays them by changing their color in the order of "blue→green→yellow→orange→red". "Display with the point of view moving locus" is a display system in which the lines of sight of the subject detected in a certain period of time are plotted on the screen as illustrated in FIG. 56 and the temporally continuous points are connected with a line. "Tile display" is a display system in which the color of the block where the point of regard has been detected is changed according to the number of the detected points of regard included in the block having a fixed area as illustrated in FIG. 57. For example, the output controller 354 displays them by changing their color in the order of "blue→green→yellow→orange→red" according to the number of the detected points of regard. "Replay the movement of the point of view" is a display system in which the movement of the points of regard of the subject is reproduced by the moving image. For example, the point of regard is indicated by a small circle as illustrated in FIG. 58.

The information display column 3403 is a column where information on the currently selected subject is displayed. For example, the information input in the information input column 613 on the analysis menu screen in FIG. 17 and an analysis date are displayed in the information display column 3403. When an information editing button is pressed, an editing screen (not illustrated) to edit the displayed information may be displayed.

The subject list 3404 is a region to display the subjects so that the subjects can be selected (first region). An example is illustrated in FIG. 51 in which the subject corresponding to a first row from the top has been selected. The evaluation item list 3405 is a region where the evaluation items used for the analysis are displayed so that the items can be selected (second region). For example, one or more evaluation items displayed relative to the subject selected in the subject list 3404 are displayed in the evaluation item list 3405. Each evaluation item is numbered (No.) in the evaluation item list 3405. Each evaluation item corresponds to a scene in a series of the diagnostic images (moving image) (Scene), a title (Title), a kind of the evaluation method such that the point of view of which region in the diagnostic image is evaluated (Type), a starting time of the evaluation item in the series of the diagnostic images (moving image), a measuring time of the evaluation item, and a data acquisition rate indicating a ratio in which the point of regard is detected in the diagnostic image during the measuring time (data rate). Also, in the evaluation item list 3405 of this example, a ratio in which the point of view is detected outside the evaluation region (ratio in which the point of view is not Object), the number of the detections of the points of view in the evaluation region of an Object 1 (the number of Scan Objects 1), the number of the detections of the points of view in the evaluation region of an Object 2 (the number of Scan Objects 2), a ratio in which the point of regard is detected in the evaluation region of the Object 1 (ratio of Object 1), and a ratio in which the point of view is detected in the evaluation region of the Object 1 (ratio of Object 2) are displayed.

As a kind of the evaluation method Type, for example, the Object 1 is eyes and the Object 2 is a mouth in Type-D. In Type-E, the Object 1 is a left half of the diagnostic image and the Object 2 is a right half of the diagnostic image. The diagnosis assisting apparatus 100 stores the series of diagnostic images (moving image) while corresponding the images to what kind of the evaluation is performed in which part of the reproducing time. The diagnosis assisting apparatus 100 displays the series of diagnostic images as an evaluation list. The ratio in which the point of view is detected in the evaluation region of the Object 1 or 2 is calculated as follows. The diagnosis assisting apparatus 100 detects the points of regard, for example, 50 times per second. For example, when a measuring time of the evaluation item is four seconds, the points of regard are detected 200 times. When the number of the detections of the points of regard in the diagnostic image is 180 times and the number of the detections of the points of regard in the evaluation region of the Object 1 is 54 times and that in the evaluation region of the Object 2 is 108 times, the following equations are satisfied, (data rate)=0.900, (ratio in which the point of view is not Object)=0.100, (the number of Scan Objects 1)=54, and (the number of Scan Objects 2)=108. Then, the equations (ratio of Object 1)=0.300 and (ratio of Object 2)=0.600 are satisfied. The point of view detecting unit 352 detects the point of view of the subject at least when the diagnostic image is displayed.

The result display column 3406 is a region where the detection result is displayed (third region). In the result display column 3406, the diagnostic image displayed relative to the subject selected from the subject list 3404, for example, the detection result relative to the evaluation item selected from among the evaluation items displayed in the evaluation item list 3405 is displayed. When the evaluation item is not selected, the detection results relative to a plurality of evaluation items may be integrated and displayed. An example in a case where the detection result relative to the plurality of evaluation items are integrated and displayed in this way is illustrated in the result display column 3406 in FIG. 51. Also, the detection results of the other evaluation items having the same Types as that of the evaluation item selected from the evaluation item list 3405 may be integrated and displayed in the result display column.

As illustrated in FIG. 51, the display mode of the evaluation result may be configured to specify from among a plurality of display modes in the result display column 3406. An example is illustrated in FIG. 51 in which any one of seven display modes can be specified by using a selection tab. The seven display modes are "DataRate" and "Type-A" to "Type-F".

Figure 52:
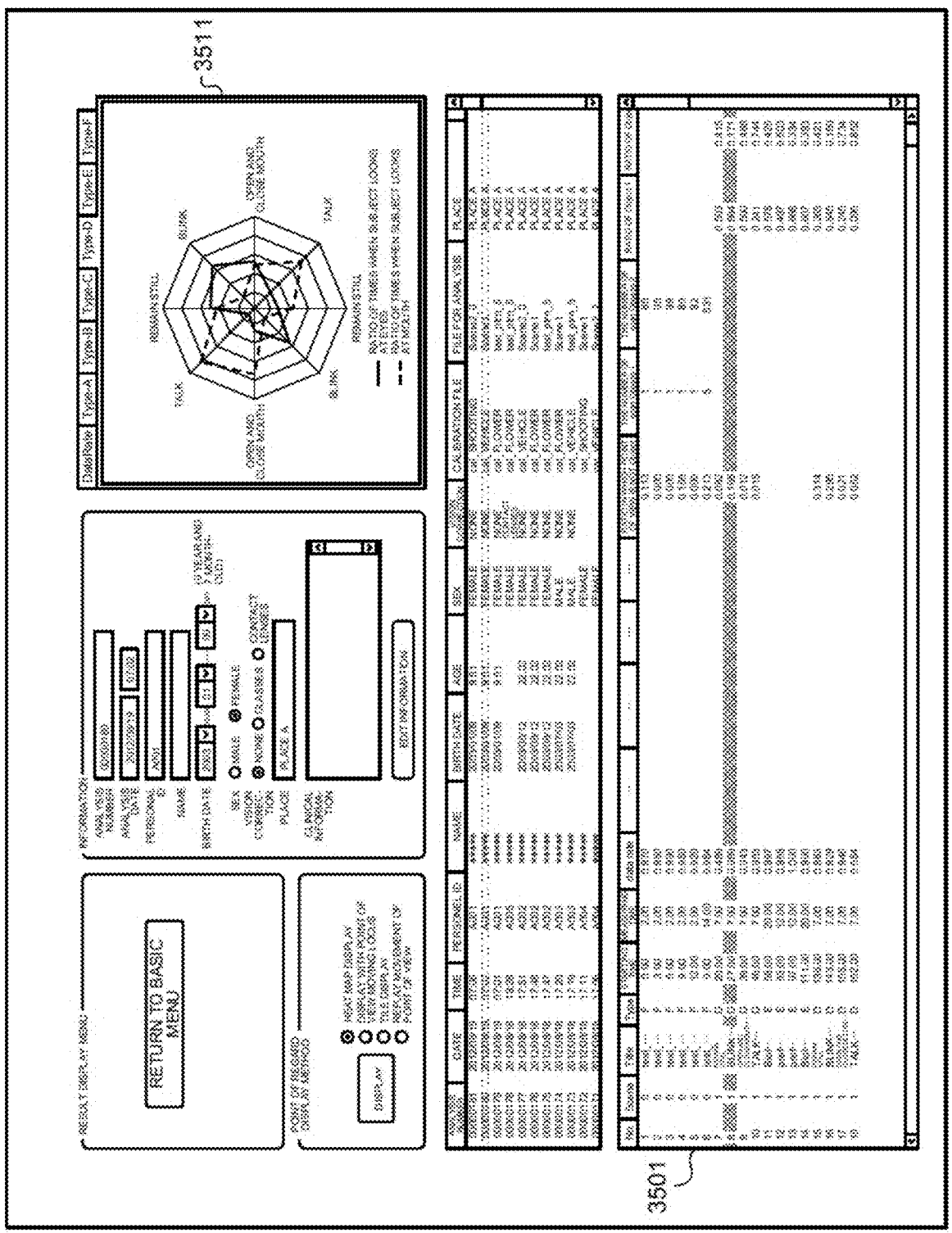
FIG. 52 is a diagram of an exemplary result display screen.

FIG. 52 is an exemplary result display screen in a case where "Type-D" has been specified. In FIG. 52, an example of a result display column 3511 is illustrated in which the evaluation result according to the plurality of evaluation items corresponding to Type-D has been graphed. In this way, the plurality of evaluation items having the common kind (Type) may be integrated and displayed in the result display column. The kinds of the evaluation items are displayed in a column of "Type" in the example of the evaluation item list 3501 in FIG. 52.

Figure 53:
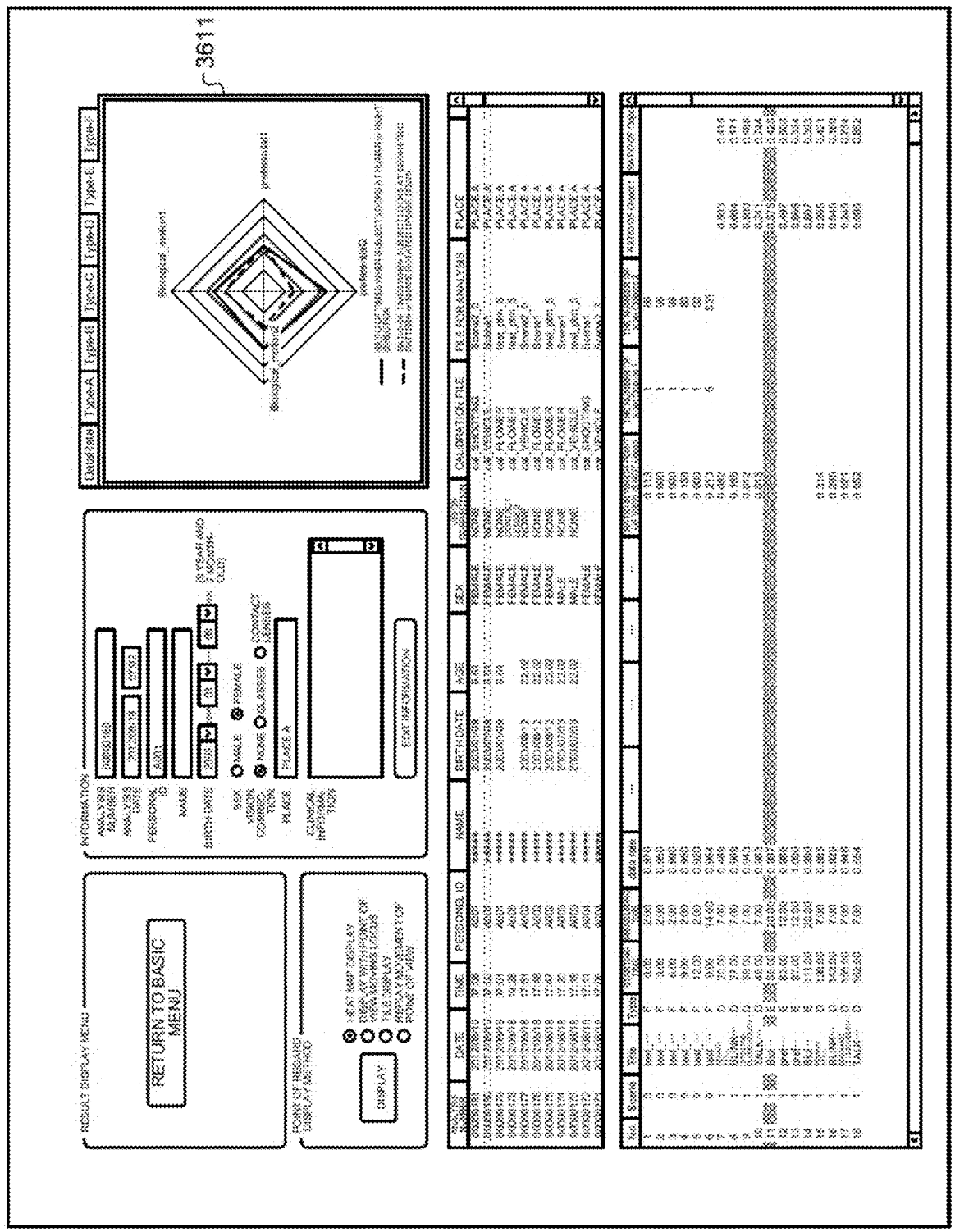
FIG. 53 is a diagram of an exemplary result display screen.

FIG. 53 is an exemplary result display screen in a case where "Type-E" has been specified. In FIG. 53, an example of a result display column 3611 is illustrated in which the evaluation result according to the plurality of evaluation items corresponding to Type-E is graphed.

Figure 54:
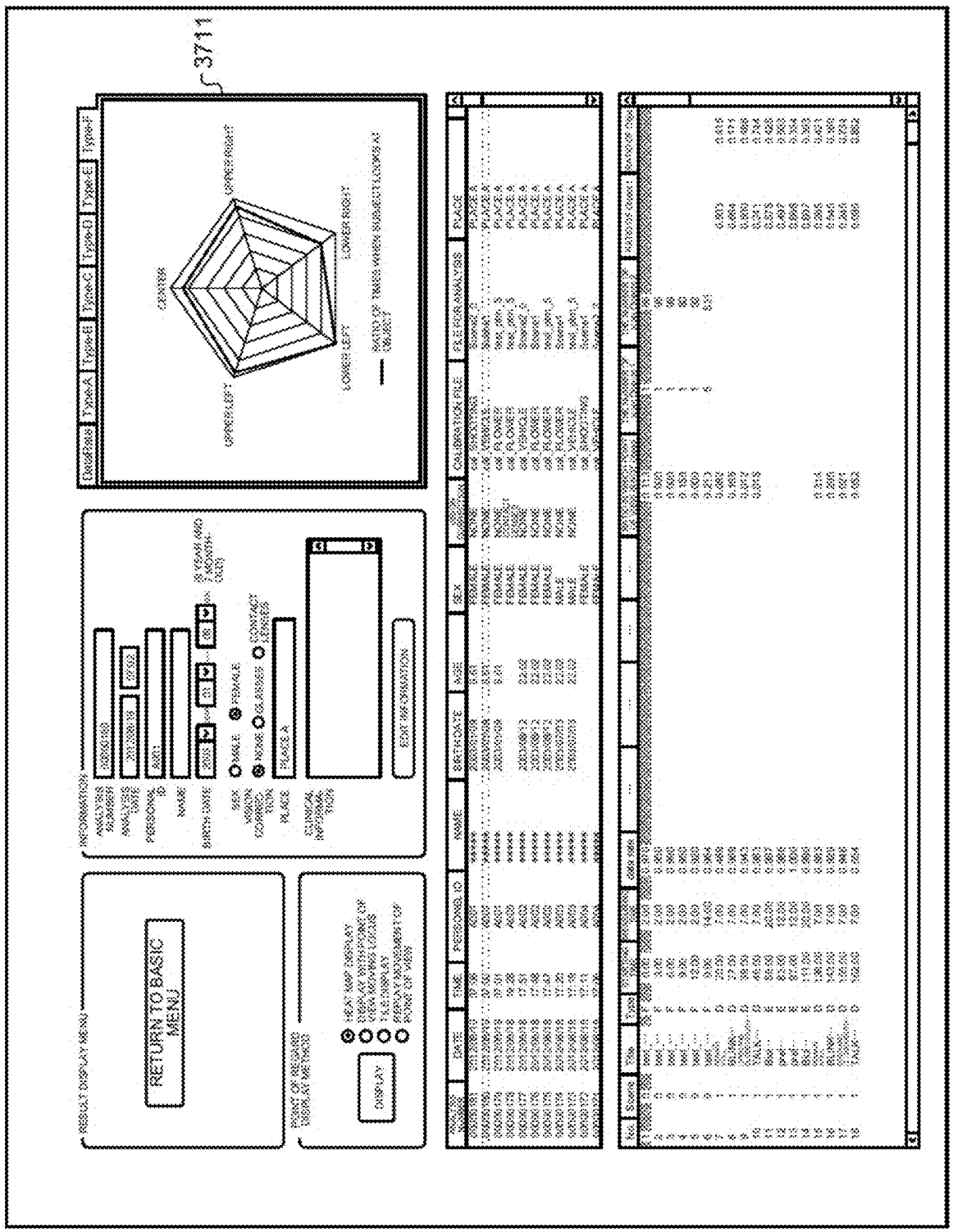
FIG. 54 is a diagram of an exemplary result display screen.

FIG. 54 is an exemplary result display screen in a case where "Type-F" has been specified. In FIG. 54, an example of a result display column 3711 is illustrated in which the evaluation result according to the plurality of evaluation items corresponding to Type-F is graphed.

When at least one of the subject selected in the subject list and the evaluation item selected in the evaluation item list is changed, the output controller 354 may be configured to display the evaluation result corresponding to the changed subject and the changed evaluation item in the result display column. In the present embodiment, a column where the subject is selected in this way (subject list), a column where the evaluation item is selected (evaluation item list), and the result display column are displayed in a single screen. When the selected subject and the selected evaluation item are switched, the evaluation result to be displayed in the result display column is switched to the evaluation result corresponding to the changed subject and evaluation item. Accordingly, the diagnosing person can display the desired evaluation result with an easy operation.

For example, the following advantageous effects can be obtained according to the present embodiment as described above.

(1) Since the image used for the calibration, the image used to detect the point of regard for correction, and the diagnostic image are displayed in this order, each processing necessary for the diagnosis is smoothly performed. Accordingly, the diagnosis accuracy can be improved.

(2) Since the diagnosis can be performed by using the diagnostic image including the natural image and the geometrical image similar to the natural image, the possibility that the non-handicapped person regards the geometrical image by mistake can be reduced. Accordingly, the diagnosis accuracy can be improved.

(3) Since the image indicating the eye is displayed relative to the scale indicating the appropriate position, the subject can adjust the position of the subject by determining whether the position relative to the camera is correct. Also, since the moving image is displayed in the image corresponding to the reference region for representing the range of the appropriate positions of the eyes, this can make the subject pay attention to the display screen and appropriately adjust the position of the subject. Accordingly, the diagnosis accuracy can be improved.

(4) Since a plurality of images different from each other is used as an image used to detect the point of regard for correction, this can make the subject to pay attention to the image while preventing the subject from getting bored. Accordingly, the diagnosis accuracy can be improved.

(5) Since the diagnostic image including the moving image shaped like a human in the correct direction for moving according to the voice and the moving image in the incorrect direction is used, the non-handicapped person pays more attention to the moving image in the correct direction. Accordingly, the diagnosis accuracy can be improved.

(6) Since the background of the diagnostic image and the background of the eye-catch image displayed to attract subject's attention are displayed in different display modes from each other, the subject can easily recognize that the image is switched to a different image. As a result, this can make the subject pay attention to the display screen, and the diagnosis accuracy can be improved.

(7) Since the eye-catch image, which is an image before the diagnosis decreased in size having the specific position as the center after being moved according to the voice, is displayed on the display before the diagnostic image is displayed, this can make the subject pay attention to the specific position on the display screen while creating a quiet and comfortable situation where the doctor easily diagnoses just before the start of the diagnostic image display as attracting the subject's attention first. As a result, the point of view of the subject can be accurately detected at the time of the analysis processing, and the diagnosis accuracy can be improved.

(8) The result display screen where the evaluation result is displayed can be switched according to the subject to whom the evaluation result is output. Accordingly, the convenience of the operator can be improved.

(9) The column where the subject is selected, the column where the diagnostic image is selected, and the result display column are displayed in a single screen. When the selected subject and the selected diagnostic image are switched, the evaluation result displayed in the result display column is switched to the evaluation result corresponding to the changed subject and diagnostic image. Accordingly, the diagnosing person can display the desired evaluation result with an easy operation, and the convenience of the diagnosing person can be improved.

The present embodiment includes the following aspects as described above.

(First Aspect)

A diagnosis assisting apparatus comprising:
a display;
a voice output unit configured to output a voice; an imaging unit configured to image a subject;
a line of sight detecting unit configured to detect a line of sight direction of the subject from a picked-up image imaged by the imaging unit;
a point of view detecting unit configured to detect a point of view of the subject in a display region of the display based on the line of sight direction;
an output controller configured to display a diagnostic image including a first object shaped like a human which moves according to the voice and a second object in which the first object for moving according to the voice is rotated on a display; and an evaluation unit configured to calculate an evaluation value of a developmental disorder of the subject based on the point of view detected by the point of view detecting unit when the diagnostic image is displayed.

(Second Aspect)

A diagnosis assisting apparatus comprising:
a display;
an imaging unit configured to image a subject;
a line of sight detecting unit configured to detect a line of sight direction of the subject from a picked-up image imaged by the imaging unit;
a point of view detecting unit configured to detect a point of view of the subject in a display region of the display based on the line of sight direction;

an output controller configured to display a diagnostic image on the display; and an evaluation unit configured to calculate an evaluation value of the subject based on the point of view detected by the point of view detecting unit when the diagnostic image is displayed, wherein the output controller further displays an evaluation result by the evaluation unit by using a specified display method of a first display method for displaying the result relative to the subject and a second display method for displaying the result relative to a diagnosing person.

(Third Aspect)

A diagnosis assisting apparatus comprising:
a display;
an imaging unit configured to image a subject;
a line of sight detecting unit configured to detect a line of sight direction of the subject from a picked-up image imaged by the imaging unit;
a point of view detecting unit configured to detect a point of view of the subject in a display region of the display based on the line of sight direction; and
an output controller configured to display a plurality of diagnostic images on the display, wherein
the output controller further displays a result screen on the display, and the result screen includes a first region where the subject is displayed so as be selected, a second region where an evaluation item of the point of view is displayed so as to be selected, and a third region where a detection result of the point of view, which is displayed relative to the subject selected from the first region, relative to the evaluation item selected from the second region is displayed.

(Fourth Aspect)

A diagnosis assisting apparatus comprising:
a display;
an imaging unit configured to image a subject;
a line of sight detecting unit configured to detect a line of sight direction of the subject from a picked-up image imaged by the imaging unit;
a point of view detecting unit configured to detect a point of view of the subject in a display region of the display based on the line of sight direction;
an output controller configured to display a diagnostic image on the display, and at the same time, display an image, which is an image before the diagnosis having a background in a display mode different from that of the diagnostic image, to make the point of view of the subject approach a specific position on the display before the diagnostic image is displayed; and
an evaluation unit configured to evaluate a degree of developmental disorder of the subject based on the point of view detected by the point of view detecting unit when the diagnostic image is displayed.

(Fifth Aspect)

A diagnosis assisting apparatus comprising:
a display;
an imaging unit configured to image a subject;
a position detecting unit configured to detect an eye position of the subject from a picked-up image imaged by the imaging unit;
a distance detecting unit configured to detect a distance between the imaging unit and the eye position of the subject; and
an output controller configured to display an image indicating the eye position of the subject corresponding to the eye position detected by the position detecting unit in a reference image indicating a range of a reference region included in an imaging region of the imaging unit on the display while the display mode is changed according to the distance detected by the distance detecting unit, and at the same time, display a moving image in the reference image.

(Sixth Aspect)

A diagnosis assisting apparatus comprising:

a display;

an imaging unit configured to image a subject;

a line of sight detecting unit configured to detect a line of sight direction of the subject from a picked-up image imaged by the imaging unit;

a point of view detecting unit configured to detect a point of view of the subject in a display region of the display based on the line of sight direction; and an output controller configured to sequentially display a plurality of images different from each other, which is used to correct the position of the point of view detected by the point of view detecting unit, at different positions from each other on the display.

(Seventh Aspect)

A diagnosis assisting apparatus comprising:

a display;

a voice output unit configured to output voice;

an imaging unit configured to image a subject;

a line of sight detecting unit configured to detect a line of sight direction of the subject from a picked-up image imaged by the imaging unit;

a point of view detecting unit configured to detect a point of view of the subject in a display region of the display based on the line of sight direction; and an output controller configured to display a diagnostic image on the display and at the same time display an image before the diagnosis, which is decreased in size having a specific position as a center on the display after the image is moved according to the voice, before the diagnostic image is displayed, wherein the point of view detecting unit detects the point of view of the subject in a case where the diagnostic image is displayed.

(Eighth Aspect)

A diagnosis assisting apparatus comprising:

a display;

an imaging unit configured to image a subject;

a line of sight detecting unit configured to detect a line of sight direction of the subject from a picked-up image imaged by the imaging unit;

a point of view detecting unit configured to detect a point of view of the subject in a display region of the display based on the line of sight direction; and an output controller configured to display a first image used to calibrate a parameter to detect the line of sight direction, a second image used to correct a position of the point of view detected by the point of view detecting unit, and a third image used for the diagnosis on the display in this order.

The diagnosis assisting apparatus and the method for assisting the diagnosis according to the present invention has an effect to improve the diagnosis accuracy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A diagnosis assisting apparatus comprising:

a display;

an imaging unit configured to image a subject using a camera;

a line of sight detecting unit configured to detect, by calculation by a controller, a line of sight direction of the subject from a picked-up image imaged by the imaging unit;

a point of view detecting unit configured to detect, by calculation by the controller, a point of view of the subject in a display region of the display based on the line of sight direction; and an output controller configured to output by the controller and sequentially display a plurality of images different from each other, which is used to correct a detected point of view detected by the point of view detecting unit, at different positions from each other on the display, each of the plurality of images being surrounded by a frame, wherein the output controller is configured to display the frame in which one of the plurality of images is to be displayed, and after displaying the frame in the display, display the one of the plurality of images in the display in such a manner that the one of the plurality of images moves from outside of the frame toward inside of the frame.

2. A method for assisting diagnosis comprising:

detecting, by calculation by a controller, a line of sight direction of a subject from a picked-up image imaged by an imaging unit using a camera for imaging the subject;

detecting, by calculation by the controller, a point of view of the subject in a display region on a display based on the line of sight direction; and outputting by the controller and sequentially displaying a plurality of images different from each other, which is used to correct a detected point of view detected by the point of view detecting step, at different positions from each other on the display, each of the plurality of images being surrounded by a frame, wherein the outputting and sequentially displaying the plurality of images includes displaying the frame in which one of the plurality of images is to be displayed, and after displaying the frame in the display, displaying the one of the plurality of images in the display in such a manner that the one of the plurality of images moves from outside of the frame toward inside of the frame.

* * * * *